United States Patent
Neri et al.

(10) Patent No.: US 11,103,592 B2
(45) Date of Patent: Aug. 31, 2021

(54) IL2 AND TNF MUTANT IMMUNOCONJUGATES

(71) Applicant: PHILOGEN S.P.A., Siena (IT)

(72) Inventors: Dario Neri, Buchs (CH); Roberto De Luca, Rivera (CH); Sarah Wulhfard, Baden (CH)

(73) Assignee: PHILOGEN S.P.A.

( * ) Notice: Subject to any disclaimer, the term of this patent is extended or adjusted under 35 U.S.C. 154(b) by 206 days.

(21) Appl. No.: 16/348,371

(22) PCT Filed: Nov. 8, 2017

(86) PCT No.: PCT/EP2017/078652
§ 371 (c)(1),
(2) Date: May 8, 2019

(87) PCT Pub. No.: WO2018/087172
PCT Pub. Date: May 17, 2018

(65) Prior Publication Data
US 2020/0061203 A1    Feb. 27, 2020

(30) Foreign Application Priority Data

Nov. 9, 2016 (GB) ..................................... 1618888
Aug. 11, 2017 (GB) ..................................... 1712916

(51) Int. Cl.
| | | |
|---|---|---|
| A61K 47/68 | (2017.01) | |
| A61P 35/00 | (2006.01) | |
| A61K 38/19 | (2006.01) | |
| A61K 38/20 | (2006.01) | |
| C07K 16/18 | (2006.01) | |

(52) U.S. Cl.
CPC ........ *A61K 47/6813* (2017.08); *A61K 38/191* (2013.01); *A61K 38/2013* (2013.01); *A61K 47/6843* (2017.08); *A61P 35/00* (2018.01); *C07K 16/18* (2013.01); *C07K 2317/622* (2013.01); *C07K 2317/626* (2013.01); *C07K 2317/73* (2013.01); *C07K 2319/33* (2013.01)

(58) Field of Classification Search
None
See application file for complete search history.

(56) References Cited

FOREIGN PATENT DOCUMENTS

| WO | 2013045125 A1 | 4/2013 |
| WO | 2015007903 A1 | 1/2015 |
| WO | 2016180715 A1 | 11/2016 |

OTHER PUBLICATIONS

Communication pursuant to Article 94(3) EPC, dated Jun. 6, 2020, issued in corresponding EP 17 801 386.8-1111, filed Nov. 8, 2017.
DeLuca, Roberto et al., "Potency-matched Dual Cytokine-Antibody Fusion Proteins for Cancer Therapy", Mol. Cancer Ther., 16(11): 2442-2451 (2017).
Martin, Andrew C.R. et al., "Antibodies Abysis—new database", Nov. 17, 2015, Retrieved from the Internet: URL: http://www.bioinf.org.uk/abs/.
Halin, Cornelia et al., "Synergistic Therapeutic Effects of a Tumor Targeting Antibody Fragment, Fused to Interleukin 12 and to Tumor Necrosis Factor alpha", Cancer Res., 63: 3202-3210 (2003).
List, Thomas et al., "A Chemically Defined Trifunctional Antibody-Cytokine-Drug Conjugate with Potent Antitumor Activity", Mol. Cancer Ther., 13(11): 2641-52 (2014).
Lu, Wenshu et al., "Evolutionarily conserved primary TNF sequences relate to its primitive functions in cell death induction", Journal of Cell Science, 129: 108-120 (2016).
Neri, Dario et al., "Immunocytokines for cancer treatment: past, present and future", Curr. Opin. Immunal., 40: 96-102 (2016).
Nunez-Prado, Natalia et al., "The coming of age of engineered multivalent antibodies", Drug Discovery Today, 20(5): 588-594 (2015).
Pretto, Francesco et al., "Preclinical evaluation of IL2-based immunocytokines supports their use in combination with dacarbazine, paclitaxel and TNF-based immunotherapy", Cancer Immunol. Immunother., 63: 901-910 (2014).
Shingarova, L.N. et al., "Human tumor necrosis factor mutants: preparation and some properties",Database Medline, US National Library of Medicine (NLM), Bethesda, MD, US, Apr. 1996 (Apr. 1996), Database Accession No. NLM8768260 [Abstract].
Van Ostade, Xaveer, The EMBO Journal, "Localization of the active site of human tumour necrosis factor (hTNF) by mutational analysis", 10(4): 827-836 (1991).
Shingarova, L.N. et al., "Human tumor necrosis factor mutants: preparation and some properties", Bioorganicheskaia Khimiia, 22(4): 243-251 (1996) [Abstract].
International Search Report, dated Jan. 24, 2018, issued in corresponding PCT/EP2017/078652, filed Nov. 8, 2017.
Written Opinion, dated Jan. 24, 2018, issued in corresponding PCT/EP2017/078652, filed Nov. 8, 2017.

*Primary Examiner* — Daniel C Gamett
(74) *Attorney, Agent, or Firm* — Kathleen D. Rigaut; Howson & Howson LLP

(57) ABSTRACT

The present application relates to conjugates comprising interleukin 2 (IL2), and a mutant of tumour necrosis factor, such as tumour necrosis factor alpha (TNFα), and an antibody molecule. The antibody molecule preferably binds to an antigen associated with neoplastic growth and/or angiogenesis, such as the Extra-Domain A (EDA) or Extra-Domain B (EDB) of fibronectin. The conjugate may be used in the treatment of cancer.

13 Claims, 5 Drawing Sheets

Figure 1:
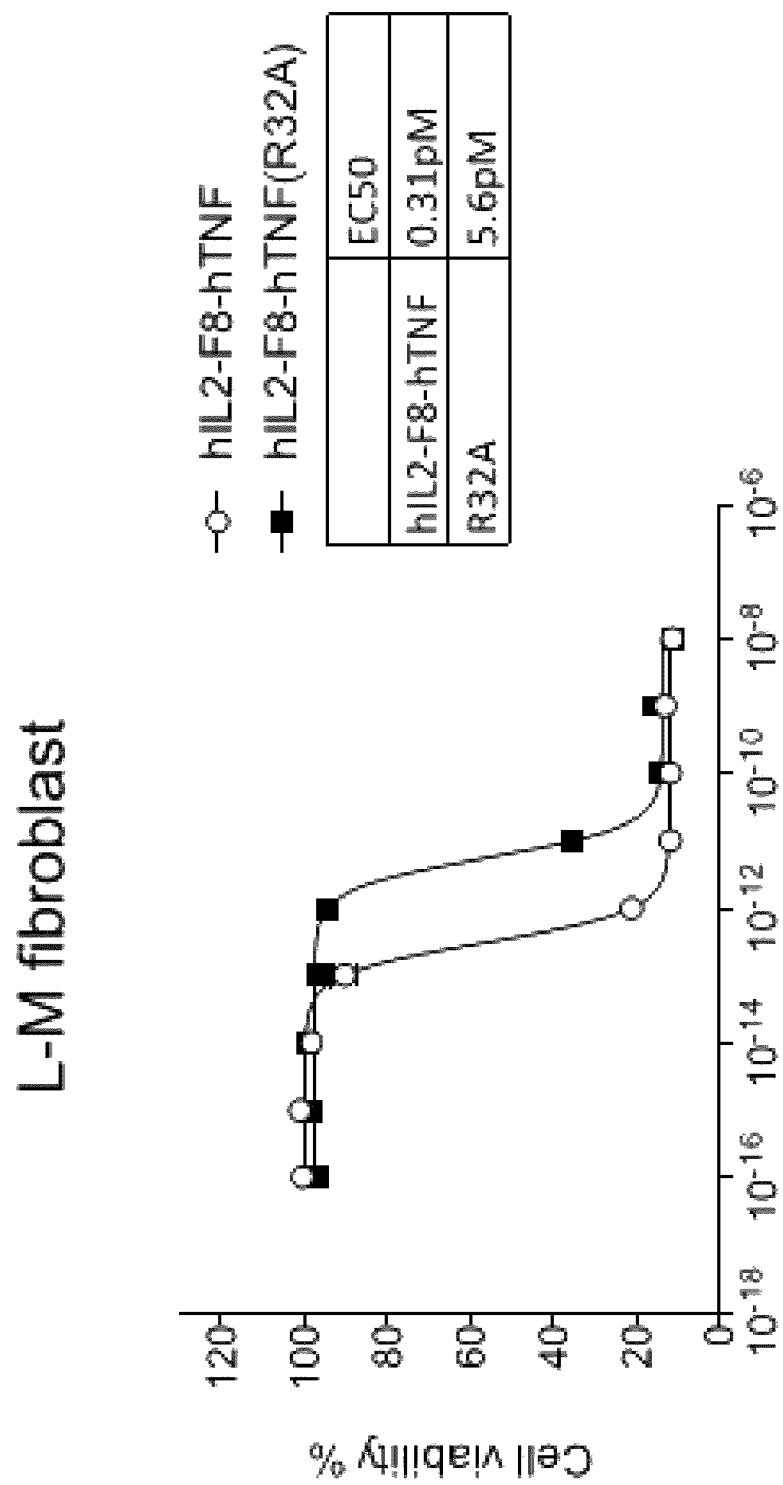

Specification includes a Sequence Listing.

IL2 AND TNF MUTANT IMMUNOCONJUGATES

CROSS-REFERENCE TO RELATED APPLICATIONS

This application is a § 371 of International Application No. PCT/EP2017/078652, filed Nov. 8, 2017, which claims priority from Great Britain Patent Application No. 1618888.0, filed Nov. 9, 2016 and Great Britain Patent Application No. 1712916.4, filed Aug. 11, 2017. The entire disclosure of each of the aforesaid applications is incorporated by reference in the present application.

FIELD

The present invention relates to conjugates comprising interleukin 2 (IL2), a mutant of a tumour necrosis factor, such as tumour necrosis factor alpha (TNFα), and an antibody molecule. The antibody molecule preferably binds to an antigen associated with neoplastic growth and/or angiogenesis, such as the Extra-Domain A (EDA) and the Extra-Domain B (EDB) of fibronectin. The conjugates may be used, for example, in the treatment of cancer.

BACKGROUND

Many cytokines have shown potent anti-tumour activities in preclinical experiments and represent promising agents for cancer therapy. However, despite encouraging results in animal models, only a few cytokines, such as Proleukin 1 (IL2), Roferon A1 (interferon alpha-2a [IFNα 2a]), Intron A1 (IFNα 2b), Beromun 1 (recombinant TNFα) have been approved as anticancer drugs. Current indications for cytokines include metastatic renal cell cancer, malignant melanoma, hairy cell leukemia, chronic myeloid lymphoma, sarcoma and multiple myeloma. The cytokines may be either administered alone or in combination with chemotherapy.

A further difficulty with pro-inflammatory cytokines in particular is that their use in therapy is often hindered by substantial toxicity even at low doses, which prevents the escalation to therapeutically active doses (Hemmerle et al. (2013) Br. J. Cancer 109, 1206-1213).

In an attempt to increase the therapeutic index of certain cytokines, antibody-cytokine fusion proteins (also referred to as "immunocytokines") have been proposed. In these conjugates, the antibody serves as a "vehicle" for a selective accumulation at the site of disease, while the cytokine payload is responsible for the therapeutic activity (Pasche & Neri, 2012, Drug Discov. Today, 17, 583). Certain immunocytokines based on pro-inflammatory payloads (such as IL2, IL4, IL12, and TNFα) display potent anti-cancer activity in mouse models (Hess et al., 2014, Med. Chem. Comm., 5, 408) and have produced encouraging results in patients with both solid tumours and haematological malignancies (Eigentler et al., 2011, Clin. Cancer Res. 17, 7732-7742; Papadia et al., 2013, J. Surg. Oncol. 107, 173-179; Gutbrodt et al., 2013, Sci. Transl. Med. 5, 201-204; Weide et al., 2014, Cancer Immunol. Res. 2, 668-678; Danielli et al., 2015, Cancer Immunol. Immunother. 64, 113-121]. The F8 antibody (specific to the alternatively-spliced EDA domain of fibronectin, a marker of tumour angiogenesis; Rybak et al. (2007) Cancer Res. 67, 10948-10957) has been used for tumour targeting, both alone and fused to either TNF or IL2 (Villa et al. (2008) Int. J. Cancer 122, 2405-2413; Hemmerle et al. (2013) Br. J. Cancer 109, 1206-1213; Frey et al. (2008) J. Urol. 184, 2540-2548).

Constructs that comprise three copies of a single modified cytokine of the TNF superfamily that has reduced activity to its receptor have been reported (WO2015/007903). The constructs are specifically delivered to target cells by a targeting moiety. Modified cytokines used in these constructs include mutant TNF with an activity range between 0.02% and 5% of wild type TNF, including mutant TNFs with Y87Q, I97S, Y115A, Y87F, Y115G, or I97A substitutions. The effect of R32G is also reported.

In some cases, immunocytokines can mediate tumour eradication in mouse models of cancer when used as single agents (Gutbrodt et al., 2013, Sci. Transl. Med. 5, 201-204]. In most cases, however, a single immunocytokine product is not able to induce complete cancer eradication. However, cancer cures have been reported for combinations of immunocytokines with cytotoxic agents (Moschetta et al., 2012, Cancer Res. 72, 1814-1824], intact antibodies (Schliemann et al., 2009, Blood, 113, 2275-2283] and external beam radiation (Zegers et al., 2015, Clin. Cancer Res., 21, 1151-1160).

In addition, several combinations of immunocytokines have been used in therapy. For example, conjugates L19-IL2 and L19-TNFα were able to cure neuroblastoma in a fully syngeneic mouse model of the disease, whereas the individual immunocytokines used as single agents did not result in eradication of the disease (Balza et al., 2010, Int. J. Cancer, 127, 101). The combination of IL2 and TNFα payloads has also shown promising results in clinical trials. The fusion proteins L19-IL2 and L19-TNF were shown to potently synergize for the intralesional treatment of certain solid tumours in the mouse (Schwager et al., 2013, J. Invest. Dermatol. 133, 751-758). The corresponding fully human fusion proteins have been administered intralesionally to patients with Stage IIIC melanoma (Danielli et al., 2015, Cancer Immunol. Immunother. 64, 113-121), showing better results compared to the intralesional administration of interleukin-2 (Weide et al., 2011, Cancer—116, 4139-4146) or of L19-IL2 (Weide et al., 2014, Cancer Immunol. Immunother. 2, 668-678). However, the genetic fusion of a cytokine to an antibody does not always result in increased efficacy. For example, the fusion of Interleukin-17 to a targeting antibody did not reduce tumour growth (Pasche et al., 2012, Angiogenesis 15, 165-169).

There have also been attempts to generate "dual immunocytokines" in which an antibody is genetically fused to two different cytokines. For instance, interleukin-12 (IL12) and TNFα have been incorporated into a single molecular entity. However, these attempts have not been successful and have not led to clinical development programs. Specifically, a triple fusion, consisting of: (i) the L19 antibody in scFv format (specific to the alternatively-spliced EDB domain of fibronectin, a marker of tumour angiogenesis); (ii) murine TNFα; and (iii) murine IL12 in single-chain format has been described (Halin et al., 2003, Cancer Res., 63, 3202-3210). This fusion protein could be expressed and purified to homogeneity. The fusion protein also bound to the cognate antigen with high affinity and specificity, but (unlike L19-TNFα and L19-IL12), it failed to localize to solid tumours in vivo, as evidenced by quantitative biodistribution studies in tumour-bearing mice. The behaviour of dual immunocytokines in vivo is therefore extremely unpredictable.

Bi-functional cytokine fusion proteins in which the cytokines were linked to an intact whole antibody (or the Fc portion of an antibody) have also been described (Gillies et al., 2002, Cancer Immunol. Immunother. 51, 449). These fusion proteins comprised interleukin-2/interleukin-12 (IL2/IL12), or interleukin-4/granulocyte-macrophage colonystimulating factor (IL4/GM-CSF). Cytokine activity was retained in constructs where the cytokines were fused in tandem at the carboxyl terminus of the Fc or antibody heavy (H) chain, as well as in constructs where one cytokine was fused at the carboxyl terminus of the H chain while the second cytokine was fused to the amino terminus of either the H or light (L) chain variable region. Antigen binding of the antibody-cytokine fusion proteins was maintained. However, therapeutic activities in vivo were reported only for gene therapy applications (i.e. tumour cells transfected with the appropriate IL2/IL12 immunocytokines), but not with therapeutic proteins. Bi-functional cytokine fusion proteins comprising other types of targeting moieties are not reported.

The intrinsic complexity of successfully expressing immunoconjugates containing two different cytokines in a single molecule (also referred to as "dual immunocytokines") and the unpromising results obtained with such molecules as discussed above (for example in Halin et al (2003)), mean that these molecular formats have not been pursued for clinical applications.

SUMMARY

The present inventors have recognised that the use of a reduced activity tumour necrosis factor (TNF) mutant improves the tolerability of a dual immunocytokine that comprises TNF and IL2, as well as a targeting antibody molecule, without affecting efficacy.

An aspect of the present invention provides a conjugate comprising interleukin-2 (IL2), a TNF mutant having reduced activity, and an antibody molecule which binds an antigen associated with neoplastic growth and/or angiogenesis.

Another aspect of the invention provides a nucleic acid molecule encoding such a conjugate, as well as an expression vector comprising such a nucleic acid. A host cell comprising such a vector is also contemplated.

Another aspect of the invention provides a conjugate described herein for use in a method of treating cancer by targeting IL2 and a TNF mutant, preferably a TNFα mutant, to the neovasculature in vivo, as well as a conjugate described herein for use in a method of delivering IL2 and a TNF mutant, preferably a TNFα mutant, to the tumour neovasculature in a patient.

Another aspect of the invention provides a method of treating cancer by targeting IL2 and a TNF mutant, preferably a TNFα mutant, to the neovasculature in a patient, the method comprising administering a therapeutically effective amount of a conjugate described herein to the patient, as well as a method of delivering IL2 and a TNF mutant, preferably a TNFα mutant, to the tumour neovasculature in a patient comprising administering to the patient a conjugate described herein.

In addition, another aspect of the invention provides the use of a conjugate described herein for the preparation of a medicament for the treatment of cancer. The use of a conjugate described herein for the preparation of a medicament for delivery of IL2 and a TNF mutant, preferably a TNFα mutant, to the neovasculature of a tumour is similarly contemplated.

BRIEF DESCRIPTION OF THE FIGURES

FIG. 1 shows the cell killing activity of huIL2-F8-huTNFα conjugate and huIL2-F8-huTNFα (R32A) mutant conjugate. The conjugates tested were huIL2-F8-huTNFα and huIL2-F8-huTNFα (R32A) which comprised a mutated TNFα at the position 32, IL2 and the anti-ED-A antibody F8. The cell killing activity of this mutated conjugate was compared with the cell killing activity observed in the presence of conjugate huIL2-F8-huTNFα. The cell killing activity of the huIL2-F8-huTNFα (R32A) mutant conjugate was lower compared to the huIL2-F8-huTNFα conjugate, as can be seen from the EC50 values. The EC50 value represents the drug concentration required for half-maximal activity.

FIG. 2 shows the in vivo targeting performance of the huIL2-F8-huTNFα (R32A) mutant conjugate evaluated by biodistribution analysis. The huIL2-F8-huTNFα (R32A) mutant conjugate selectively accumulated in tumour in a mouse model of F9 teratocarcinoma.

FIG. 3 shows the IL2 bioactivity assay of the huIL2-L19-huTNFα (R32A) mutant conjugate, based on the proliferation of CTLL-2 cells.

FIG. 4 shows the TNF bioactivity assay of the huIL2-L19-huTNFα (R32A) mutant conjugate, based on the killing of HT1080 cells.

FIG. 5 shows the quantitative biodistribution analysis of radioiodinated huIL2-L19-huTNFα (R32A) mutant conjugate in immunocompetent mice bearing F9 teratocarcinoma tumours.

DETAILED DESCRIPTION

The present invention relates to a conjugate comprising (i) an interleukin-2 (IL2) moiety, (ii) a moiety which is a tumour necrosis factor (TNF) mutant having reduced activity, and (iii) an antibody molecule which binds an antigen associated with neoplastic growth and/or angiogenesis.

The term "antibody molecule" describes an immunoglobulin whether natural or partly or wholly synthetically produced. The term also relates to any polypeptide or protein comprising an antibody antigen-binding site. Antibody molecules may have been isolated or obtained by purification from natural sources, or else obtained by genetic recombination, or by chemical synthesis, and that they may contain unnatural amino acids.

As antibodies can be modified in a number of ways, the term "antibody molecule" should be construed as covering any specific binding member or substance having an antibody antigen-binding site with the required specificity and/or binding to antigen. Thus, this term covers antibody fragments, in particular antigen-binding fragments, and derivatives, including any polypeptide comprising an antibody antigen-binding site, whether natural or wholly or partially synthetic. Chimeric molecules comprising an antibody antigen-binding site, or equivalent, fused to another polypeptide (e.g. belonging to another antibody class or subclass) are therefore included. Cloning and expression of chimeric antibodies are described in EP-A-0120694 and EP-A-0125023, and a large body of subsequent literature.

As mentioned above, fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965); (ix) "diabodies", multivalent or multispecific fragments constructed by gene fusion (WO94/13804; Holliger et al. (1993a), Proc. Natl. Acad. Sci. USA 90 6444-6448) and (x) a single chain diabody format wherein each of the VH and VL domains within a set is connected by a short or 'non-flexible' peptide linker. Fv, scFv or diabody molecules may be stabilized by the incorporation of disulphide bridges linking the VH and VL domains (Reiter et al. (1996), Nature Biotech, 14, 1239-1245). A single chain Fv (scFv) may be comprised within a mini-immunoglobulin or small immunoprotein (SIP), e.g. as described in (Li et al., (1997), Protein Engineering, 10: 731-736). A SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming a homo-dimeric mini-immunoglobulin antibody molecule. Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The half-life of antibody molecules for use in the conjugates described herein, may be increased by a chemical modification, especially by PEGylation, or by incorporation in a liposome.

Suitable antibody molecules for use in the conjugates described herein include diabodies or, more preferably scFvs. Diabodies and scFvs do not comprise an antibody Fc region, thus potentially reducing the effects of anti-idiotypic reaction. Preferably, the antibody molecule for use in the conjugates described herein is a scFv.

Where the antibody molecule is a scFv, the VH and VL domains of the antibody are preferably linked by a 10 to 20 amino acid linker, by a 14 to 20 amino acid linker, preferably by a 10 to 14 amino acid linker. Suitable linkers are known in the art and available to the skilled person. For example, a linker may have the sequence set forth in SEQ ID NO: 3, SEQ ID NO: 50 or SEQ ID NO: 51

Where the antibody molecule is a diabody, the VH and VL domains may be linked by a 5 to 12 amino acid linker. A diabody comprises two VH-VL molecules which associate to form a dimer. The VH and VL domains of each VH-VL molecule may be linked by a 5 to 12 amino acid linker.

The present inventors have shown that a conjugate comprising IL2; a mutant of TNFα; and an antibody molecule which binds the Extra-Domain A (ED-A) of fibronectin exhibits reduced toxicity compared to a conjugate comprising IL2; TNFα; and an antibody molecule which binds the Extra-Domain A (ED-A) of fibronectin. Furthermore, the present inventors have also shown that a conjugate comprising IL2; a mutant of TNFα; and an antibody molecule which binds the Extra-Domain B (ED-B) isoform of fibronectin exhibits reduced toxicity compared to the recombinant TNFα. Other conjugates comprising IL2 and a mutant of TNF, preferably TNFα, and an antibody molecule which binds an antigen associated with neoplastic growth and/or angiogenesis have similarly reduced toxicity.

The toxicity of a conjugate comprising a TNF mutant as described herein may be reduced compared to the corresponding conjugate comprising wild-type TNF. Reduced toxicity may include improved tolerability in a patient, for example a reduction in one or more adverse symptoms associated with administration of the conjugate(s) to the patient. Adverse symptoms reduced by the toxicity may include weight loss, nausea, vomiting, fever, chills, flushing, urticaria, rash, pulmonary toxicity, dyspnea, hypotension, anaphylaxis, serum sickness, increased creatinine, headache.

Furthermore, the reduced toxicity of the TNF mutant in the conjugate increases the synergistic effect of the IL2 moiety, which can be administered at a higher dose due to the lower activity of the TNF mutant. The potency matched cytokines in the conjugate may therefore be useful in therapeutic applications.

The present inventors have also shown that a conjugate comprising IL2 and a mutant of TNFα; and an antibody molecule which binds the Extra-Domain A (ED-A) of fibronectin can successfully target tumour neovasculature in vivo. Furthermore, the present inventors have also shown that a conjugate comprising IL2 and a mutant of TNFα; and an antibody molecule which binds the Extra-Domain B (ED-B) of fibronectin can successfully target tumour neovasculature in vivo. Other conjugates comprising IL2 and a mutant of TNF, preferably TNFα, and an antibody molecule which binds an antigen associated with neoplastic growth and/or angiogenesis will similarly be suitable to target IL2 and mutant of TNF to the tumour neovasculature and thus find application in cancer treatment. A conjugate comprising IL2; TNFα; and an antibody molecule which binds the Extra-Domain A (ED-A) of fibronectin has also been shown to target tumour neovasculature in vivo (PCT/EP2016/060128).

Many antigens associated with neoplastic growth and/or angiogenesis are known in the art, as are antibodies capable of binding such antigens. In additions, antibodies against a given antigen can be generated using well-known methods such as those described in the present application. In some embodiments, the antigen may be an extra-cellular matrix component associated with neoplastic growth and/or angiogenesis, such as fibronectins, including the Extra-Domain A (ED-A) isoform of fibronectin (A-FN), the Extra-Domain B (ED-B) isoform of fibronectin (B-FN), tenascin C, the ED-A of fibronectin, the ED-B of fibronectin, or the A1 Domain of Tenascin C. Antibodies which bind the ED-A of fibronectin, and thus also A-FN, are known in the art and include antibody F8. Antibodies which bind the ED-B of fibronectin, or the A1 Domain of Tenascin C (and thus also the B-FN and tenascin C) are also known in the art and include antibodies L19 and F16, respectively. Antibodies which bind the ED-B of fibronectin, or the A1 Domain of Tenascin C, including antibodies L19 and F16, have been shown to be capable of specifically targeting the tumour neovasculature in vivo. Thus, a conjugate described herein, comprising IL2, a mutant of TNF, preferably TNFα, and an antibody molecule which binds an antigen associated with neoplastic growth and/or angiogenesis, preferably exhibits reduced toxicity when administered to a patient, compared with administration of a conjugate comprising IL2, TNF and the antibody molecule, to the patient.

Other antigens which are associated with neoplastic growth and/or angiogenesis include carbonic anhydrase IX (a marker of renal cell carcinoma), A33 and CEA (good markers of colorectal cancer), HER2 (a marker of breast cancer), PSMA (a marker of prostate cancer) and fibroblast activation protein (a protease, present both as membrane bound protein and as shed protein, on activated fibroblasts and on certain types of tumour cells). Conjugates comprising IL2 and a mutant of TNF, preferably TNFα, and an antibody molecule which binds antigens such as carbonic anhydrase IX, A33, CEA, HER2, PSMA, or fibroblast activation protein are similarly suitable to target IL2 and TNF to the tumour neovasculature and thus find application in cancer treatment and will exhibit reduced toxicity.

In some preferred embodiments, an antibody molecule for use as described herein may have the CDRs and/or the VH and/or VL domains of antibodies F8, L19 or F16 described herein. An antibody molecule for use as described herein preferably has the CDRs of antibody F8 set forth in SEQ ID NOs 6-11. More preferably, an antibody for use as described herein may comprise the VH and/or VL domains of antibody F8 set forth in SEQ ID NOs 2 and 4. Yet more preferably, an antibody for use as described herein comprises the VH and VL domains of antibody F8 set forth in SEQ ID NOs 2 and 4. The F8 antibody is preferably in scFv or diabody format, most preferably in scFv format. Where the F8 antibody is in scFv format, the antibody molecule for use as described herein preferably has the amino acid sequence set forth in SEQ ID NO: 5.

Another antibody molecule for use as described herein preferably has the CDRs of antibody L19 set forth in SEQ ID NOs 18-23. More preferably, an antibody for use as described herein may comprise the VH and/or VL domains of antibody L19 set forth in SEQ ID NOs 24 and 25. Yet more preferably, an antibody for use as described herein comprises the VH and VL domains of antibody L19 set forth in SEQ ID NOs 24 and 25. The L19 antibody is preferably in scFv or diabody format, most preferably in scFv format. Where the L19 antibody is in scFv format, the antibody molecule for use as described herein preferably has the amino acid sequence set forth in SEQ ID NO: 26.

An antibody molecule for use as described herein may bind the A-FN and/or the ED-A of fibronectin, with the same affinity as anti-ED-A antibody F8 e.g. in scFv format, or with an affinity that is better. An antibody molecule for use as described herein may bind the B-FN and/or the ED-B of fibronectin, with the same affinity as anti-ED-B antibody L19 e.g. in scFv format, or with an affinity that is better. An antibody molecule for use as described herein may bind Tenascin C and/or the A1 domain of tenascin C, with the same affinity as anti-Tenascin C antibody F16 e.g. in scFv format, or with an affinity that is better.

An antibody molecule for use as described herein may bind to the same epitope on A-FN and/or the ED-A of fibronectin as anti-ED-A antibody F8. An antibody molecule of the present invention may bind to the same epitope on B-FN and/or the ED-B of fibronectin as anti-ED-B antibody L19. An antibody molecule of the present invention may bind to the same epitope on tenascin C and/or the A1 domain of tenascin C as antibody F16.

Variants of antibody molecules disclosed herein may be produced and used in the present invention. The techniques required to make substitutions within amino acid sequences of CDRs, antibody VH or VL domains, in particular the framework regions of the VH and VL domains, and antibody molecules generally are available in the art. Variant sequences may be made, with substitutions that may or may not be predicted to have a minimal or beneficial effect on activity, and tested for ability to bind A-FN and/or the ED-A of fibronectin, B-FN and/or the ED-B of fibronectin, tenascin C and/or the A1 domain of tenascin C, and/or for any other desired property.

It is contemplated that from 1 to 5, e.g. from 1 to 4, including 1 to 3, or 1 or 2, or 3 or 4, amino acid alterations (addition, deletion, substitution and/or insertion of an amino acid residue) may be made in one or more of the CDRs and/or the VH and/or the VL domain of an antibody molecule as described herein. Thus, an antibody molecule which binds the FN-A, FN-B, or tenascin C, may comprise the CDRs and/or the VH and/or the VL domain of antibody F8, L19, or F16 described herein with 5 or fewer, for example, 5, 4, 3, 2 or 1 amino acid alterations within the CDRs and/or the VH and/or the VL domain. For example, an antibody molecule which binds the FN-A, FN-B, or tenascin C, may comprise the VH and/or the VL domain of antibody F8, L19, or F16 described herein with 5 or fewer, for example, 5, 4, 3, 2 or 1 amino acid alterations within the framework region of the VH and/or VL domain. An antibody molecule that binds the FN-A or ED-A of fibronectin, as referred to herein, thus may comprise the VH domain shown in SEQ ID NO: 2 and/or the VL domain shown in SEQ ID NO: 4 with 5 or fewer, for example, 5, 4, 3, 2 or 1 amino acid alterations within the framework region of the VH and/or VL domain. Such an antibody molecule may bind the ED-A isoform or ED-A of fibronectin with the same or substantially the same, affinity as an antibody molecule comprising the VH domain shown in SEQ ID NO: 2 and the VL domain shown in SEQ ID NO: 4 or may bind the ED-A isoform or ED-A of fibronectin with a higher affinity than an antibody molecule comprising the VH domain shown in SEQ ID NO: 2 and the VL domain shown in SEQ ID NO: 4. An antibody molecule that binds the FN-B or ED-B of fibronectin, as referred to herein, thus may comprise the VH domain shown in SEQ ID NO: 24 and/or the VL domain shown in SEQ ID NO: 25 with 5 or fewer, for example, 5, 4, 3, 2 or 1 amino acid alterations within the framework region of the VH and/or VL domain. Such an antibody molecule may bind the ED-B isoform or ED-B of fibronectin with the same or substantially the same, affinity as an antibody molecule comprising the VH domain shown in SEQ ID NO: 24 and the VL domain shown in SEQ ID NO: 25 or may bind the ED-B isoform or ED-B of fibronectin with a higher affinity than an antibody molecule comprising the VH domain shown in SEQ ID NO: 24 and the VL domain shown in SEQ ID NO: 25.

An antibody molecule for use as described herein may comprise a VH and/or VL domain that has at least 70%, more preferably one of at least 75%, 80%, 85%, 90%, 95%, 96%, 97%, 98%, 99% or 100%, sequence identity to the VH and/or VL domain, as applicable, of antibody F8, L19, or F16 set forth in SEQ ID NOs 2, 4, 24, 25, 33, and 34. An antibody molecule for use as described herein may have at least 70%, more preferably one of at least 75%, 80%, 85%, 90%, 95%, 96%, 97%, 98%, 99% or 100%, sequence identity to the amino acid sequence of the F8, L19, or F16 antibodies set forth in SEQ ID NOs 5, 26, 35, and 46, respectively.

An antigen binding site is the part of a molecule that recognises and binds to all or part of a target antigen. In an antibody molecule, it is referred to as the antibody antigen-binding site or paratope, and comprises the part of the antibody that recognises and binds to all or part of the target antigen. Where an antigen is large, an antibody may only bind to a particular part of the antigen, which part is termed an epitope. An antibody antigen-binding site may be provided by one or more antibody variable domains. An antibody antigen-binding site preferably comprises an antibody light chain variable region (VL) and an antibody heavy chain variable region (VH).

An antigen binding site may be provided by means of arrangement of complementarity determining regions (CDRs). The structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. 4th Edition. US Department of Health and Human Services), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, $4^{th}$ Edition, US Department of Health and Human Services (Kabat et al., (1991a), Sequences of Proteins of Immunological Interest, $5^{th}$ Edition, US Department of Health and Human Services, Public Service, NIH, Washington, and later editions). An antibody typically contains 3 heavy chain CDRs and 3 light chain CDRs. The term "CDR" or "CDRs" may indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

The antigen-binding site of an antibody molecule for use as described herein preferably has the CDRs of antibody F8 set forth in SEQ ID NOs 6-11, the CDRs of antibody L19 set forth in SEQ ID Nos 18-23, or the CDRs of antibody F16 set forth in SEQ ID NOs 27-32. Most preferably, the antigen binding site of an antibody molecule for use as described herein has the CDRs of antibody F8 set forth in SEQ ID NOs 6-11 or the CDRs of antibody L19 set forth in SEQ ID Nos 18-23.

Various methods are available in the art for obtaining antibodies molecules against a target antigen. The antibody molecules for use in the conjugates described herein are preferably monoclonal antibodies, especially of human, murine, chimeric or humanized origin, which can be obtained according to the standard methods well known to the person skilled in the art. An antibody molecule for use in the conjugates described herein is most preferably a human antibody molecule.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody molecule to the constant regions, or constant regions plus framework regions, of a different immunoglobulin (see, for instance, EP-A-184187, GB 2188638A or EP-A-239400, and a large body of subsequent literature). A hybridoma or other cell producing an antibody may also be subject to genetic mutation or other changes, which may or may not alter the binding specificity of antibodies produced.

Techniques available in the art of antibody engineering have made it possible to isolate human and humanised antibodies. For example, human hybridomas can be made as described by Kontermann & Dubel (2001), S, *Antibody Engineering*, Springer-Verlag New York, LLC; ISBN: 3540413545. Phage display, another established technique for generating specific binding members has been described in detail in many publications such as WO92/01047 (discussed further below) and U.S. Pat. Nos. 5,969,108, 5,565, 332, 5,733,743, 5,858,657, 5,871,907, 5,872,215, 5,885,793, 5,962,255, 6,140,471, 6,172,197, 6,225,447, 6,291,650, 6,492,160, 6,521,404 and Kontermann & Dubel (2001), S, *Antibody Engineering*, Springer-Verlag New York, LLC; ISBN: 3540413545. Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against the an antigen associated with neoplastic growth and/or angiogenesis, such as A-FN, B-FN, tenascin C, the ED-A of fibronectin, the ED-B of fibronectin, or the A1 Domain of Tenascin C, according to the usual working methods, by genetic recombination starting with a nucleic acid sequence contained in the cDNA sequence coding for A-FN, B-FN, or tenascin C, or fragment thereof, or by peptide synthesis starting from a sequence of amino acids comprised in the peptide sequence of the A-FN, B-FN, or tenascin C, and/or a fragment thereof.

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

Alternatively, one or more antibody molecules for an antigen associated with neoplastic growth and/or angiogenesis, such as the A-FN, the ED-A, B-FN, the ED-B, tenascin C, or the A1 domain of tenascin C may be obtained by bringing into contact a library of antibody molecules and the antigen or a fragment thereof, e.g. a fragment comprising or consisting of ED-A, ED-B, or the A1 domain of tenascin C, or a peptide fragment thereof, and selecting one or more antibody molecules of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments, such as scFvs, having a spreading action, so that those fragments binding specifically with the antigen which is present on the trap membrane are trapped. The trap membrane may then be treated to identify bound antibody fragments, such as scFvs, for example using colorimetric techniques commonly used to this purpose.

The position of the identified fragments, for example as coloured spots, on the trap filter allows one to go back to the corresponding bacterial colonies which are present on the growth membrane and produce the antibody fragments trapped. Colonies are gathered and grown and the bacteria are distributed onto a new culture membrane, repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO02/46455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404.

Following selection of antibody molecules able to bind the antigen and displayed on bacteriophage or other library particles or molecular complexes, nucleic acid may be taken from a bacteriophage or other particle or molecular complex displaying a said selected antibody molecule. Such nucleic acid may be used in subsequent production of an antibody molecule or an antibody VH or VL variable domain by expression from nucleic acid with the sequence of nucleic acid taken from a bacteriophage or other particle or molecular complex displaying a said selected antibody molecule.

Ability to bind an antigen associated with neoplastic growth and/or angiogenesis, such as the A-FN, B-FN, the ED-A, or the ED-B of fibronectin, tenascin C or the A1 domain of tenascin C or other target antigen or isoform may be further tested, e.g. ability to compete with an antibody specific for the A-FN, B-FN, the ED-A, or the ED-B of fibronectin, tenascin C or the A1 domain of tenascin C, such as antibody F8, L19, or F16.

Novel VH or VL regions carrying CDR-derived sequences for use as described herein may be also generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

Variable domains employed as described herein may be obtained or derived from any germ-line or rearranged human variable domain, or may be a synthetic variable domain based on consensus or actual sequences of known human variable domains. A variable domain can be derived from a non-human antibody. A CDR sequence for use as described herein (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibody molecules for use as described herein. The repertoire may then be displayed in a suitable host system such as the phage display system of WO92/01047, or any of a subsequent large body of literature, including Kay, Winter & McCafferty (1996), so that suitable antibody molecules may be selected. A repertoire may consist of from anything from $10^4$ individual members upwards, for example at least $10^5$, at least $10^6$, at least $10^7$, at least $10^8$, at least $10^9$ or at least $10^{10}$ members.

An antigen associated with neoplastic growth and/or angiogenesis, such as the A-FN, B-FN, the ED-A, or the ED-B of fibronectin, tenascin C or the A1 domain of tenascin C may be used in a screen for antibody molecules, e.g. antibody molecules, for use as described herein. The screen may a screen of a repertoire as disclosed elsewhere herein.

Similarly, one or more, or all three CDRs may be grafted into a repertoire of VH or VL domains that are then screened for an antibody molecule or antibody molecules for an antigen associated with neoplastic growth and/or angiogenesis, such as A-FN, B-FN, the ED-A, or the ED-B of fibronectin, tenascin C or the A1 domain of tenascin C. One or more of the HCDR1, HCDR2 and HCDR3 of antibody F8, L19, or F16, or the set of HCDRs of antibody F8, L19, or F16 may be employed, and/or one or more of the LCDR1, LCDR2 and LCDR3 of antibody F8, L19, or F16 the set of LCDRs of antibody F8, L19, or F16 may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although antibody molecules may comprise a pair of VH and VL domains, single binding domains based on either VH or VL domain sequences may also be used as described herein. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain antibody molecule able to bind an antigen associated with neoplastic growth and/or angiogenesis, such as A-FN, B-FN, the ED-A, or the ED-B of fibronectin, tenascin C or the A1 domain of tenascin C. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain antibody molecule is selected in accordance with phage display techniques such as those described in that reference. This technique is also disclosed in Marks 1992. Fragments of whole antibodies for use as described herein can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

A conjugate as described herein comprises IL2 and a mutant of TNF, preferably TNFα, and an antibody molecule which binds an antigen associated with neoplastic growth and/or angiogenesis, as described herein. The antibody molecule is preferably a scFv or a diabody, most preferably a scFv, as described herein.

IL2 is preferably human IL2.

The IL2 preferably comprises or consist of the sequence set forth in SEQ ID NO: 12. Typically, IL2 has at least 70%, more preferably one of at least 75%, 80%, 85%, 90%, 95%, 96%, 97%, 98%, 99% or 100%, sequence identity to the amino acid sequence set forth in SEQ ID NO: 12. IL2 in conjugates of the invention retains a biological activity of human IL2, e.g. the ability to inhibit cell proliferation.

TNF is preferably human TNF. Where the tumour necrosis factor is TNFα, the TNFα is preferably human TNFα.

The TNF mutant in conjugates described herein is a mutant of TNF which retains biological function of human TNF, e.g. the ability to inhibit cell proliferation but has a reduced activity.

The TNF mutant may comprise one or more mutations which reduce activity relative to the wild-type TNF which lacks the one or more mutations i.e. the TNF mutant is less potent than wild-type TNF. For example, the TNF mutant may comprise a mutation at the position corresponding to position 32 in SEQ ID NO: 15 or position 52 of SEQ ID NO: 17. In some embodiments, the R at said position may be substituted for a different amino acid, preferably an amino acid other than G, for example a non-polar amino acid, preferably A, F, or V, most preferably A. The sequences of examples of suitable TNF mutants are set forth in SEQ ID NO: 37, 39, 54-55, 56-57, respectively.

The identity of the residue at the position in a TNF mutant corresponding to position 32 in SEQ ID NO: 15 or position 52 of SEQ ID NO: 17 is shown herein to affect protein yield on expression in a recombinant system. For example, the presence of W at this position leads to substantially no expression in a recombinant system and the presence of A at this position leads to unexpectedly high yields in a recombinant system.

Human TNFα consists of a 35 amino acid cytoplasmic domain, a 20 amino acid transmembrane domain and a 177 amino acid extracellular domain. The 177 amino acid extracellular domain is cleaved to produce a 157 amino acid soluble form, which is biologically active, and which forms a non-covalently linked trimer in solution. In the context of the present invention, the human TNFα is a mutant of TNFα which is preferably the soluble form of the extracellular domain of human TNFα, or the extracellular domain of human TNFα. The sequence of the soluble form of the extracellular domain of human TNFα is shown in SEQ ID NO: 15 Typically, the mutant TNFα has at least 70%, more preferably one of at least 75%, at least 80%, at least 85%, at least 90%, at least 95%, at least 96%, at least 97%, at least 98%, at least 99% or 100%, sequence identity to the amino acid sequence set forth in SEQ ID NO: 15 with one or more mutations which reduce activity, for example a mutation at the position corresponding to position 32 in SEQ ID NO: 15. The sequence of the extracellular domain of human TNFα is shown in SEQ ID NO: 17. In this case, the mutant TNFα may have at least 70%, more preferably one of at least at least 75%, at least 80%, at least 85%, at least 90%, at least 95%, at least 96%, at least 97%, at least 98%, at least 99% or 100% sequence identity to the amino acid sequence set forth in SEQ ID NO: 17 with one or more mutations which reduce activity, for example a mutation at the position corresponding to position 52 in SEQ ID NO: 17.

The inventors have shown that a conjugate of the present invention, and in particular the TNFα present in a conjugate of the present invention, wherein the arginine residue of TNFα at position 32 of SEQ ID NO: 15 or at position 52 of SEQ ID NO: 17 is substituted with alanine, exhibits reduced activity. Thus, the mutant of TNFα may comprise or consist of the sequence shown in SEQ ID NO: 15 or 17, except that the residue at position 32 of SEQ ID NO: 15 or at position 52 of SEQ ID NO: 17 is an alanine residue rather than an arginine residue. This sequence is shown in SEQ ID NO: 37 or 39. The mutant of TNFα thus preferably comprises or consist of the sequence set forth in SEQ ID NO: 37. Typically, the mutant of TNFα has at least 70%, more preferably one of at least 75%, 80%, 85%, 90%, 95%, 96%, 97%, 98%, 99% or 100%, sequence identity to the amino acid sequence set forth in SEQ ID NO: 37 with an A at the position corresponding to position 32 in SEQ ID NO: 37. Thus, alternatively the TNFα may comprise or consist of the sequence set forth in SEQ ID NO: 39. In this case, the TNFα may have at least 70%, more preferably one of at least 75%, 80%, 85%, 90%, 95%, 96%, 97%, 98%, 99% or 100%, sequence identity to the amino acid sequence set forth in SEQ ID NO: 39 with an A at the position corresponding to position 52 in SEQ ID NO: 39.

Most preferably, the IL2 comprise the sequence set forth in SEQ ID NO: 12 and/or the TNFα comprise the sequence set forth in SEQ ID NO: 37.

Mutants of TNFα proteins may be tested in vivo and in vitro assays. Suitable assays include but are not limited to activity assays and binding assays. The substitution or deletion of arginine residue at position 32 (Arg 32) has been described in the prior art. For example, arginine residue has been proposed to be substituted by serine, glutamine, asparagine, aspartic acid, glutamic acid, histidine, tryptophan, threonine or tyrosine (U.S. Pat. Nos. 7,101,974; 5,422,104; WO1988/006625; Yamagishi et al., Protein Eng. (1990) 3:713-9)). Furthermore, Arg32 has also been proposed to be deleted in EP158286. Mutants wherein Arg 32 has been substituted by tryptophan have shown a loss of cytotoxic activity (Van Ostade et al. The Embo Journal (1991) 10:827-836). Mutants wherein arginine at position 29 and/or 31 and/or 32 is substituted by tryptophan or tyrosine, show a significant difference between binding affinity to the human p75 TNF Receptor and to the human p55-TNF Receptor (U.S. Pat. No. 5,422,104). U.S. Pat. No. 7,101,974 described TNFα variants which interact with the wild-type TNFα to form mixed trimers incapable of activating receptor signalling. In this last example, Arg32 is substituted by aspartic acid, glutamic acid or histidine.

Preferably, the antibody molecule is connected to the IL2 and the TNF mutant, preferably TNFα mutant, through linkers, for example peptide linkers. Alternatively, the antibody molecule and IL2 and/or a mutant of tumour necrosis factor, may be connected directly, e.g. through a chemical bond. Where the antibody molecule is linked to IL2 and a mutant of tumour necrosis factor by means of one or more peptide linkers, the conjugate may be a fusion protein. By "fusion protein" is meant a polypeptide that is a translation product resulting from the fusion of two or more genes or nucleic acid coding sequences into one open reading frame (ORF).

The chemical bond may be, for example, a covalent or ionic bond. Examples of covalent bonds include peptide bonds (amide bonds) and disulphide bonds. The antibody molecule and IL2 and/or TNF mutant, preferably TNFα mutant, may be covalently linked, for example by peptide bonds (amide bonds). Thus, the antibody molecule, in particular a scFv portion of an antibody molecule, and IL2 and/or the TNF mutant, preferably TNFα mutant, may be produced as a fusion protein.

Where the antibody molecule is a two-chain or multi-chain molecule (e.g. a diabody), IL2 and/or the TNF mutant may be conjugated as a fusion protein with one or more polypeptide chains in the antibody molecule.

The peptide linker connecting the antibody molecule and IL2 and/or the TNF mutant, may be a flexible peptide linker. Suitable examples of peptide linker sequences are known in the art. The linker may be 10-20 amino acids, preferably 10-15 amino acids in length. Most preferably, the linker is 11-15 amino acids in length. The linker may have the sequence set forth in SEQ ID NO: 13, SEQ ID NO: 14 or SEQ ID NO: 49. In some preferred embodiments, the IL2 and the TNF mutant may be linked to the antibody molecule by the linkers set forth in SEQ ID NO: 13 and SEQ ID NO: 14, respectively. In other preferred embodiments, the IL2 and the TNF mutant may be linked to the antibody molecule by the linkers set forth in SEQ ID NO: 49 and SEQ ID NO: 14, respectively.

For example, in the conjugates exemplified in Example 2, IL2 was conjugated to the VH domain of the F8 scFv and the TNFα or the TNFα mutant was conjugated to the VL domain of the F8 scFv, each via a peptide linker as shown in SEQ ID NO: 1 and SEQ ID NO: 36 respectively. In the conjugate exemplified in Example 4, IL2 was conjugated to the VH domain of the L19 scFv and the TNFα or the TNFα mutant was conjugated to the VL domain of the L19 scFv, each via a peptide linker as shown in SEQ ID NO: 70 and SEQ ID NO: 44, respectively.

However, it is expected that the conjugate comprising IL2 and a TNF mutant, preferably a TNFα mutant, and an antibody molecule which binds an antigen associated with neoplastic growth and/or angiogenesis would show the same or similar tumour targeting properties, and/or therapeutic efficacy as the tumour necrosis factor and IL2 were conjugated to the antibody molecule. Thus, where the antibody molecule is, or comprises, an scFv, the IL2 may be linked to the N-terminus of the VH domain of the scFv via a peptide linker and the mutant of TNF may be linked to the C-terminus of the VL domain of the scFv via a peptide linker. Alternatively, where the antibody molecule is, or comprises, an scFv, the mutant of TNF may be linked to the N-terminus of the VH domain of the scFv via a peptide linker and the IL2 may be linked to the C-terminus of the VL domain of the scFv via a peptide linker. It is expected that a conjugate would have the same or similar tumour targeting properties, and/or therapeutic efficacy, and/or cell killing activity if both IL2 and a mutant of TNF, preferably TNFα, were conjugated to the VH domain of the antibody. As a further alternative, the IL2 and TNF mutant, preferably TNFα mutant, may therefore be linked to the C-terminus of the VL domain of the antibody, e.g. in scFv format, via a peptide linker. As a yet further alternative the IL2 and TNF mutant, preferably TNFα mutant, may be linked to the N-terminus of the VH domain of the antibody, e.g. in scFv format, via a peptide linker. In the latter two conjugates, the IL2 and TNF may be in any order and/or may optionally be linked to one another via a peptide linker. Suitable peptide linkers are described herein.

Conjugates described herein may comprise or consist of the sequence shown in SEQ ID NO: 36 or may be a variant thereof. A variant may have at least 70%, more preferably at least 75%, at least 80%, at least 85%, at least 90%, at least 95%, at least 96%, at least 97%, at least 98%, or at least 99% sequence identity to the reference sequence e.g. the amino acid sequence shown in SEQ ID NO: 36. Preferably, the residue at the position in the variant corresponding to position 432 of SEQ ID NO: 36 is A. For example, a conjugate that is a variant of SEQ ID NO: 36 may comprise an A residue at position 432.

Alternatively, conjugates described herein may comprise or consist of the sequence shown in SEQ ID NO: 1 with an R to A mutation at position 432 or SEQ ID NO: 16 with an R to A mutation at position 452 or may be a variant of one of these sequences. A variant may have at least 70%, more preferably at least 75%, at least 80%, at least 85%, at least 90%, at least 95%, at least 96%, at least 97%, at least 98%, or at least 99% sequence identity to the reference sequence e.g. the amino acid sequence shown in SEQ ID NO: 1 or SEQ ID NO: 16. Preferably, the residue at the position corresponding to position 432 in a variant of SEQ ID NO: 1 is A and the residue at the position corresponding to position 452 in a variant of SEQ ID NO: 16 is A. For example, a conjugate that is a variant of SEQ ID NO: 1 or SEQ ID NO: 16 may comprise an A residue at position 432 or 452 respectively.

Alternatively, conjugates described herein may comprise or consist of the sequence shown in SEQ ID NO: 38 or may be a variant thereof. A variant may have at least 70%, more preferably at least 75%, at least 80%, at least 85%, at least 90%, at least 95%, at least 96%, at least 97%, at least 98%, or at least 99% sequence identity to the reference sequence e.g. the amino acid sequence shown in SEQ ID NO: 38. Preferably, the residue at the position in the variant corresponding to position 452 of SEQ ID NO: 38 is A. For example, a conjugate that is a variant of SEQ ID NO: 38 may comprise an A residue at position 452.

Alternatively, conjugates described herein may comprise or consist of one of the sequences shown in SEQ ID NOs: 58 to 63 or may be a variant thereof. A variant may have at least 70%, more preferably at least 75%, at least 80%, at least 85%, at least 90%, at least 95%, at least 96%, at least 97%, at least 98%, or at least 99% sequence identity to the reference sequence e.g. one of the amino acid sequences shown in SEQ ID NOs: 58 to 63. Preferably, the residue at the position corresponding to position 432 in a variant of SEQ ID NO: 58, 60, or 62 is W, F, or V, respectively. Preferably, the residue at the position corresponding to position 452 in a variant of SEQ ID NO: 59, 61 or 63 is W, F, or V, respectively.

Alternatively, conjugates described herein may comprise or consist of the sequence shown in SEQ ID NO: 40 or may be a variant thereof. A variant may have at least 70%, more preferably at least 75%, at least 80%, at least 85%, at least 90%, at least 95%, at least 96%, at least 97%, at least 98%, or at least 99% sequence identity to the amino acid sequence shown in SEQ ID NO: 40. Preferably, the residue at the position in the variant corresponding to position 427 of SEQ ID NO: 40 is A. For example, a conjugate that is a variant of SEQ ID NO: 40 may comprise an A residue at position 427.

Alternatively, conjugates described herein may comprise or consist of the sequence shown in SEQ ID NO: 41 or may be a variant thereof. A variant may have at least 70%, more preferably one of at least 75%, 80%, 85%, 90%, 95%, 96%, 97%, 98% or 99% sequence identity to the reference sequence e.g. the amino acid sequence shown in SEQ ID NO: 41. Preferably, the residue at the position in the variant corresponding to position 447 of SEQ ID NO: 41 is A. For example, a conjugate that is a variant of SEQ ID NO: 41 may comprise an A residue at position 447.

Alternatively, conjugates described herein may comprise or consist of the sequence shown in SEQ ID NO: 42 or may be a variant thereof. A variant may have at least 70%, more preferably one of at least 75%, 80%, 85%, 90%, 95%, 96%, 97%, 98% or 99% sequence identity to the amino acid sequence shown in SEQ ID NO: 42. Preferably, the residue at the position in the variant corresponding to position 428 of SEQ ID NO: 42 is A. For example, a conjugate that is a variant of SEQ ID NO: 42 may comprise an A residue at position 428.

Alternatively, conjugates described herein may comprise or consist of the sequence shown in SEQ ID NO: 43 or may be a variant thereof. A variant may have at least 70%, more preferably one of at least 75%, 80%, 85%, 90%, 95%, 96%, 97%, 98% or 99% sequence identity to the amino acid sequence shown in SEQ ID NO: 43. Preferably, the residue at the position in the variant corresponding to position 448 of SEQ ID NO: 43 is A. For example, a conjugate that is a variant of SEQ ID NO: 43 may comprise an A residue at position 448.

Alternatively, conjugates described herein may comprise or consist of the sequence shown in SEQ ID NO: 44 or may be a variant thereof. A variant may have at least 70%, more preferably one of at least 75%, 80%, 85%, 90%, 95%, 96%, 97%, 98% or 99% sequence identity to the amino acid sequence shown in SEQ ID NO: 44. Preferably, the residue at the position in the variant corresponding to position 430 of SEQ ID NO: 44 is A. For example, a conjugate that is a variant of SEQ ID NO: 44 may comprise an A residue at position 430.

Alternatively, conjugates described herein may comprise or consist of the sequence shown in SEQ ID NO: 45 or may be a variant thereof. A variant may have at least 70%, more preferably one of at least 75%, 80%, 85%, 90%, 95%, 96%, 97%, 98% or 99% sequence identity to the amino acid sequence shown in SEQ ID NO: 45. Preferably, the residue at the position in the variant corresponding to position 450 of SEQ ID NO: 45 is A. For example, a conjugate that is a variant of SEQ ID NO: 45 may comprise an A residue at position 450.

Alternatively, conjugates described herein may comprise or consist of the sequence shown in SEQ ID NO: 70 with an R to A mutation at position 430 or SEQ ID NO: 71 with an R to A mutation at position 450 or may be a variant of one of these sequences. A variant may have at least 70%, more preferably at least 75%, at least 80%, at least 85%, at least 90%, at least 95%, at least 96%, at least 97%, at least 98%, or at least 99% sequence identity to the reference sequence e.g. the amino acid sequence shown in SEQ ID NO: 70 or SEQ ID NO: 71.

Preferably, the residue at the position corresponding to position 430 in a variant of SEQ ID NO: 70 is A and the residue at the position corresponding to position 450 in a variant of SEQ ID NO: 71 is A. For example, a conjugate that is a variant of SEQ ID NO: 70 or SEQ ID NO: 71 may comprise an A residue at position 430 or 450 respectively.

Alternatively, conjugates described herein may comprise or consist of the sequences shown in SEQ ID NOs: 64 to 69 or may be a variant thereof. A variant may have at least 70%, more preferably one of at least 75%, 80%, 85%, 90%, 95%, 96%, 97%, 98% or 99% sequence identity to the amino acid sequences shown in SEQ ID NOs: 64 to 69. Preferably, the residue at the position corresponding to position 430 in a variant of SEQ ID NO: 64, 66 or 68 is W, F or V, respectively. Preferably, the residue at the position corresponding to position 450 in a variant of SEQ ID NO: 65, 67 or 69 is W, F or V, respectively.

Alternatively, conjugates described herein may comprise or consist of the sequence shown in SEQ ID NO: 47 or may be a variant thereof. A variant may have at least 70%, more preferably at least 75%, at least 80%, at least 85%, at least 90%, at least 95%, at least 96%, at least 97%, at least 98%, or at least 99% sequence identity to the amino acid sequence shown in SEQ ID NO: 47. Preferably, the residue at the position in the variant corresponding to position 431 of SEQ ID NO: 47 is A. For example, a conjugate that is a variant of SEQ ID NO: 47 may comprise an A residue at position 431.

Alternatively, conjugates described herein may comprise or consist of the sequence shown in SEQ ID NO: 48 or may be a variant thereof. A variant may have at least 70%, more preferably one of at least 75%, 80%, 85%, 90%, 95%, 96%, 97%, 98% or 99% sequence identity to the reference sequence e.g. the amino acid sequence shown in SEQ ID NO: 48. Preferably, the residue at the position in the variant corresponding to position 451 of SEQ ID NO: 48 is A. For example, a conjugate that is a variant of SEQ ID NO: 48 may comprise an A residue at position 451.

Alternatively, conjugates described herein may comprise or consist of the sequences shown in SEQ ID NOs: 72 to 77 or may be a variant thereof. A variant may have at least 70%, more preferably one of at least 75%, 80%, 85%, 90%, 95%, 96%, 97%, 98% or 99% sequence identity to the reference sequence e.g. the amino acid sequences shown in SEQ ID NOs: 72 to 77. Preferably, the residue at the position corresponding to position 431 in a variant of SEQ ID NO: 72, 74 or 76 is W, F, or V, respectively. Preferably, the residue at the position corresponding to position 451 in a variant of SEQ ID NO: 73, 75 or 77 is W, F, or V, respectively.

Without being limited by any theoretical explanation, a conjugate described herein comprising a TNF mutant may form a homotrimer in solution. Such a trimeric conjugate would comprise three molecules of active IL2 to one molecule of active TNF with reduced activity (in trimeric structure). This may be advantageous as IL2-based immunocytokines are typically used in the clinic at higher doses compared to TNFα-based immunocytokines. For example, the recommended dose of L19-IL2 was found to be 4 mg in patients with cancer [Johannsen et al. (2010) *Eur. J. Cancer*], while the recommended dose of L19-TNFα is in the 1-1.5 mg dose range [Spitaleri et al. (2012) *J. Clin. Oncol. Cancer Res.*]. Furthermore, higher doses of the conjugates described herein may be used as the mutant of TNF has a reduced activity, compared to a conjugate comprising a wild type TNF and IL2. Thus, the conjugates described herein may have advantageous properties with respect to administration regimens.

Also provided is an isolated nucleic acid molecule encoding a conjugate as described herein. Nucleic acid molecules may comprise DNA and/or RNA and may be partially or wholly synthetic. Reference to a nucleotide sequence as set out herein encompasses a DNA molecule with the specified sequence, and encompasses a RNA molecule with the specified sequence in which U is substituted for T, unless context requires otherwise.

Further provided are constructs in the form of plasmids, vectors (e.g. expression vectors), transcription or expression cassettes which comprise such nucleic acids. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) Molecular Cloning: a Laboratory Manual: 3rd edition, Cold Spring Harbor Laboratory Press. Many known techniques and protocols for manipulation of nucleic acid, for example in the preparation of nucleic acid constructs, mutagenesis, sequencing, introduction of DNA into cells and gene expression, and analysis of proteins, are described in detail in Ausubel et al. (1999) $4^{th}$ eds., Short Protocols in Molecular Biology: A Compendium of Methods from Current Protocols in Molecular Biology, John Wiley & Sons.

A recombinant host cell that comprises one or more constructs as described above is also provided. Suitable host cells include bacteria, mammalian cells, plant cells, filamentous fungi, yeast and baculovirus systems and transgenic plants and animals.

Conjugates described herein may be produced using such a recombinant host cell. The production method may comprise expressing a nucleic acid or construct as described above. Expression may conveniently be achieved by culturing the recombinant host cell under appropriate conditions for production of the conjugate. Following production the conjugate may be isolated and/or purified using any suitable technique, and then used as appropriate. The conjugate may be formulated into a composition including at least one additional component, such as a pharmaceutically acceptable excipient.

Systems for cloning and expression of a polypeptide in a variety of different host cells are well known. The expression of antibodies, including conjugates thereof, in prokaryotic cells is well established in the art. For a review, see for example Plückthun (1991), Bio/Technology 9: 545-551. A common bacterial host is *E. coli*.

Expression in eukaryotic cells in culture is also available to those skilled in the art as an option for production of conjugates for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

A method comprising introducing a nucleic acid or construct disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The nucleic acid may or construct be integrated into the genome (e.g. chromosome) of the host cell. Integration may be promoted by inclusion of sequences that promote recombination with the genome, in accordance with standard techniques.

The term "isolated" refers to the state in which conjugates described herein, antibodies for use as described herein, or nucleic acid encoding such conjugates, will generally be in accordance with the present invention. Thus, conjugates described herein, antibodies for use as described herein, or nucleic acid encoding such conjugates may be provided in isolated and/or purified, e.g. from the environment in which they are prepared (such as cell culture), in substantially pure or homogeneous form, or, in the case of nucleic acid, free or substantially free of nucleic acid other than the sequence encoding a polypeptide with the required function. Isolated members and isolated nucleic acids will be free or substantially free of material with which they are found in the environment in which they are prepared (e.g. cell culture) when such preparation is by recombinant DNA technology practised in vitro or in vivo. Specific conjugates and nucleic acids may be formulated with diluents or adjuvants and still for practical purposes be isolated—for example the members may be mixed with pharmaceutically acceptable carriers or diluents when used in therapy. Specific conjugates may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations of conjugates may also be used as described herein. For example, such preparations may be mixtures of conjugates comprising antibody molecules with full-length heavy chains and heavy chains lacking the C-terminal lysine, with various degrees of glycosylation and/or with derivatized amino acids, such as cyclization of an N-terminal glutamic acid to form a pyroglutamic acid residue.

Fibronectin is an antigen that is subject to alternative splicing, and a number of alternative isoforms of fibronectin are known, including alternatively spliced isoforms A-FN and B-FN, comprising domains ED-A or ED-B respectively, which are known markers of angiogenesis. An antibody molecule, as referred to herein, may selectively bind to isoforms of fibronectin selectively expressed in the neovasculature. An antibody molecule may bind fibronectin isoform A-FN, e.g. it may bind domain ED-A (extra domain A). An antibody molecule may bind ED-B (extra domain B).

Fibronectin Extra Domain-A (EDA or ED-A) is also known as ED, extra type III repeat A (EIIIA) or EDI. The sequence of human ED-A has been published by Kornblihtt et al. (1984), Nucleic Acids Res. 12, 5853-5868 and Paoella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al. (1987), *J. Cell. Biol.*, 104, 595-600). ED-A is mainly absent in the plasma form of FN but is abundant during embryogenesis, tissue remodelling, fibrosis, cardiac transplantation and solid tumour growth.

Fibronectin isoform B-FN is one of the best known markers angiogenesis (U.S. Ser. No. 10/382,107, WO01/62298). An extra domain "ED-B" of 91 amino acids is found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567, WO2006/050834). An antibody molecule, as referred to herein, may bind tenascin-C. An antibody molecule may bind tenascin-C domain A1.

Cancer, as referred to herein, may be a cancer which expresses, or has been shown to express, an antigen associated with neoplastic growth and/or angiogenesis, such as an extracellular matrix component associated with neoplastic growth and/or angiogenesis. Preferably, the cancer is a cancer which expresses, or has been shown to express, the ED-A isoform of fibronectin, the ED-B isoform of fibronectin and/or alternatively spliced tenascin C. More preferably the cancer expresses the ED-A isoform of fibronectin. For example, the cancer may be any type of solid or non-solid cancer or malignant lymphoma. The cancer may be selected from the group consisting of skin cancer (in particular melanoma), head and neck cancer, kidney cancer, sarcoma, germ cell cancer (such as teratocarcinoma), liver cancer, lymphoma (such as Hodgkin's or non-Hodgkin's lymphoma), leukaemia (e.g. acute myeloid leukaemia), skin cancer, bladder cancer, breast cancer, uterine cancer, ovarian cancer, prostate cancer, lung cancer, colorectal cancer, cervical cancer, oesophageal cancer, pancreatic cancer, stomach cancer, and cerebral cancer. Cancers may be familial or sporadic. Cancers may be metastatic or non-metastatic. Preferably, the cancer is a cancer selected from the group consisting of a melanoma, head and neck cancer, kidney cancer, and a sarcoma. The reference to a cancer as mentioned above normally refers to a malignant transformation of the cells in question. Thus, kidney cancer, for example, refers to a malignant transformation of cells in the kidney. The cancer may be located at its primary location, such as the kidney in the case of kidney cancer, or at a distant location in the case of metastases. A tumour as referred to herein may be the result of any of the cancers mentioned above. Preferably, a tumour is the result of a melanoma, head and neck cancer, kidney cancer, or a sarcoma. A tumour which is the result of a particular cancer includes both a primary tumour and tumour metastases of said cancer. Thus, a tumour which is the result of head and neck cancer, for example, includes both a primary tumour of head and neck and cancer and metastases of head and neck cancer found in other parts of a patient's body.

Conjugates described herein may have anti-tumour activity and thus find application in cancer treatment. Without being limited by any theoretical explanation, it is expected that the conjugates will show potent anti-tumour activity as a result of excellent tumour targeting properties, as demonstrated in Examples 3 and 4 below. The conjugates described herein are thus designed to be used in methods of treatment of patients, preferably human patients. Conjugates of the present invention may in particular be used in the treatment of cancer.

Accordingly, the invention provides methods of treatment comprising administration of a conjugate described above, pharmaceutical compositions comprising such conjugates, and use of such conjugates in the manufacture of a medicament for administration, for example in a method of making a medicament or pharmaceutical composition comprising formulating the conjugate with a pharmaceutically acceptable excipient. Pharmaceutically acceptable vehicles are well known and will be adapted by the person skilled in the art as a function of the nature and of the mode of administration of the active compound(s) chosen.

Conjugates described herein will usually be administered in the form of a pharmaceutical composition, which may comprise at least one component in addition to the antibody molecule. Thus, pharmaceutical compositions described herein, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous, intratumoral or subcutaneous. Preferably, the conjugate of the present invention is administered intratumorally.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising a conjugate described herein may be administered alone or in combination with other cancer treatments, concurrently or sequentially or as a combined preparation with another therapeutic agent or agents, for the treatment of cancer. For example, a conjugate of the invention may be used in combination with an existing therapeutic agent for cancer.

A conjugate described herein may be used in the manufacture of a medicament. The medicament may be for separate or combined administration to an individual, and accordingly may comprise the conjugate and the additional component as a combined preparation or as separate preparations. Separate preparations may be used to facilitate separate and sequential or simultaneous administration, and allow administration of the components by different routes.

Compositions provided may be administered to mammals, preferably humans. Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of conjugate, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of a conjugate for use as described herein can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the conjugate. A typical conjugate dose will be in the range 10 µg to 500 µg/kg for systemic applications. An initial higher loading dose, followed by one or more lower doses, may be administered. This is a dose for a single treatment of an adult patient, which may be proportionally adjusted for children and infants, and also adjusted according to conjugate format in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety for all purposes.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1—Production and Analysis of huIL2-F8-huTNFα Conjugate, huIL2-F8-huTNFα Mutant Conjugates, huIL2-L19-huTNFα Conjugate and huIL2-L19-huTNFα Mutant Conjugate Various conjugates with human TNF α mutants were prepared and characterised by FPLC, SDS-PAGE and MS. The results are summarized in Table 1. Little or no expression of the R32W mutant was observed in either the IL2-L19-TNFα or the IL2-F8-TNFα immunocytokines. Yields of the R32A mutant were unexpectedly high for both immunocytokines.

TABLE 1

| | Protein | Mutation | Dialysis Buffer | Yield (mg/L) | FPLC Profile | SDS-PAGE | MS | SEQ ID NO |
|---|---|---|---|---|---|---|---|---|
| 1 | IL2-L19-TNF α | - | PBS | 1.6 | ✓ | ✓ | ✓ | 70 |
| 2 | IL2-L19-TNF α | R32W | PBS | 0.4 | ✓ | ✓ | ✓ | 64 |
| 3 | IL2-L19-TNF α | R32A | PBS | 2.2 | ✓ | ✓ | ✓ | 44 |
| 4 | IL2-F8-TNF α | - | PBS | 1.4 | ✓ | ✓ | ✓ | 1 |
| 5 | IL2-F8-TNF α | R32W | PBS | - | x | x | x | 58 |
| 6 | IL2-F8-TNF α | R32A | PBS | 3.4 | ✓ | ✓ | ✓ | 36 |

TABLE 1-continued

| | Protein | Mutation | Dialysis Buffer | Yield (mg/L) | FPLC Profile | SDS-PAGE | MS | SEQ ID NO |
|---|---|---|---|---|---|---|---|---|
| 7 | IL2-F8-TNF α | R32F | MES | 1.9 | ✓ | ✓ | ✓ | 60 |
| 8 | IL2-F8-TNF α | R32V | MES | 3.2 | ✓ | ✓ | ✓ | 62 |

Example 2—Effect of Conjugate Format on Cell Killing Activity

The fusion proteins could be expressed and purified to homogeneity. The purified huIL2-F8-huTNFα conjugate (SEQ ID NO: 1) and huIL2-F8-huTNFα (R32A) mutant conjugate (SEQ ID NO: 36) were analysed by routine experiment on an ÄKTA-FPLC system with a Superdex 200 HR 10/30 column and characterized by SDS-PAGE analysis under non-reducing and reducing conditions.

To test the significance of the TNFα mutation in the conjugate on cell killing activity, the activity of the two fusion proteins was tested in a cell killing assay employing the L M fibroblast cell line. The assay was performed in the presence of 2 μg/mL actinomycin D (Sigma-Aldrich). Cells were seeded in 96-well plates in the culture medium supplemented with increasing concentrations of huIL2-F8-huTNFα (SEQ ID NO: 1), or huIL2-F8-huTNFα (R32A) (SEQ ID NO: 36) as indicated in FIG. 1. The F8 antibody was in scFv format in all of the conjugates tested. The results are shown in FIG. 1. Results are expressed as the percentage of cell viability compared to cells treated with actinomycin D only (used as the negative control). The results demonstrate that the cell killing activity of the huIL2-F8-huTNFα (R32A) mutant conjugate was lower compared to the huIL2-F8-huTNFα conjugate, as can be seen from the EC50 values reported in FIG. 1. The EC50 value represents the drug concentration required for half-maximal activity.

Figure 2:
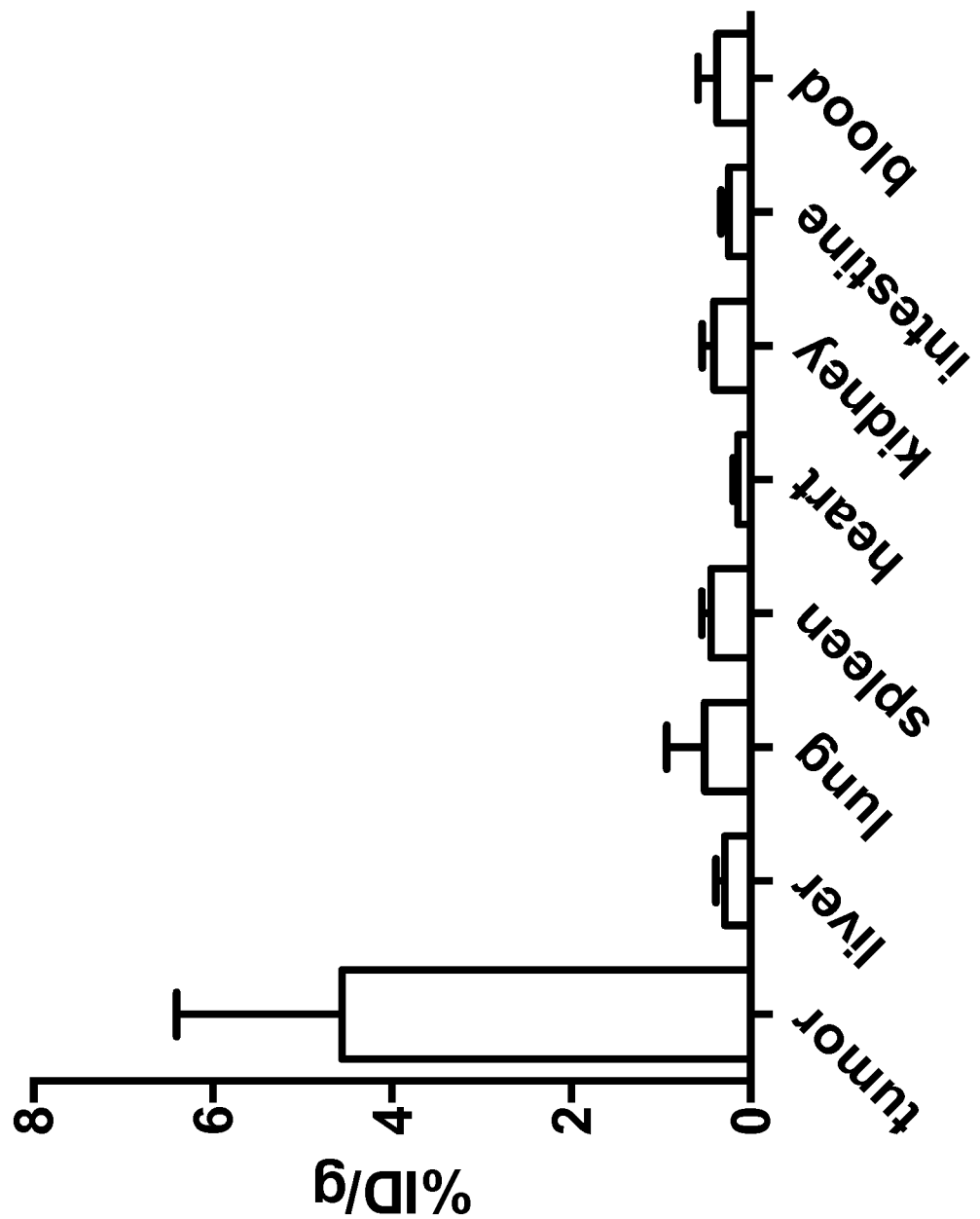

Example 3—Biodistribution Analysis of huIL2-F8-huTNF (R32A) Mutant Conjugate The in vivo targeting performance of huIL2-F8-huTNF (R32A) mutant conjugate was evaluated by biodistribution analysis. The fusion protein was purified over size exclusion chromatography and then radioiodinated with Iodine 125. A total of 12 μg (~9.6 μCi) of the fusion protein preparation were injected into the tail vein of immunocompetent 129Sv mice bearing subcutaneously implanted F9 murine teratocarcinomas. Mice were sacrificed 24 h after injection. Organs were weighed and radioactivity was counted with a Packard Cobra gamma counter. The radioactive content of representative organs was recorded and expressed as percentage injected dose over gram of tissue (% ID/g). The results show a preferential and selective accumulation of huIL2-F8-huTNFα (R32A) mutant conjugate in the tumour (FIG. 2).

Example 4—Production and Analysis of huIL2-L19-huTNFα (R32A) Mutant Conjugates Protein Characterization The fusion protein huIL2-L19-huTNFα (R32A) (SEQ ID NO: 44) was purified from the cell culture medium to homogeneity by protein A chromatography and analysed by SDS-PAGE, ESI-MS and size exclusion chromatography (Superdex200 10/300GL, GE Healthcare).

The biological activity of TNF and IL2 was determined on HT1080 and CTLL2 cells, respectively.

Figure 3:
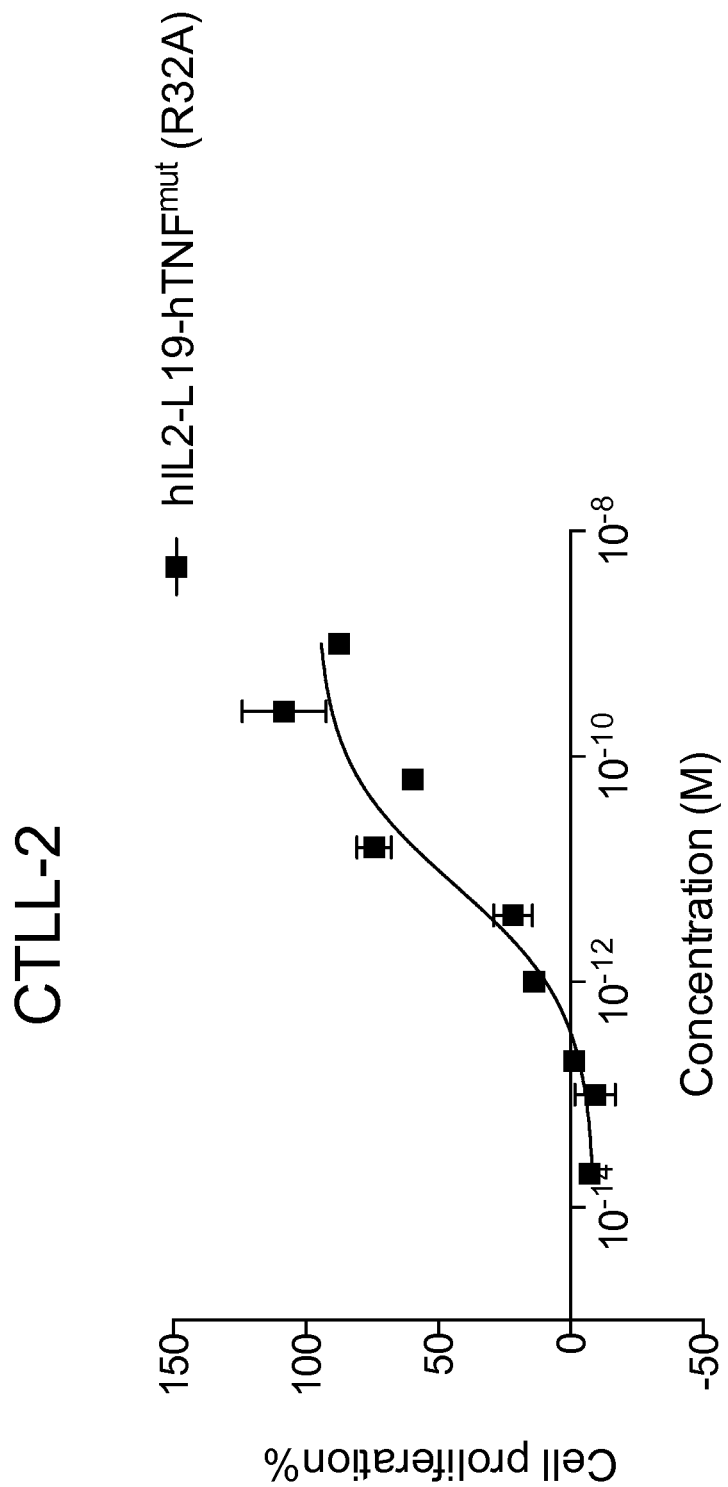
Figure 4:
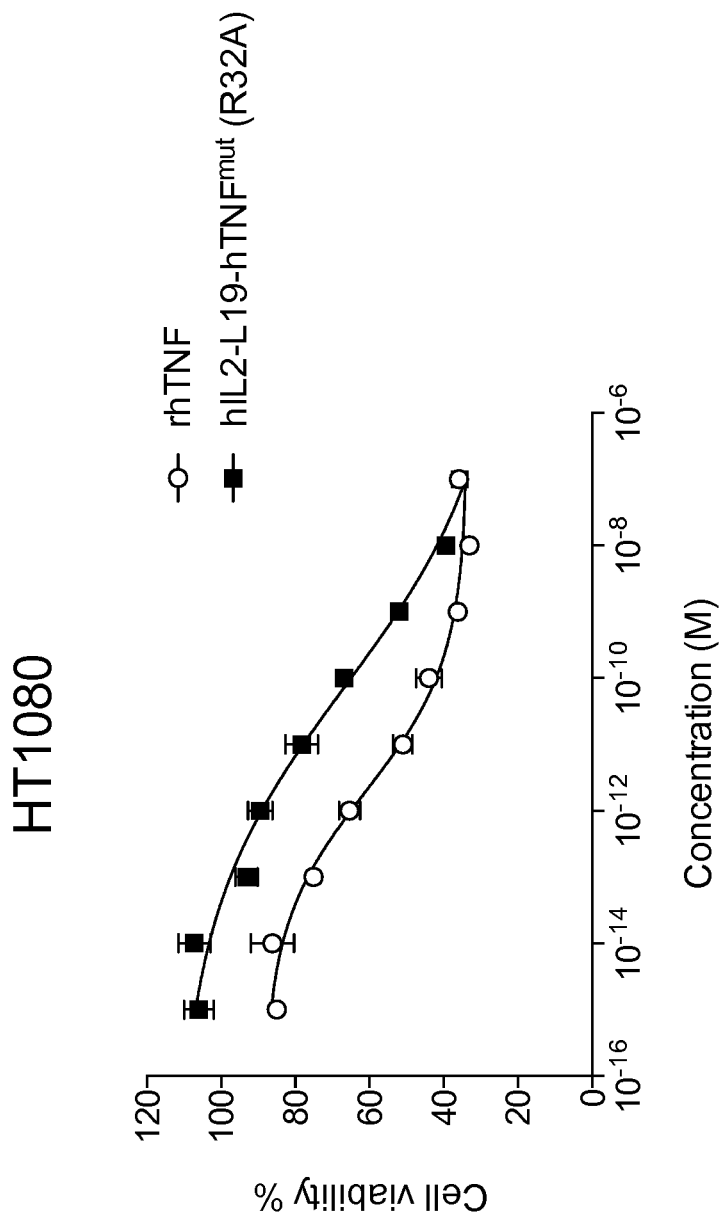

The huIL2-L19-huTNFα (R32A) mutant conjugate was well-behaved in biochemical assays, selectively localized to solid tumours in vivo and displayed a matched in vitro activity of the IL2 and TNF moieties, using cellular assays based on the proliferation of murine CTLL-2 lymphocytes (FIG. 3) and on the killing of human HT-1080 tumour cell line (FIG. 4).

Biodistribution Studies

Figure 5:
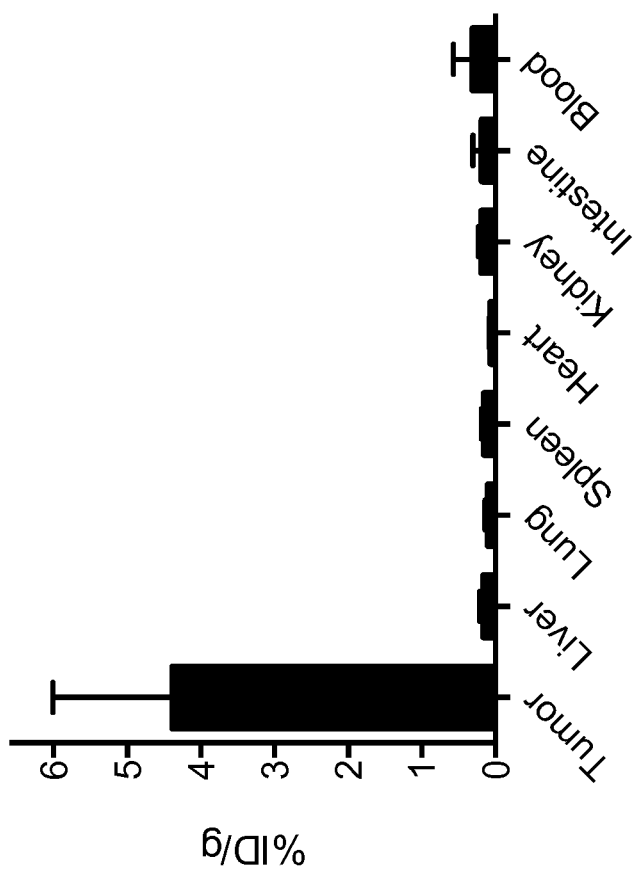

The in vivo EDB targeting performance of huIL2-L19-huTNF (R32A) mutant conjugate was evaluated by biodistribution analysis. 10 μg of radioiodinated fusion protein was injected into the lateral tail vein of F9 tumour-bearing mice. Mice were sacrificed 24 h after injection, organs were excised, weighed and the radioactivity of organs and tumours was measured using a Cobra γ counter and expressed as percentage of injected dose per gram of tissue (% ID/g±SEM), (n=3 mice per group). The results show a preferential and selective accumulation of huIL2-L19-huTNFα (R32A) mutant conjugate in the tumour (FIG. 5).

SEQUENCE LISTING

1. Amino Acid Sequence of the huIL2-F8-huTNFα [Soluble Form] Conjugate (SEQ ID NO: 1)

The amino acid sequence of the huIL2-F8-huTNFα [soluble form] conjugate (human IL2-linker-F8 VH-linker-F8 VL-linker-human TNFα [soluble form]) is shown below. The linker sequences are underlined. The human TNFα in this conjugate is the soluble form of the extracellular domain of TNFα.

```
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGDGSSGGSGGASEVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSSGGGGSGGGGSGGGGEIVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIKSSSSGSSSSGSSSSG

VRSSSRTPSDKPVAHVVANPQAEGQLQWLNRRANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL
```

2. Amino Acid Sequence of the F8 VH Domain (SEQ ID NO: 2)

```
EVQLLESGGGLVQPGGSLRLSCAASGFTFSLFTMSWVRQAPGKGLEWVSAI

SGSGGSTYYADSVKGRFTISRDNSKNTLYLQMNSLRAEDTAVYYCAKSTHL

YLFDYWGQGTLVTVSS
```

3. Amino Acid Sequence of the Linker Linking the VH Domain to the -VL Domain of the Antibody (SEQ ID NO: 3)

```
GGGGSGGGGSGGGG
```

4. Amino Acid Sequence of the F8 VL Domain (SEQ ID NO: 4)

```
EIVLTQSPGTLSLSPGERATLSCRASQSVSMPFLAWYQQKPGQAPRLLIY
GASSRATGIPDRFSGSGSGTDFTLTISRLEPEDFAVYYCQQMRGRPPTFG
QGTKVEIK
```

5. Amino Acid Sequence of the F8 scFv (SEQ ID NO: 5)

```
EVQLLESGGGLVQPGGSLRLSCAASGFTFSLFTMSWVRQAPGKGLEWVSA
ISGSGGSTYYADSVKGRFTISRDNSKNTLYLQMNSLRAEDTAVYYCAKST
HLYLFDYWGQGTLVTVSSGGGGSGGGGSGGGGEIVLTQSPGTLSLSPGER
ATLSCRASQSVSMPFLAWYQQKPGQAPRLLIYGASSRATGIPDRFSGSGS
GTDFTLTISRLEPEDFAVYYCQQMRGRPPTFGQGTKVEIK
```

6. Amino Acid Sequences of the F8 CDR's

```
                        (SEQ ID NO: 6)
F8 CDR1 VH - LFT (SEQ ID NO: 7)
F8 CDR2 VH - SGSGGS (SEQ ID NO: 8)
F8 CDR3 VH - STHLYL (SEQ ID NO: 9)
F8 CDR1 VL - MPF (SEQ ID NO: 10)
F8 CDR2 VL - GASSRAT (SEQ ID NO: 11)
F8 CDR3 VL - MRGRPP
```

7. Amino Acid Sequence of Human IL2 (huIL2) in the Conjugates (SEQ ID NO: 12)

```
APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT
```

8. Amino Acid Sequence of the Linker Linking the Antibody Molecule and IL2 and/or the TNF Mutant (SEQ ID NO: 13)

```
GDGSSGGSGGAS
```

9. Amino Acid Sequence of the Linker Linking the Antibody Molecule and IL2 and/or the TNF Mutant (SEQ ID NO: 14)

```
SSSSGSSSSGSSSSG
```

10. Amino Acid Sequence of the Soluble Form of the Extracellular Domain of Human TNFα (huTNFα) (SEQ ID NO: 15)

```
VRSSSRTPSDKPVAHVVANPQAEGQLQWLNRRANALLANGVELRDNQLVV
PSEGLYLIYSQVLFKGQGCPSTHVLLTHTISRIAVSYQTKVNLLSAIKSP
CQRETPEGAEAKPWYEPIYLGGVFQLEKGDRLSAEINRPDYLDFAESGQV
YFGIIAL
```

11. Amino Acid Sequence of the huIL2-F8-huTNFα [Extracellular Domain] Conjugate (SEQ ID NO: 16)

The amino acid sequence of the huIL2-F8-huTNFα [extracellular domain] conjugate (human IL2-linker-F8 VH-linker-F8 VL-linker-human TNFα [extracellular domain]) is shown below. The linker sequences are underlined. The human TNFα in this conjugate is the extracellular domain of TNFα.

```
APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLTGDGSSGGSGGASEVQLL
ESGGGLVQPGGSLRLSCAASGFTFSLFTMSWVRQAPGKGLEWVSAISGSG
GSTYYADSVKGRFTISRDNSKNTLYLQMNSLRAEDTAVYYCAKSTHLYLF
DYWGQGTLVTVSSGGGGSGGGGSGGGGEIVLTQSPGTLSLSPGERATLSC
RASQSVSMPFLAWYQQKPGQAPRLLIYGASSRATGIPDRFSGSGSGTDFT
LTISRLEPEDFAVYYCQQMRGRPPTFGQGTKVEIKSSSSGSSSSGSSSSG
GPQREEFPRDLSLISPLAQAVRSSSRTPSDKPVAHVVANPQAEGQLQWLN
RRANALLANGVELRDNQLVVPSEGLYLIYSQVLFKGQGCPSTHVLLTHTI
SRIAVSYQTKVNLLSAIKSPCQRETPEGAEAKPWYEPIYLGGVFQLEKGD
RLSAEINRPDYLDFAESGQVYFGIIAL
```

12. Amino Acid Sequence of the Extracellular Domain of Human TNFα (huTNFα) (SEQ ID NO:17)

```
GPQREEFPRDLSLISPLAQAVRSSSRTPSDKPVAHVVANPQAEGQLQWLNR
RANALLANGVELRDNQLVVPSEGLYLIYSQVLFKGQGCPSTHVLLTHTISR
IAVSYQTKVNLLSAIKSPCQRETPEGAEAKPWYEPIYLGGVFQLEKGDRLS
AEINRPDYLDFAESGQVYFGIIAL
```

13. Amino Acid Sequence of L19 CDR's

```
L19 CDR1 VH
                                     (SEQ ID NO: 18)
Ser Phe Ser Met Ser

L19 CDR2 VH
                                     (SEQ ID NO: 19)
Ser Ile Ser Gly Ser Ser Gly Thr Thr Tyr Tyr
Ala Asp Ser Val Lys Gly

L19 CDR3 VH
                                     (SEQ ID NO: 20)
Pro Phe Pro Tyr Phe Asp Tyr

L19 CDR1 VL
                                     (SEQ ID NO: 21)
Arg Ala Ser Gln Ser Val Ser Ser Ser Phe Leu Ala
```

```
L19 CDR2 VL
                                           (SEQ ID NO: 22)
Tyr Ala Ser Ser Arg Ala Thr

L19 CDR3 VL
                                           (SEQ ID NO: 23)
Gln Gln Thr Gly Arg Ile Pro Pro Thr
```

14. Amino Acid Sequence of L19 VH Domain (SEQ ID NO: 24)

```
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Ser Phe Ser Met Ser Trp
Val Arg Gln Ala Pro Gly Lys Gly Leu Glu Trp Val
Ser Ser Ile Ser Gly Ser Ser Gly Thr Thr Tyr Tyr
Ala Asp Ser Val Lys Gly Arg Phe Thr Ile Ser Arg
Asp Asn Ser Lys Asn Thr Leu Tyr Leu Gln Met Asn
Ser Leu Arg Ala Glu Asp Thr Ala Val Tyr Tyr Cys
Ala Lys Pro Phe Pro Tyr Phe Asp Tyr Trp Gly Gln
Gly Thr Leu Val Thr Val Ser Ser
```

15. Amino Acid Sequence of L19 VL Domain (SEQ ID NO: 25)

```
Glu Ile Val Leu Thr Gln Ser Pro Gly Thr Leu Ser
Leu Ser Pro Gly Glu Arg Ala Thr Leu Ser Cys Arg
Ala Ser Gln Ser Val Ser Ser Ser Phe Leu Ala Trp
Tyr Gln Gln Lys Pro Gly Gln Ala Pro Arg Leu Leu
Ile Tyr Tyr Ala Ser Ser Arg Ala Thr Gly Ile Pro
Asp Arg Phe Ser Gly Ser Gly Ser Gly Thr Asp Phe
Thr Leu Thr Ile Ser Arg Leu Glu Pro Glu Asp Phe
Ala Val Tyr Tyr Cys Gln Gln Thr Gly Arg Ile Pro
Pro Thr Phe Gly Gln Gly Thr Lys Val Glu Ile Lys
```

16. Amino Acid Sequence of scFv(L19) (SEQ ID NO: 26)

```
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Ser Phe Ser Met Ser Trp
Val Arg Gln Ala Pro Gly Lys Gly Leu Glu Trp Val
Ser Ser Ile Ser Gly Ser Ser Gly Thr Thr Tyr Tyr
Ala Asp Ser Val Lys Gly Arg Phe Thr Ile Ser Arg
Asp Asn Ser Lys Asn Thr Leu Tyr Leu Gln Met Asn
Ser Leu Arg Ala Glu Asp Thr Ala Val Tyr Tyr Cys
Ala Lys Pro Phe Pro Tyr Phe Asp Tyr Trp Gly Gln
Gly Thr Leu Val Thr Val Ser Ser Gly Asp Gly Ser
Ser Gly Gly Ser Gly Gly Ala Ser Glu Ile Val Leu
Thr Gln Ser Pro Gly Thr Leu Ser Leu Ser Pro Gly
Glu Arg Ala Thr Leu Ser Cys Arg Ala Ser Gln Ser
Val Ser Ser Ser Phe Leu Ala Trp Tyr Gln Gln Lys
Pro Gly Gln Ala Pro Arg Leu Leu Ile Tyr Tyr Ala
Ser Ser Arg Ala Thr Gly Ile Pro Asp Arg Phe Ser
Gly Ser Gly Ser Gly Thr Asp Phe Thr Leu Thr Ile
Ser Arg Leu Glu Pro Glu Asp Phe Ala Val Tyr Tyr
Cys Gln Gln Thr Gly Arg Ile Pro Pro Thr Phe Gly
Gln Gly Thr Lys Val Glu Ile Lys
```

17. Amino Acid Sequence of F16 CDR's

```
                                           (SEQ ID NO: 27)
   F16 CDR1 VH - RYGMS (SEQ ID NO: 28)
   F16 CDR2 VH - AISGSGGSTYYADSVKG (SEQ ID NO: 29)
   F16 CDR3 VH - AHNAFDY (SEQ ID NO: 30)
   F16 CDR1 VL - QGDSLRSYYAS (SEQ ID NO: 31)
   F16 CDR2 VL - GKNNRPS (SEQ ID NO: 32)
   F16 CDR3 VL - NSSVYTMPPVV
```

18. Amino Acid Sequence F16 VH Domain (SEQ ID NO: 33)

EVQLLESGGGLVQPGGSLRLSCAASGFTFSRYGMSWVRQAPGKGLEWVSA
ISGSGGSTYYADSVKGRFTISRDNSKNTLYLQMNSLRAEDTAVYYCAKAH
NAFDYWGQGTLVTVSR

19. Amino Acid Sequence F16 VL Domain (SEQ ID NO: 34)

SSELTQDPAVSVALGQTVRITCQGDSLRSYYASWYQQKPGQAPVLVIYGK
NNRPSGIPDRFSGSSSGNTASLTITGAQAEDEADYYCNSSVYTMPPVVFG
GGTKLTVLG

20. Amino Acid Sequence of the scFv(F16) (SEQ ID NO: 35)

The VH and VL domain linker sequence is shown underlined

EVQLLESGGGLVQPGGSLRLSCAASGFTFSRYGMSWVRQAPGKGLEWVSA
ISGSGGSTYYADSVKGRFTISRDNSKNTLYLQMNSLRAEDTAVYYCAKAH
NAFDYWGQGTLVTVSR<u>GGGSGGGSGGS</u>SELTQDPAVSVALGQTVRITCQG
DSLRSYYASWYQQKPGQAPVLVIYGKNNRPSGIPDRFSGSSSGNTASLTI
TGAQAEDEADYYCNSSVYTMPPVVFGGGTKLTVLG

21. Amino Acid Sequence of the huIL2-F8-huTNFα (R32A) Mutant [Soluble Form] Conjugate (SEQ ID NO: 36)

The amino acid sequence of the huIL2-F8-huTNFα (R32A) mutant [soluble form] conjugate (human IL2-linker-F8 VH-linker-F8 VL-linker-human TNFα (R32A) mutant [soluble form]) is shown below. The linker sequences are underlined and the R32A is underlined in bold. The mutant of human TNFα (R32A) in this conjugate is the soluble form of the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GDGSSGGSGGAS</u>EVQLL
ESGGGLVQPGGSLRLSCAASGFTFSLFTMSWVRQAPGKGLEWVSAISGSG
GSTYYADSVKGRFTISRDNSKNTLYLQMNSLRAEDTAVYYCAKSTHLYLF
DYWGQGTLVTVSS<u>GGGGSGGGGSGGGG</u>EIVLTQSPGTLSLSPGERATLSC
RASQSVSMPFLAWYQQKPGQAPRLLIYGASSRATGIPDRFSGSGSGTDFT
LTISRLEPEDFAVYYCQQMRGRPPTFGQGTKVEIK<u>SSSSGSSSSGSSSSG</u>
VRSSSRTPSDKPVAHVVANPQAEGQLQWLNRAANALLANGVELRDNQLVV
PSEGLYLIYSQVLFKGQGCPSTHVLLTHTISRIAVSYQTKVNLLSAIKSP
CQRETPEGAEAKPWYEPIYLGGVFQLEKGDRLSAEINRPDYLDFAESGQV
YFGIIAL

22. Amino Acid Sequence of the Soluble Form of the Extracellular Domain of Human TNFα (R32A) Mutant (huTNFα R32A) (SEQ ID NO: 37). The R32A is Underlined in Bold.

VRSSSRTPSDKPVAHVVANPQAEGQLQWLNRAANALLANGVELRDNQLVV
PSEGLYLIYSQVLFKGQGCPSTHVLLTHTISRIAVSYQTKVNLLSAIKSP
CQRETPEGAEAKPWYEPIYLGGVFQLEKGDRLSAEINRPDYLDFAESGQV
YFGIIAL

23. Amino Acid Sequence of the huIL2-F8-huTNFα (R52A) Mutant (huTNFα R52A) [Extracellular Domain] Conjugate (SEQ ID NO: 38)

The amino acid sequence of the huIL2-F8-huTNFα (R52A) mutant [extracellular domain] conjugate (human IL2-linker-F8 VH-linker-F8 VL-linker-human TNFα (R52A) mutant [extracellular domain]) is shown below. The linker sequences are underlined and the R52A is in underlined in bold. The human TNFα (R52A) mutant in this conjugate is the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GDGSSGGSGGAS</u>EVQLL
ESGGGLVQPGGSLRLSCAASGFTFSLFTMSWVRQAPGKGLEWVSAISGSG
GSTYYADSVKGRFTISRDNSKNTLYLQMNSLRAEDTAVYYCAKSTHLYLF
DYWGQGTLVTVSS<u>GGGGSGGGGSGGGG</u>EIVLTQSPGTLSLSPGERATLSC
RASQSVSMPFLAWYQQKPGQAPRLLIYGASSRATGIPDRFSGSGSGTDFT
LTISRLEPEDFAVYYCQQMRGRPPTFGQGTKVEIK<u>SSSSGSSSSGSSSSG</u>
GPQREEFPRDLSLISPLAQAVRSSSRTPSDKPVAHVVANPQAEGQLQWLN
RAANALLANGVELRDNQLVVPSEGLYLIYSQVLFKGQGCPSTHVLLTHTI
SRIAVSYQTKVNLLSAIKSPCQRETPEGAEAKPWYEPIYLGGVFQLEKGD
RLSAEINRPDYLDFAESGQVYFGIIAL

24. Amino Acid Sequence of the Extracellular Domain of Human TNFα (R52A) Mutant (huTNFα R52A) [Extracellular Domain] (SEQ ID NO: 39). R52A is Underlined in Bold.

GPQREEFPRDLSLISPLAQAVRSSSRTPSDKPVAHVVANPQAEGQLQWLN
RAANALLANGVELRDNQLVVPSEGLYLIYSQVLFKGQGCPSTHVLLTHTI
SRIAVSYQTKVNLLSAIKSPCQRETPEGAEAKPWYEPIYLGGVFQLEKGD
RLSAEINRPDYLDFAESGQVYFGIIAL

25. Amino Acid Sequence of the huIL2-F16-huTNFα (R32A) Mutant [Soluble Form] Conjugate (SEQ ID NO: 40)

The amino acid sequence of the huIL2-F16-huTNFα (R32A) mutant [soluble form] conjugate (human IL2-linker-F16 VH-linker-F16 VL-linker-human TNFα (R32A) mutant [soluble form]) is shown below. The linker sequences are underlined and the R32A is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GDGSSGGSGGAS</u>EVQLL
ESGGGLVQPGGSLRLSCAASGFTFSRYGMSWVRQAPGKGLEWVSAISGSG
GSTYYADSVKGRFTISRDNSKNTLYLQMNSLRAEDTAVYYCAKAHNAFDY
WGQGTLVTVSR<u>GGGSGGGSGGSS</u>ELTQDPAVSVALGQTVRITCQGDSLRS
YYASWYQQKPGQAPVLVIYGKNNRPSGIPDRFSGSSSGNTASLTITGAQA
EDEADYYCNSSVYTMPPVVFGGGTKLTVLG<u>SSSSGSSSSGSSSSG</u>VRSSS
RTPSDKPVAHVVANPQAEGQLQWLNRAANALLANGVELRDNQLVVPSEGL
YLIYSQVLFKGQGCPSTHVLLTHTISRIAVSYQTKVNLLSAIKSPCQRET
PEGAEAKPWYEPIYLGGVFQLEKGDRLSAEINRPDYLDFAESGQVYFGII
AL

26. Amino Acid Sequence of the huIL2-F16-huTNFα (R52A) Mutant [Extracellular Domain] Conjugate (SEQ ID NO: 41)

The amino acid sequence of the huIL2-F16-huTNFα (R52A) mutant [extracellular domain] conjugate (human IL2-linker-F16 VH-linker-F16 VL-linker-human TNFα (R52A) mutant) is shown below. The linker sequences are underlined and the R52A is underlined in bold. The human TNFα mutant in this conjugate is the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSRGGGSGGGSGGSSELTQDPAVSVALGQTVRITCQGDSLRS

YYASWYQQKPGQAPVLVIYGKNNRPSGIPDRFSGSSSGNTASLTITGAQA

EDEADYYCNSSVYTMPPVVFGGGTKLTVLGSSSSGSSSSGSSSSGGPQRE

EFPRDLSLISPLAQAVRSSSRTPSDKPVAHVVANPQAEGQLQWLNRAANA

LLANGVELRDNQLVVPSEGLYLIYSQVLFKGQGCPSTHVLLTHTISRIAV

SYQTKVNLLSAIKSPCQRETPEGAEAKPWYEPIYLGGVFQLEKGDRLSAE

INRPDYLDFAESGQVYFGIIAL

27. Amino Acid Sequence of the huIL2-L19-huTNFα (R32A) Mutant [Soluble Form] Conjugate (SEQ ID NO: 42)

The amino acid sequence of the huIL2-L19-huTNFα (R32A) mutant [soluble form] conjugate (human IL2-linker-L19 VH-linker-L19 VL-linker-human TNFα (R32A) mutant [soluble form]) is shown below. The linker sequences are underlined and the R32A is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGDGSSGGSGGASEVQLL

ESGGGLVQPGGSLRLSCAASGFTFSSFSMSWVRQAPGKGLEWVSSISGSS

GTTYYADSVKGRFTISRDNSKNTLYLQMNSLRAEDTAVYYCAKPFPYFDY

WGQGTLVTVSSGDGSSGGSGGASEIVLTQSPGTLSLSPGERATLSCRASQ

SVSSSYLAWYQQKPGQAPRLLIYYASSRATGIPDRFSGSGSGTDFTLTIS

RLEPEDFAVYYCQQTGRIPPTFGQGTKVEIKSSSSGSSSSGSSSSGVRSS

SRTPSDKPVAHVVANPQAEGQLQWLNRAANALLANGVELRDNQLVVPSEG

LYLIYSQVLFKGQGCPSTHVLLTHTISRIAVSYQTKVNLLSAIKSPCQRE

TPEGAEAKPWYEPIYLGGVFQLEKGDRLSAEINRPDYLDFAESGQVYFGI

IAL

28. Amino Acid Sequence of the huIL2-L19-huTNFα (R52A) Mutant [Extracellular Domain] Conjugate (SEQ ID NO: 43)

The amino acid sequence of the huIL2-L19-huTNFα (R52A) mutant [extracellular domain] conjugate (human IL2-linker-L19 VH-linker-L19 VL-linker-human TNFα (R52A) mutant) is shown below. The linker sequences are underlined and the R52A is underlined in bold. The human TNFα mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGDGSSGGSGGASEVQLL

ESGGGLVQPGGSLRLSCAASGFTFSSFSMSWVRQAPGKGLEWVSSISGSS

GTTYYADSVKGRFTISRDNSKNTLYLQMNSLRAEDTAVYYCAKPFPYFDY

WGQGTLVTVSSGDGSSGGSGGASEIVLTQSPGTLSLSPGERATLSCRASQ

SVSSSYLAWYQQKPGQAPRLLIYYASSRATGIPDRFSGSGSGTDFTLTIS

RLEPEDFAVYYCQQTGRIPPTFGQGTKVEIKSSSSGSSSSGSSSSGPQR

EEFPRDLSLISPLAQAVRSSSRTPSDKPVAHVVANPQAEGQLQWLNRAAN

ALLANGVELRDNQLVVPSEGLYLIYSQVLFKGQGCPSTHVLLTHTISRIA

VSYQTKVNLLSAIKSPCQRETPEGAEAKPWYEPIYLGGVFQLEKGDRLSA

EINRPDYLDFAESGQVYFGIIAL

29. Amino Acid Sequence of the huIL2-L19-huTNFα (R32A) Mutant [Soluble Form] Conjugate (SEQ ID NO: 44)

The amino acid sequence of the huIL2-L19-huTNFα (R32A) mutant [soluble form] conjugate (human IL2-linker-L19 VH-linker-L19 VL-linker-human TNFα (R32A) mutant [soluble form]) is shown below. The linker sequences are underlined and the R32A is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGGGGSGGGGSGGGGEVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSSGDGSSGGSGGASEIVLTQSPGTLSLSPGERATLSCRA

SQSVSSSFLAWYQQKPGQAPRLLIYYASSRATGIPDRFSGSGSGTDFTLT

ISRLEPEDFAVYYCQQTGRIPPTFGQGTKVEIKSSSSGSSSSGSSSSGVR

SSSRTPSDKPVAHVVANPQAEGQLQWLNRAANALLANGVELRDNQLVVPS

EGLYLIYSQVLFKGQGCPSTHVLLTHTISRIAVSYQTKVNLLSAIKSPCQ

RETPEGAEAKPWYEPIYLGGVFQLEKGDRLSAEINRPDYLDFAESGQVYF

GIIAL

30. Amino Acid Sequence of the huIL2-L19-huTNFα (R52A) Mutant [Extracellular Domain] Conjugate (SEQ ID NO: 45)

The amino acid sequence of the huIL2-L19-huTNFα (R52A) mutant [extracellular domain] conjugate (human IL2-linker-L19 VH-linker-L19 VL-linker-human TNFα (R52A) mutant) is shown below. The linker sequences are underlined and the R52A is underlined in bold. The human TNFα mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGGGGSGGGGSGGGGEVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSSGDGSSGGSGGASEIVLTQSPGTLSLSPGERATLSCRA

SQSVSSSFLAWYQQKPGQAPRLLIYYASSRATGIPDRFSGSGSGTDFTLT

```
ISRLEPEDFAVYYCQQTGRIPPTFGQGTKVEIKSSSSGSSSSGSSSSGGP

QREEFPRDLSLISPLAQAVRSSSRTPSDKPVAHVVANPQAEGQLQWLNRA

ANALLANGVELRDNQLVVPSEGLYLIYSQVLFKGQGCPSTHVLLTHTISR

IAVSYQTKVNLLSAIKSPCQRETPEGAEAKPWYEPIYLGGVFQLEKGDRL

SAEINRPDYLDFAESGQVYFGIIAL
```

31. Amino Acid Sequence of the scFv(F16) (SEQ ID NO: 46)

The VH and VL domain linker sequence is shown underlined

```
EVQLLESGGGLVQPGGSLRLSCAASGFTFSRYGMSWVRQAPGKGLEWVSA

ISGSGGSTYYADSVKGRFTISRDNSKNTLYLQMNSLRAEDTAVYYCAKAH

NAFDYWGQGTLVTVSRGGGGSGGGGSGGGGSSELTQDPAVSVALGQTVRI

TCQGDSLRSYYASWYQQKPGQAPVLVIYGKNNRPSGIPDRFSGSSSGNTA

SLTITGAQAEDEADYYCNSSVYTMPPVVFGGGTKLTVLG
```

32. Amino Acid Sequence of the huIL2-F16-huTNFα (R32A) Mutant [Soluble Form] Conjugate (SEQ ID NO: 47)

The amino acid sequence of the huIL2-F16-huTNFα (R32A) mutant [soluble form] conjugate (human IL2-linker-F16 VH-linker-F16 VL-linker-human TNFα (R32A) mutant [soluble form]) is shown below. The linker sequences are underlined and the R32A is underlined in bold. The human TNFα mutant in this conjugate is the soluble form of the extracellular domain of TNFα.

```
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGDSSGGSGGASEVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLGSSSSGSSSSGSSSSGV

RSSSRTPSDKPVAHVVANPQAEGQLQWLNRAANALLANGVELRDNQLVVP

SEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVY

FGIIAL
```

33. Amino Acid Sequence of the huIL2-F16-huTNFα (R52A) Mutant [Extracellular Domain] Conjugate (SEQ ID NO: 48)

The amino acid sequence of the huIL2-F16-huTNFα (R52A) mutant [extracellular domain] conjugate (human IL2-linker-F16 VH-linker-F16 VL-linker-human TNFα (R52A) mutant) is shown below. The linker sequences are underlined and the R52A is underlined in bold. The human TNFα mutant in this conjugate is the extracellular domain of TNFα.

```
APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTGDSSGGSGGASEVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLGSSSSGSSSSGSSSSGG

PQREEFPRDLSLISPLAQAVRSSSRTPSDKPVAHVVANPQAEGQLQWLNR

AANALLANGVELRDNQLVVPSEGLYLIYSQVLFKGQGCPSTHVLLTHTIS

RIAVSYQTKVNLLSAIKSPCQRETPEGAEAKPWYEPIYLGGVFQLEKGDR

LSAEINRPDYLDFAESGQVYFGIIAL
```

34. Amino Acid Sequence of the Linker Linking the Antibody Molecule and IL2 and/or the TNF Mutant (SEQ ID NO: 49)

```
GGGGSGGGGSGGGG
```

35. Amino Acid Sequence of the Linker Linking the VH Domain to the VL Domain of the Antibody (SEQ ID NO: 50)

```
GDGSSGGSGGAS
```

36. Amino Acid Sequence of the Linker Linking the VH Domain to the VL Domain of the Antibody (SEQ ID NO: 51)

```
GGGSGGGSGG
```

37. Amino Acid Sequence of the Soluble Form of the Extracellular Domain of Human TNFα (R32W) Mutant (huTNFα R32W) (SEQ ID NO: 52). The R32W is Underlined in Bold.

```
VRSSSRTPSDKPVAHVVANPQAEGQLQWLNRWANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL
```

38. Amino Acid Sequence of the Extracellular Domain of Human TNFα (R52W) Mutant (huTNFα R52W) (SEQ ID NO: 53). R52W is Underlined in Bold.

```
GPQREEFPRDLSLISPLAQAVRSSSRTPSDKPVAHVVANPQAEGQLQWLN

RWANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL
```

39. Amino Acid Sequence of the Soluble Form of the Extracellular Domain of Human TNFα (R32F) Mutant (huTNFα R32F) (SEQ ID NO: 54). The R32F is Underlined in Bold.

VRSSSRTPSDKPVAHVVANPQAEGQLQWLNRFANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

40. Amino Acid Sequence of the Extracellular Domain of Human TNFα (R52F) Mutant (huTNFα R52F) (SEQ ID NO: 55). R52F is Underlined in Bold.

GPQREEFPRDLSLISPLAQAVRSSSRTPSDKPVAHVVANPQAEGQLQWLN

RFANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL

41. Amino Acid Sequence of the Soluble Form of the Extracellular Domain of Human TNFα (R32V) Mutant (huTNFα R32V) (SEQ ID NO: 56). The R32V is Underlined in Bold.

VRSSSRTPSDKPVAHVVANPQAEGQLQWLNRVANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

42. Amino Acid Sequence of the Extracellular Domain of Human TNFα (R52V) Mutant (huTNFα R52V) (SEQ ID NO: 57). R52V is in Underlined in Bold.

GPQREEFPRDLSLISPLAQAVRSSSRTPSDKPVAHVVANPQAEGQLQWLN

RVANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL

43. Amino Acid Sequence of the huIL2-F8-huTNFα (R32W) Mutant [Soluble Form] Conjugate (SEQ ID NO: 58)

The amino acid sequence of the huIL2-F8-huTNFα (R32W) mutant [soluble form] conjugate (human IL2-linker-F8 VH-linker-F8 VL-linker-human TNFα (R32W) mutant [soluble form]) is shown below. The linker sequences are underlined and the R32W is underlined in bold. The mutant of human TNFα (R32W) in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGGE</u>IVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

VRSSSRTPSDKPVAHVVANPQAEGQLQWLNRWANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

44. Amino Acid Sequence of the huIL2-F8-huTNFα (R52W) Mutant (huTNFα R52W) [Extracellular Domain] Conjugate (SEQ ID NO: 59)

The amino acid sequence of the huIL2-F8-huTNFα (R52W) mutant [extracellular domain] conjugate (human IL2-linker-F8 VH-linker-F8 VL-linker-human TNFα (R52W) mutant [extracellular domain]) is shown below. The linker sequences are underlined and the R52W is underlined in bold. The human TNFα (R52W) mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGGE</u>IVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

GPQREEFPRDLSLISPLAQAVRSSSRTPSDKPVAHVVANPQAEGQLQWLN

RWANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL

45. Amino Acid Sequence of the huIL2-F8-huTNFα (R32F) Mutant [Soluble Form] Conjugate (SEQ ID NO: 60)

The amino acid sequence of the huIL2-F8-huTNFα (R32F) mutant [soluble form] conjugate (human IL2-linker-F8 VH-linker-F8 VL-linker-human TNFα (R32F) mutant [soluble form]) is shown below. The linker sequences are underlined and the R32F is underlined in bold. The mutant of human TNFα (R32F) in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGGE</u>IVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

VRSSSRTPSDKPVAHVVANPQAEGQLQWLNRFANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

46. Amino Acid Sequence of the huIL2-F8-huTNFα (R52F) Mutant (huTNFα R52F) [Extracellular Domain] Conjugate (SEQ ID NO: 61)

The amino acid sequence of the huIL2-F8-huTNFα (R52F) mutant [extracellular domain] conjugate (human IL2-linker-F8 VH-linker-F8 VL-linker-human TNFα (R52F) mutant [extracellular domain]) is shown below. The linker sequences are underlined and the R52F is underlined in bold. The human TNFα (R52F) mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGG</u>EIVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

GPQREEFPRDLSLISPLAQAVRSSSRTPSDKPVAHVVANPQAEGQLQWLN

RFANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL

47. Amino Acid Sequence of the huIL2-F8-huTNFα (R32V) Mutant [Soluble Form] Conjugate (SEQ ID NO: 62)

The amino acid sequence of the huIL2-F8-huTNFα (R32V) mutant [soluble form] conjugate (human IL2-linker-F8 VH-linker-F8 VL-linker-human TNFα (R32V) mutant [soluble form]) is shown below. The linker sequences are underlined and the R32V is underlined in bold. The mutant of human TNFα (R32V) in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGG</u>EIVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

VRSSSRTPSDKPVAHVVANPQAEGQLQWLNRVANALLANGVELRDNQLVV

PSEGLYLIYSQVLFKGQGCPSTHVLLTHTISRIAVSYQTKVNLLSAIKSP

CQRETPEGAEAKPWYEPIYLGGVFQLEKGDRLSAEINRPDYLDFAESGQV

YFGIIAL

48. Amino Acid Sequence of the huIL2-F8-huTNFα (R52V) Mutant (huTNFα R52V) [Extracellular Domain]. Conjugate (SEQ ID NO: 63)

The amino acid sequence of the huIL2-F8-huTNFα (R52V) mutant [extracellular domain] conjugate (human IL2-linker-F8 VH-linker-F8 VL-linker-human TNFα (R52V) mutant [extracellular domain]) is shown below. The linker sequences are underlined and the R52V is underlined in bold. The human TNFα (R52V) mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSLFTMSWVRQAPGKGLEWVSAISGSG

GSTYYADSVKGRFTISRDNSKNTLYLQMNSLRAEDTAVYYCAKSTHLYLF

DYWGQGTLVTVSS<u>GGGGSGGGGSGGGG</u>EIVLTQSPGTLSLSPGERATLSC

RASQSVSMPFLAWYQQKPGQAPRLLIYGASSRATGIPDRFSGSGSGTDFT

LTISRLEPEDFAVYYCQQMRGRPPTFGQGTKVEIK<u>SSSSGSSSSGSSSSG</u>

GPQREEFPRDLSLISPLAQAVRSSSRTPSDKPVAHVVANPQAEGQLQWLN

RVANALLANGVELRDNQLVVPSEGLYLIYSQVLFKGQGCPSTHVLLTHTI

SRIAVSYQTKVNLLSAIKSPCQRETPEGAEAKPWYEPIYLGGVFQLEKGD

RLSAEINRPDYLDFAESGQVYFGIIAL

49. Amino Acid Sequence of the huIL2-L19-huTNFα (R32W) Mutant [Soluble Form] Conjugate (SEQ ID NO: 64)

The amino acid sequence of the huIL2-L19-huTNFα (R32W) mutant [soluble form] conjugate (human IL2-linker-L19 VH-linker-L19 VL-linker-human TNFα (R32W) mutant [soluble form]) is shown below. The linker sequences are underlined and the R32W is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GGGGSGGGGSGGGG</u>EVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSS<u>GDGSSGGSGGAS</u>EIVLTQSPGTLSLSPGERATLSCRA

SQSVSSSFLAWYQQKPGQAPRLLIYYASSRATGIPDRFSGSGSGTDFTLT

ISRLEPEDFAVYYCQQTGRIPPTFGQGTKVEIK<u>SSSSGSSSSGSSSSG</u>VR

SSSRTPSDKPVAHVVANPQAEGQLQWLNR<u>W</u>ANALLANGVELRDNQLVVPS

EGLYLIYSQVLFKGQGCPSTHVLLTHTISRIAVSYQTKVNLLSAIKSPCQ

RETPEGAEAKPWYEPIYLGGVFQLEKGDRLSAEINRPDYLDFAESGQVYF

GIIAL

50. Amino Acid Sequence of the huIL2-L19-huTNFα (R52W) Mutant [Extracellular Domain] Conjugate (SEQ ID NO: 65)

The amino acid sequence of the huIL2-L19-huTNFα (R52W) mutant [extracellular domain] conjugate (human IL2-linker-L19 VH-linker-L19 VL-linker-human TNFα (R52W) mutant) is shown below. The linker sequences are underlined and the R52W is underlined in bold. The human TNFα mutant in this conjugate is the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GGGGSGGGGSGGGG</u>EVQ
LLESGGGLVQPGGSLRLSCAASGFTFSSFSMSWVRQAPGKGLEWVSSISG
SSGTTYYADSVKGRFTISRDNSKNTLYLQMNSLRAEDTAVYYCAKPFPYF
DYWGQGTLVTVSS<u>GDGSSGGSGGAS</u>EIVLTQSPGTLSLSPGERATLSCRA
SQSVSSSFLAWYQQKPGQAPRLLIYYASSRATGIPDRFSGSGSGTDFTLT
ISRLEPEDFAVYYCQQTGRIPPTFGQGTKVEIK<u>SSSSGSSSSGSSSSGGP</u>
QREEFPRDLSLISPLAQAVRSSSRTPSDKPVAHVVANPQAEGQLQWLNRW
ANALLANGVELRDNQLVVPSEGLYLIYSQVLFKGQGCPSTHVLLTHTISR
IAVSYQTKVNLLSAIKSPCQRETPEGAEAKPWYEPIYLGGVFQLEKGDRL
SAEINRPDYLDFAESGQVYFGIIAL

51. Amino Acid Sequence of the huIL2-L19-huTNFα (R32F) Mutant [Soluble Form] Conjugate (SEQ ID NO: 66)

The amino acid sequence of the huIL2-L19-huTNFα (R32F) mutant [soluble form] conjugate (human IL2-linker-L19 VH-linker-L19 VL-linker-human TNFα (R32F) mutant [soluble form]) is shown below. The linker sequences are underlined and the R32F is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GGGGSGGGGSGGGG</u>EVQ
LLESGGGLVQPGGSLRLSCAASGFTFSSFSMSWVRQAPGKGLEWVSSISG
SSGTTYYADSVKGRFTISRDNSKNTLYLQMNSLRAEDTAVYYCAKPFPYF
DYWGQGTLVTVSS<u>GDGSSGGSGGAS</u>EIVLTQSPGTLSLSPGERATLSCRA
SQSVSSSFLAWYQQKPGQAPRLLIYYASSRATGIPDRFSGSGSGTDFTLT
ISRLEPEDFAVYYCQQTGRIPPTFGQGTKVEIK<u>SSSSGSSSSGSSSSG</u>VR
SSSRTPSDKPVAHVVANPQAEGQLQWLNRFANALLANGVELRDNQLVVPS
EGLYLIYSQVLFKGQGCPSTHVLLTHTISRIAVSYQTKVNLLSAIKSPCQ
RETPEGAEAKPWYEPIYLGGVFQLEKGDRLSAEINRPDYLDFAESGQVYF
GIIAL

52. Amino Acid Sequence of the huIL2-L19-huTNFα (R52F) Mutant [Extracellular Domain] Conjugate (SEQ ID NO: 67)

The amino acid sequence of the huIL2-L19-huTNFα (R52F) mutant [extracellular domain] conjugate (human IL2-linker-L19 VH-linker-L19 VL-linker-human TNFα (R52F) mutant) is shown below. The linker sequences are underlined and the R52F is underlined in bold. The human TNFα mutant in this conjugate is the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GGGGSGGGGSGGGG</u>EVQ
LLESGGGLVQPGGSLRLSCAASGFTFSSFSMSWVRQAPGKGLEWVSSISG
SSGTTYYADSVKGRFTISRDNSKNTLYLQMNSLRAEDTAVYYCAKPFPYF
DYWGQGTLVTVSS<u>GDGSSGGSGGAS</u>EIVLTQSPGTLSLSPGERATLSCRA
SQSVSSSFLAWYQQKPGQAPRLLIYYASSRATGIPDRFSGSGSGTDFTLT
ISRLEPEDFAVYYCQQTGRIPPTFGQGTKVEIK<u>SSSSGSSSSGSSSS</u>GGP
QREEFPRDLSLISPLAQAVRSSSRTPSDKPVAHVVANPQAEGQLQWLNRF
ANALLANGVELRDNQLVVPSEGLYLIYSQVLFKGQGCPSTHVLLTHTISR
IAVSYQTKVNLLSAIKSPCQRETPEGAEAKPWYEPIYLGGVFQLEKGDRL
SAEINRPDYLDFAESGQVYFGIIAL

53. Amino Acid Sequence of the huIL2-L19-huTNFα (R32V) Mutant [Soluble Form] Conjugate (SEQ ID NO: 68)

The amino acid sequence of the huIL2-L19-huTNFα (R32V) mutant [soluble form] conjugate (human IL2-linker-L19 VH-linker-L19 VL-linker-human TNFα (R32V) mutant [soluble form]) is shown below. The linker sequences are underlined and the R32V is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT<u>GGGGSGGGGSGGGG</u>EVQ
LLESGGGLVQPGGSLRLSCAASGFTFSSFSMSWVRQAPGKGLEWVSSISG
SSGTTYYADSVKGRFTISRDNSKNTLYLQMNSLRAEDTAVYYCAKPFPYF
DYWGQGTLVTVSS<u>GDGSSGGSGGAS</u>EIVLTQSPGTLSLSPGERATLSCRA
SQSVSSSFLAWYQQKPGQAPRLLIYYASSRATGIPDRFSGSGSGTDFTLT
ISRLEPEDFAVYYCQQTGRIPPTFGQGTKVEIK<u>SSSSGSSSSGSSSSG</u>VR
SSSRTPSDKPVAHVVANPQAEGQLQWLNRVANALLANGVELRDNQLVVPS
EGLYLIYSQVLFKGQGCPSTHVLLTHTISRIAVSYQTKVNLLSAIKSPCQ
RETPEGAEAKPWYEPIYLGGVFQLEKGDRLSAEINRPDYLDFAESGQVYF
GIIAL

54. Amino Acid Sequence of the huIL2-L19-huTNFα (R52V) Mutant [Extracellular Domain] Conjugate (SEQ ID NO: 69)

The amino acid sequence of the huIL2-L19-huTNFα (R52V) mutant [extracellular domain] conjugate (human IL2-linker-L19 VH-linker-L19 VL-linker-human TNFα (R52V) mutant) is shown below. The linker sequences are underlined and the R52V is underlined in bold. The human TNFα mutant in this conjugate is the extracellular domain of TNFα.

APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE

-continued
TTFMCEYADETATIVEFLNRWITFCQSIISTLT<u>GGGGSGGGGSGGGG</u>EVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSS<u>GDGSSGGSGGAS</u>EIVLTQSPGTLSLSPGERATLSCRA

SQSVSSSFLAWYQQKPGQAPRLLIYYASSRATGIPDRFSGSGSGTDFTLT

ISRLEPEDFAVYYCQQTGRIPPTFGQGTKVEIK<u>SSSSGSSSSGSSSS</u>GGP

QREEFPRDLSLISPLAQAVRSSSRTPSDKPVAHVVANPQAEGQLQWLNRV

ANALLANGVELRDNQLVVPSEGLYLIYSQVLFKGQGCPSTHVLLTHTISR

IAVSYQTKVNLLSAIKSPCQRETPEGAEAKPWYEPIYLGGVFQLEKGDRL

SAEINRPDYLDFAESGQVYFGIIAL

55. Amino Acid Sequence of the huIL2-L19-huTNFα [Soluble Form] Conjugate (SEQ ID NO: 70)

The amino acid sequence of the huIL2-L19-huTNFα [soluble form] conjugate (human IL2-linker-L19 VH-linker-L19 VL-linker-human TNFα [soluble form]) is shown below. The linker sequences are underlined. The human TNFα in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GGGGSGGGGSGGGG</u>EVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSS<u>GDGSSGGSGGAS</u>EIVLTQSPGTLSLSPGERATLSCRA

SQSVSSSFLAWYQQKPGQAPRLLIYYASSRATGIPDRFSGSGSGTDFTLT

ISRLEPEDFAVYYCQQTGRIPPTFGQGTKVEIK<u>SSSSGSSSSGSSSS</u>GVR

SSSRTPSDKPVAHVVANPQAEGQLQWLNRRANALLANGVELRDNQLVVPS

EGLYLIYSQVLFKGQGCPSTHVLLTHTISRIAVSYQTKVNLLSAIKSPCQ

RETPEGAEAKPWYEPIYLGGVFQLEKGDRLSAEINRPDYLDFAESGQVYF

GIIAL

56. Amino Acid Sequence of the huIL2-L19-huTNFα [Extracellular Domain] Conjugate (SEQ ID NO: 71)

The amino acid sequence of the huIL2-L19-huTNFα [extracellular domain] conjugate (human IL2-linker-L19 VH-linker-L19 VL-linker-human TNFα) is shown below. The linker sequences are underlined. The human TNFα in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GGGGSGGGGSGGGG</u>EVQ

LLESGGGLVQPGGSLRLSCAASGFTFSSFSMSWVRQAPGKGLEWVSSISG

SSGTTYYADSVKGRFTISRDNSKNTLYLQMNSLRAEDTAVYYCAKPFPYF

DYWGQGTLVTVSS<u>GDGSSGGSGGAS</u>EIVLTQSPGTLSLSPGERATLSCRA

SQSVSSSFLAWYQQKPGQAPRLLIYYASSRATGIPDRFSGSGSGTDFTLT

ISRLEPEDFAVYYCQQTGRIPPTFGQGTKVEIK<u>SSSSGSSSSGSSSS</u>GGP

QREEFPRDLSLISPLAQAVRSSSRTPSDKPVAHVVANPQAEGQLQWLNRR

ANALLANGVELRDNQLVVPSEGLYLIYSQVLFKGQGCPSTHVLLTHTISR

IAVSYQTKVNLLSAIKSPCQRETPEGAEAKPWYEPIYLGGVFQLEKGDRL

SAEINRPDYLDFAESGQVYFGIIAL

57. Amino Acid Sequence of the huIL2-F16-huTNFα (R32W) Mutant [Soluble Form] Conjugate (SEQ ID NO: 72)

The amino acid sequence of the huIL2-F16-huTNFα (R32W) mutant [soluble form] conjugate (human IL2-linker-F16 VH-linker-F16 VL-linker-human TNFα (R32W) mutant [soluble form]) is shown below. The linker sequences are underlined and the R32W is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSS</u>GV

RSSSRTPSDKPVAHVVANPQAEGQLQWLNRWANALLANGVELRDNQLVVP

SEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVY

FGIIAL

58. Amino Acid Sequence of the huIL2-F16-huTNFα (R52W) Mutant [Extracellular Domain] Conjugate (SEQ ID NO: 73)

The amino acid sequence of the huIL2-F16-huTNFα (R52W) mutant [extracellular domain] conjugate (human IL2-linker-F16 VH-linker-F16 VL-linker-human TNFα (R52W) mutant) is shown below. The linker sequences are underlined and the R52W is underlined in bold. The human TNFα mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSS</u>GG

PQREEFPRDLSLISPLAQAVRSSSRTPSDKPVAHVVANPQAEGQLQWLNR

WANALLANGVELRDNQLVVPSEGLYLIYSQVLFKGQGCPSTHVLLTHTIS

RIAVSYQTKVNLLSAIKSPCQRETPEGAEAKPWYEPIYLGGVFQLEKGDR

LSAEINRPDYLDFAESGQVYFGIIAL

59. Amino Acid Sequence of the huIL2-F16-huTNFα (R32F) Mutant [Soluble Form] Conjugate (SEQ ID NO: 74)

The amino acid sequence of the huIL2-F16-huTNFα (R32F) mutant [soluble form] conjugate (human IL2-linker-F16 VH-linker-F16 VL-linker-human TNFα (R32F) mutant [soluble form]) is shown below. The linker sequences are underlined and the R32F is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSSG</u>V

RSSSRTPSDKPVAHVVANPQAEGQLQWLNRFANALLANGVELRDNQLVVP

SEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVY

FGIIAL

60. Amino Acid Sequence of the huIL2-F16-huTNFα (R52F) Mutant [Extracellular Domain] Conjugate (SEQ ID NO: 75)

The amino acid sequence of the huIL2-F16-huTNFα (R52F) mutant [extracellular domain] conjugate (human IL2-linker-F16 VH-linker-F16 VL-linker-human TNFα (R52F) mutant) is shown below. The linker sequences are underlined and the R52F is underlined in bold. The human TNFα mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSSG</u>G

PQREEFPRDLSLISPLAQAVRSSSRTPSDKPVAHVVANPQAEGQLQWLNR

FANALLANGVELRDNQLVVPSEGLYLIYSQVLFKGQGCPSTHVLLTHTIS

RIAVSYQTKVNLLSAIKSPCQRETPEGAEAKPWYEPIYLGGVFQLEKGDR

LSAEINRPDYLDFAESGQVYFGIIAL

61. Amino Acid Sequence of the huIL2-F16-huTNFα (R32V) Mutant [Soluble Form] Conjugate (SEQ ID NO: 76)

The amino acid sequence of the huIL2-F16-huTNFα (R32V) mutant [soluble form] conjugate (human IL2-linker-F16 VH-linker-F16 VL-linker-human TNFα (R32V) mutant [soluble form]) is shown below. The linker sequences are underlined and the R32V is underlined in bold. The human TNFα mutant in this conjugate is the soluble form of the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSSG</u>V

RSSSRTPSDKPVAHVVANPQAEGQLQWLNRVANALLANGVELRDNQLVVP

SEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVY

FGIIAL

62. Amino Acid Sequence of the huIL2-F16-huTNFα (R52V) Mutant [Extracellular Domain] Conjugate (SEQ ID NO: 77)

The amino acid sequence of the huIL2-F16-huTNFα (R52V) mutant [extracellular domain] conjugate (human IL2-linker-F16 VH-linker-F16 VL-linker-human TNFα (R52V) mutant) is shown below. The linker sequences are underlined and the R52V is underlined in bold. The human TNFα mutant in this conjugate is the extracellular domain of TNFα.

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT<u>GDGSSGGSGGAS</u>EVQLL

ESGGGLVQPGGSLRLSCAASGFTFSRYGMSWVRQAPGKGLEWVSAISGSG

GSTYYADSVKGRFTISRDNSKNTLYLQMNSLRAEDTAVYYCAKAHNAFDY

WGQGTLVTVSR<u>GGGGSGGGGSGGGGS</u>SELTQDPAVSVALGQTVRITCQGD

SLRSYYASWYQQKPGQAPVLVIYGKNNRPSGIPDRFSGSSSGNTASLTIT

GAQAEDEADYYCNSSVYTMPPVVFGGGTKLTVLG<u>SSSSGSSSSGSSSSG</u>G

PQREEFPRDLSLISPLAQAVRSSSRTPSDKPVAHVVANPQAEGQLQWLNR

VANALLANGVELRDNQLVVPSEGLYLIYSQVLFKGQGCPSTHVLLTHTIS

RIAVSYQTKVNLLSAIKSPCQRETPEGAEAKPWYEPIYLGGVFQLEKGDR

LSAEINRPDYLDFAESGQVYFGIIAL

The invention claimed is:

1. A fusion protein comprising interleukin-2 (IL2), a human tumour necrosis factor α (TNFα) mutant, and an antibody molecule which binds fibronectin,
wherein the human TNF α mutant has reduced activity relative to the wild type human TNFα and comprises the amino acid sequence of wild-type TNFα with the R at a position corresponding to R32 of SEQ ID NO: 15 or R52 of SEQ ID NO: 17 substituted for A, F, or V; and
wherein the antibody molecule is a single chain Fv (scFv) or a diabody.

2. The fusion protein according to claim 1 wherein the human TNFα mutant has an R to A mutation at said position.

3. The fusion protein according to claim 1 wherein the human TNFα mutant comprises the amino acid sequence of SEQ ID NO: 37 or SEQ ID NO: 39.

4. The fusion protein according to claim 1, wherein the antibody molecule binds the Extra Domain-A (ED-A) of fibronectin.

5. The fusion protein according to claim 4, wherein
(i) the antibody molecule comprises an antigen binding site having the complementarity determining regions (CDRs) of antibody F8 set forth in SEQ ID NOs 6-11;
(ii) the antibody molecule comprises the VH and VL domains of antibody F8 set forth in SEQ ID NOs 2 and 4; and/or
(iii) the antibody molecule comprises the amino acid sequence of scFv F8 set forth in SEQ ID NO: 5.

6. The fusion protein according to claim 1, wherein the antibody molecule is a single chain Fv (scFv) and, wherein
(i) the IL2 is linked to the N-terminus of the VH domain of the scFv via a peptide linker and the TNF mutant is linked to the C-terminus of the VL domain of the scFv via a peptide linker,
(ii) the TNF mutant is linked to the N-terminus of the VH domain of the scFv via a peptide linker and the IL2 is linked to the C-terminus of the VL domain of the scFv via a peptide linker, or
(iii) the IL2 and the TNF mutant are linked to C-terminus of the VL domain of the scFv via a peptide linker or the IL2 and the TNFα are linked to the N-terminus of the scFv via a peptide linker.

7. The fusion protein according to claim 1, wherein
(i) the fusion protein comprises the amino acid sequence of SEQ ID NO: 1 with an R to A mutation at position 432 or the amino acid sequence of SEQ ID NO: 16 with an R to A mutation at position 452; or
(ii) the fusion protein comprises the amino acid sequence of SEQ ID NO: 36 or SEQ ID NO: 38.

8. The fusion protein according to claim 1, wherein
(i) the fusion protein comprises the amino acid sequence of SEQ ID NO: 70 with an R to A mutation at position 430 or the amino acid sequence of SEQ ID NO: 71 with an R to A mutation at position 450 or
(ii) the fusion protein comprises the amino acid sequence of SEQ ID NO: 42, SEQ ID NO: 43, SEQ ID NO: 44, or SEQ ID NO: 45.

9. A nucleic acid molecule encoding a fusion protein according to claim 1 or an expression vector comprising said nucleic acid or a host cell comprising said vector.

10. The fusion protein according to claim 1, wherein the antibody molecule binds the Extra Domain-B (ED-B) of fibronectin.

11. The fusion protein according to claim 10, wherein the antibody molecule comprises at least one of
(i) an antigen binding site having the complementarity determining regions (CDRs) of antibody L19 set forth in SEQ ID NOs 18-23;
(ii) the VH and VL domains of antibody L19 set forth in SEQ ID NOs 24 and 25; and
(iii) the amino acid sequence of scFv L19 set forth in SEQ ID NO: 26.

12. A method of treating cancer by targeting IL2 and TNF to the neovasculature in vivo in a patient, the method comprising administering a therapeutically effective amount of a fusion protein according to claim 1 to the patient.

13. The method according to claim 12, wherein the cancer is a melanoma, head and neck cancer, kidney cancer, or a sarcoma or the tumour is the result of a melanoma, head and neck cancer, kidney cancer, or a sarcoma.

* * * * *

SEQUENCE LISTING

<160> NUMBER OF SEQ ID NOS: 77

<210> SEQ ID NO 1
<211> LENGTH: 557
<212> TYPE: PRT
<213> ORGANISM: Artificial Sequence
<220> FEATURE:
<223> OTHER INFORMATION: Amino acid sequence of the huIL2-F8-huTNFalpha
      [soluble form] conjugate

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Ser Gly Gly Gly Gly
            260                 265                 270

Ser Gly Gly Gly Gly Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln
    290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350
```

```
Ile Ser Arg Leu Glu Pro Glu Asp Phe Ala Val Tyr Tyr Cys Gln Gln
            355                 360                 365

Met Arg Gly Arg Pro Pro Thr Phe Gly Gln Gly Thr Lys Val Glu Ile
370                 375                 380

Lys Ser Ser Ser Gly Ser Ser Ser Gly Ser Ser Ser Ser Ser Ser Gly
385                 390                 395                 400

Val Arg Ser Ser Ser Arg Thr Pro Ser Asp Lys Pro Val Ala His Val
                405                 410                 415

Val Ala Asn Pro Gln Ala Glu Gly Gln Leu Gln Trp Leu Asn Arg Arg
            420                 425                 430

Ala Asn Ala Leu Leu Ala Asn Gly Val Glu Leu Arg Asp Asn Gln Leu
        435                 440                 445

Val Val Pro Ser Glu Gly Leu Tyr Leu Ile Tyr Ser Gln Val Leu Phe
    450                 455                 460

Lys Gly Gln Gly Cys Pro Ser Thr His Val Leu Leu Thr His Thr Ile
465                 470                 475                 480

Ser Arg Ile Ala Val Ser Tyr Gln Thr Lys Val Asn Leu Leu Ser Ala
                485                 490                 495

Ile Lys Ser Pro Cys Gln Arg Glu Thr Pro Glu Gly Ala Glu Ala Lys
            500                 505                 510

Pro Trp Tyr Glu Pro Ile Tyr Leu Gly Gly Val Phe Gln Leu Glu Lys
        515                 520                 525

Gly Asp Arg Leu Ser Ala Glu Ile Asn Arg Pro Asp Tyr Leu Asp Phe
    530                 535                 540

Ala Glu Ser Gly Gln Val Tyr Phe Gly Ile Ile Ala Leu
545                 550                 555

<210> SEQ ID NO 2
<211> LENGTH: 118
<212> TYPE: PRT
<213> ORGANISM: Artificial Sequence
<220> FEATURE:
<223> OTHER INFORMATION: Amino acid sequence of the F8 VH domain

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 3
<211> LENGTH: 14
<212> TYPE: PRT
<213> ORGANISM: Artificial Sequence
<220> FEATURE:
```

```
<223> OTHER INFORMATION: Amino acid sequence of the linker linking the
      VH domain to the -VL domain of the antibody

<400> SEQUENCE: 3

Gly Gly Gly Gly Ser Gly Gly Gly Gly Ser Gly Gly Gly Gly
1               5                   10

<210> SEQ ID NO 4
<211> LENGTH: 108
<212> TYPE: PRT
<213> ORGANISM: Artificial Sequence
<220> FEATURE:
<223> OTHER INFORMATION: Amino acid sequence of the F8 VL domain

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105

<210> SEQ ID NO 5
<211> LENGTH: 240
<212> TYPE: PRT
<213> ORGANISM: Artificial Sequence
<220> FEATURE:
<223> OTHER INFORMATION: Amino acid sequence of the F8 scFv

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160
```

```
Val Ser Met Pro Phe Leu Ala Trp Tyr Gln Gln Lys Pro Gly Gln Ala
            165                 170                 175

Pro Arg Leu Leu Ile Tyr Gly Ala Ser Ser Arg Ala Thr Gly Ile Pro
        180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Met
        210                 215                 220

Arg Gly Arg Pro Pro Thr Phe Gly Gln Gly Thr Lys Val Glu Ile Lys
225                 230                 235                 240

<210> SEQ ID NO 6
<211> LENGTH: 3
<212> TYPE: PRT
<213> ORGANISM: Artificial Sequence
<220> FEATURE:
<223> OTHER INFORMATION: F8 CDR1 VH

<400> SEQUENCE: 6

Leu Phe Thr
1

<210> SEQ ID NO 7
<211> LENGTH: 6
<212> TYPE: PRT
<213> ORGANISM: Artificial Sequence
<220> FEATURE:
<223> OTHER INFORMATION: F8 CDR2 VH

<400> SEQUENCE: 7

Ser Gly Ser Gly Gly Ser
1               5

<210> SEQ ID NO 8
<211> LENGTH: 6
<212> TYPE: PRT
<213> ORGANISM: Artificial Sequence
<220> FEATURE:
<223> OTHER INFORMATION: F8 CDR3 VH

<400> SEQUENCE: 8

Ser Thr His Leu Tyr Leu
1               5

<210> SEQ ID NO 9
<211> LENGTH: 3
<212> TYPE: PRT
<213> ORGANISM: Artificial Sequence
<220> FEATURE:
<223> OTHER INFORMATION: F8 CDR1 VL

<400> SEQUENCE: 9

Met Pro Phe
1

<210> SEQ ID NO 10
<211> LENGTH: 7
<212> TYPE: PRT
<213> ORGANISM: Artificial Sequence
<220> FEATURE:
<223> OTHER INFORMATION: F8 CDR2 VL

<400> SEQUENCE: 10

Gly Ala Ser Ser Arg Ala Thr
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: F8 CDR3 VL

<400> SEQUENCE: 11

Met Arg Gly Arg Pro Pro
1               5

<210> SEQ ID NO 12
<211> LENGTH: 133
<212> TYPE: PRT
<213> ORGANISM: Artificial Sequence
<220> FEATURE:
<223> OTHER INFORMATION: Amino acid sequence of human IL2 (huIL2) in the
      conjugates

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 13
<211> LENGTH: 12
<212> TYPE: PRT
<213> ORGANISM: Artificial Sequence
<220> FEATURE:
<223> OTHER INFORMATION: Amino acid sequence of the linker linking the
      antibody molecule and IL2 and/or the TNF mutant

<400> SEQUENCE: 13

Gly Asp Gly Ser Ser Gly Gly Ser Gly Gly Ala Ser
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Amino acid sequence of the linker linking the
      antibody molecule and IL2 and/or the TNF mutant

<400> SEQUENCE: 14

Ser Ser Ser Ser Gly Ser Ser Ser Gly Ser Ser Ser Gly
1               5                   10                  15
```

-continued

<210> SEQ ID NO 15
<211> LENGTH: 157
<212> TYPE: PRT
<213> ORGANISM: Artificial Sequence
<220> FEATURE:
<223> OTHER INFORMATION: Amino acid sequence of the soluble form of the
      extracellular domain of human TNFalpha (huTNFalpha)

<400> SEQUENCE: 15

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 16
<211> LENGTH: 577
<212> TYPE: PRT
<213> ORGANISM: Artificial Sequence
<220> FEATURE:
<223> OTHER INFORMATION: Amino acid sequence of the huIL2-F8-huTNFalpha
      [extracellular domain] conjugate

<400> SEQUENCE: 16

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
    130                 135                 140

```
Ser Glu Val Gln Leu Leu Glu Ser Gly Gly Leu Val Gln Pro Gly
145                 150                 155                 160

Gly Ser Leu Arg Leu Ser Cys Ala Ala Ser Gly Phe Thr Phe Ser Leu
        165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln
290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
            325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
        355                 360                 365

Met Arg Gly Arg Pro Pro Thr Phe Gly Gln Gly Thr Lys Val Glu Ile
370                 375                 380

Lys Ser Ser Ser Ser Gly Ser Ser Ser Gly Ser Ser Ser Ser Gly
385                 390                 395                 400

Gly Pro Gln Arg Glu Glu Phe Pro Arg Asp Leu Ser Leu Ile Ser Pro
            405                 410                 415

Leu Ala Gln Ala Val Arg Ser Ser Ser Arg Thr Pro Ser Asp Lys Pro
            420                 425                 430

Val Ala His Val Val Ala Asn Pro Gln Ala Glu Gly Gln Leu Gln Trp
            435                 440                 445

Leu Asn Arg Arg Ala Asn Ala Leu Leu Ala Asn Gly Val Glu Leu Arg
        450                 455                 460

Asp Asn Gln Leu Val Val Pro Ser Glu Gly Leu Tyr Leu Ile Tyr Ser
465                 470                 475                 480

Gln Val Leu Phe Lys Gly Gln Gly Cys Pro Ser Thr His Val Leu Leu
            485                 490                 495

Thr His Thr Ile Ser Arg Ile Ala Val Ser Tyr Gln Thr Lys Val Asn
            500                 505                 510

Leu Leu Ser Ala Ile Lys Ser Pro Cys Gln Arg Glu Thr Pro Glu Gly
        515                 520                 525

Ala Glu Ala Lys Pro Trp Tyr Glu Pro Ile Tyr Leu Gly Gly Val Phe
        530                 535                 540

Gln Leu Glu Lys Gly Asp Arg Leu Ser Ala Glu Ile Asn Arg Pro Asp
545                 550                 555                 560
```

```
Tyr Leu Asp Phe Ala Glu Ser Gly Gln Val Tyr Phe Gly Ile Ile Ala
                565                 570                 575
Leu

<210> SEQ ID NO 17
<211> LENGTH: 177
<212> TYPE: PRT
<213> ORGANISM: Artificial Sequence
<220> FEATURE:
<223> OTHER INFORMATION: Amino acid sequence of the extracellular domain
      of human TNFalpha (huTNFalpha)

<400> SEQUENCE: 17

Gly Pro Gln Arg Glu Glu Phe Pro Arg Asp Leu Ser Leu Ile Ser Pro
1               5                  10                   15

Leu Ala Gln Ala Val Arg Ser Ser Ser Arg Thr Pro Ser Asp Lys Pro
                20                 25                   30

Val Ala His Val Val Ala Asn Pro Gln Ala Glu Gly Gln Leu Gln Trp
            35                 40                  45

Leu Asn Arg Arg Ala Asn Ala Leu Leu Ala Asn Gly Val Glu Leu Arg
        50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175
Leu

<210> SEQ ID NO 18
<211> LENGTH: 5
<212> TYPE: PRT
<213> ORGANISM: Artificial Sequence
<220> FEATURE:
<223> OTHER INFORMATION: L19 CDR1 VH

<400> SEQUENCE: 18

Ser Phe Ser Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: L19 CDR2 VH

<400> SEQUENCE: 19

Ser Ile Ser Gly Ser Ser Gly Thr Thr Tyr Tyr Ala Asp Ser Val Lys Gly
1               5                   10                  15

<210> SEQ ID NO 20
```

```
<211> LENGTH: 7
<212> TYPE: PRT
<213> ORGANISM: Artificial Sequence
<220> FEATURE:
<223> OTHER INFORMATION: L19 CDR3 VH

<400> SEQUENCE: 20

Pro Phe Pro Tyr Phe Asp Tyr
1               5

<210> SEQ ID NO 21
<211> LENGTH: 12
<212> TYPE: PRT
<213> ORGANISM: Artificial Sequence
<220> FEATURE:
<223> OTHER INFORMATION: L19 CDR1 VL

<400> SEQUENCE: 21

Arg Ala Ser Gln Ser Val Ser Ser Ser Phe Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: L19 CDR2 VL

<400> SEQUENCE: 22

Tyr Ala Ser Ser Arg Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: L19 CDR3 VL

<400> SEQUENCE: 23

Gln Gln Thr Gly Arg Ile Pro Pro Thr
1               5

<210> SEQ ID NO 24
<211> LENGTH: 116
<212> TYPE: PRT
<213> ORGANISM: Artificial Sequence
<220> FEATURE:
<223> OTHER INFORMATION: Amino acid sequence of L19 VH domain

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
```

```
                    100                 105                 110

Thr Val Ser Ser
            115

<210> SEQ ID NO 25
<211> LENGTH: 108
<212> TYPE: PRT
<213> ORGANISM: Artificial Sequence
<220> FEATURE:
<223> OTHER INFORMATION: Amino acid sequence of L19 VL domain

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 26
<211> LENGTH: 236
<212> TYPE: PRT
<213> ORGANISM: Artificial Sequence
<220> FEATURE:
<223> OTHER INFORMATION: Amino acid sequence of scFv(L19)

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ser Gly Ala Ser
            115                 120                 125

Glu Ile Val Leu Thr Gln Ser Pro Gly Thr Leu Ser Leu Ser Pro Gly
            130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175
```

```
Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
        210                 215                 220

Pro Thr Phe Gly Gln Gly Thr Lys Val Glu Ile Lys
225                 230                 235

<210> SEQ ID NO 27
<211> LENGTH: 5
<212> TYPE: PRT
<213> ORGANISM: Artificial Sequence
<220> FEATURE:
<223> OTHER INFORMATION: F16 CDR1 VH

<400> SEQUENCE: 27

Arg Tyr Gly Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: F16 CDR2 VH

<400> SEQUENCE: 28

Ala Ile Ser Gly Ser Gly Gly Ser Thr Tyr Tyr Ala Asp Ser Val Lys
1               5                   10                  15

Gly

<210> SEQ ID NO 29
<211> LENGTH: 7
<212> TYPE: PRT
<213> ORGANISM: Artificial Sequence
<220> FEATURE:
<223> OTHER INFORMATION: F16 CDR3 VH

<400> SEQUENCE: 29

Ala His Asn Ala Phe Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: F16 CDR1 VL

<400> SEQUENCE: 30

Gln Gly Asp Ser Leu Arg Ser Tyr Tyr Ala Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: F16 CDR2 VL

<400> SEQUENCE: 31

Gly Lys Asn Asn Arg Pro Ser
1               5
```

```
<210> SEQ ID NO 32
<211> LENGTH: 11
<212> TYPE: PRT
<213> ORGANISM: Artificial Sequence
<220> FEATURE:
<223> OTHER INFORMATION: F16 CDR3 VL

<400> SEQUENCE: 32

Asn Ser Ser Val Tyr Thr Met Pro Pro Val Val
1               5                   10

<210> SEQ ID NO 33
<211> LENGTH: 116
<212> TYPE: PRT
<213> ORGANISM: Artificial Sequence
<220> FEATURE:
<223> OTHER INFORMATION: Amino acid sequence F16 VH domain

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 34
<211> LENGTH: 109
<212> TYPE: PRT
<213> ORGANISM: Artificial Sequence
<220> FEATURE:
<223> OTHER INFORMATION: Amino acid sequence F16 VL domain

<400> SEQUENCE: 34

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly
            100                 105
```

```
<210> SEQ ID NO 35
<211> LENGTH: 235
<212> TYPE: PRT
<213> ORGANISM: Artificial Sequence
<220> FEATURE:
<223> OTHER INFORMATION: Amino acid sequence of the scFv(F16)

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Ser Gly Gly Ser Gly Gly Ser Ser
        115                 120                 125

Glu Leu Thr Gln Asp Pro Ala Val Ser Val Ala Leu Gly Gln Thr Val
    130                 135                 140

Arg Ile Thr Cys Gln Gly Asp Ser Leu Arg Ser Tyr Tyr Ala Ser Trp
145                 150                 155                 160

Tyr Gln Gln Lys Pro Gly Gln Ala Pro Val Leu Val Ile Tyr Gly Lys
                165                 170                 175

Asn Asn Arg Pro Ser Gly Ile Pro Asp Arg Phe Ser Gly Ser Ser Ser
            180                 185                 190

Gly Asn Thr Ala Ser Leu Thr Ile Thr Gly Ala Gln Ala Glu Asp Glu
        195                 200                 205

Ala Asp Tyr Tyr Cys Asn Ser Ser Val Tyr Thr Met Pro Pro Val Val
    210                 215                 220

Phe Gly Gly Gly Thr Lys Leu Thr Val Leu Gly
225                 230                 235

<210> SEQ ID NO 36
<211> LENGTH: 557
<212> TYPE: PRT
<213> ORGANISM: Artificial Sequence
<220> FEATURE:
<223> OTHER INFORMATION: Amino acid sequence of the huIL2-F8-huTNFalpha
      (R32A) mutant [soluble form] conjugate

<400> SEQUENCE: 36

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Asp Gly Ser Ser Gly Ser Gly Gly Ala
130                 135                 140
Ser Glu Val Gln Leu Leu Glu Ser Gly Gly Gly Leu Val Gln Pro Gly
145                 150                 155                 160
Gly Ser Leu Arg Leu Ser Cys Ala Ala Ser Gly Phe Thr Phe Ser Leu
                165                 170                 175
Phe Thr Met Ser Trp Val Arg Gln Ala Pro Gly Lys Gly Leu Glu Trp
            180                 185                 190
Val Ser Ala Ile Ser Gly Ser Gly Gly Ser Thr Tyr Tyr Ala Asp Ser
        195                 200                 205
Val Lys Gly Arg Phe Thr Ile Ser Arg Asp Asn Ser Lys Asn Thr Leu
    210                 215                 220
Tyr Leu Gln Met Asn Ser Leu Arg Ala Glu Asp Thr Ala Val Tyr Tyr
225                 230                 235                 240
Cys Ala Lys Ser Thr His Leu Tyr Leu Phe Asp Tyr Trp Gly Gln Gly
                245                 250                 255
Thr Leu Val Thr Val Ser Ser Gly Gly Gly Ser Gly Gly Gly Gly
            260                 265                 270
Ser Gly Gly Gly Gly Glu Ile Val Leu Thr Gln Ser Pro Gly Thr Leu
        275                 280                 285
Ser Leu Ser Pro Gly Glu Arg Ala Thr Leu Ser Cys Arg Ala Ser Gln
    290                 295                 300
Ser Val Ser Met Pro Phe Leu Ala Trp Tyr Gln Gln Lys Pro Gly Gln
305                 310                 315                 320
Ala Pro Arg Leu Leu Ile Tyr Gly Ala Ser Ser Arg Ala Thr Gly Ile
                325                 330                 335
Pro Asp Arg Phe Ser Gly Ser Gly Ser Gly Thr Asp Phe Thr Leu Thr
            340                 345                 350
Ile Ser Arg Leu Glu Pro Glu Asp Phe Ala Val Tyr Tyr Cys Gln Gln
        355                 360                 365
Met Arg Gly Arg Pro Pro Thr Phe Gly Gln Gly Thr Lys Val Glu Ile
    370                 375                 380
Lys Ser Ser Ser Ser Gly Ser Ser Ser Gly Ser Ser Ser Ser Gly
385                 390                 395                 400
Val Arg Ser Ser Arg Thr Pro Ser Asp Lys Pro Val Ala His Val
                405                 410                 415
Val Ala Asn Pro Gln Ala Glu Gly Gln Leu Gln Trp Leu Asn Arg Ala
            420                 425                 430
Ala Asn Ala Leu Leu Ala Asn Gly Val Glu Leu Arg Asp Asn Gln Leu
        435                 440                 445
Val Val Pro Ser Glu Gly Leu Tyr Leu Ile Tyr Ser Gln Val Leu Phe
    450                 455                 460
Lys Gly Gln Gly Cys Pro Ser Thr His Val Leu Leu Thr His Thr Ile
465                 470                 475                 480
Ser Arg Ile Ala Val Ser Tyr Gln Thr Lys Val Asn Leu Leu Ser Ala
                485                 490                 495
```

```
Ile Lys Ser Pro Cys Gln Arg Glu Thr Pro Glu Gly Ala Glu Ala Lys
                500                 505                 510

Pro Trp Tyr Glu Pro Ile Tyr Leu Gly Gly Val Phe Gln Leu Glu Lys
            515                 520                 525

Gly Asp Arg Leu Ser Ala Glu Ile Asn Arg Pro Asp Tyr Leu Asp Phe
        530                 535                 540

Ala Glu Ser Gly Gln Val Tyr Phe Gly Ile Ile Ala Leu
545                 550                 555
```

<210> SEQ ID NO 37
<211> LENGTH: 157
<212> TYPE: PRT
<213> ORGANISM: Artificial Sequence
<220> FEATURE:
<223> OTHER INFORMATION: Amino acid sequence of the soluble form of the
      extracellular domain of human TNFalpha (R32A) mutant (huTNFalpha
      R32A)

<400> SEQUENCE: 37

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Ala
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 38
<211> LENGTH: 577
<212> TYPE: PRT
<213> ORGANISM: Artificial Sequence
<220> FEATURE:
<223> OTHER INFORMATION: Amino acid sequence of the huIL2-F8-huTNFalpha
      (R52A) mutant (huTNFalpha R52A) [extracellular domain] conjugate

<400> SEQUENCE: 38

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Ser Gly Gly Ala
130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Ser Gly Gly Gly Gly
            260                 265                 270

Ser Gly Gly Gly Gly Glu Ile Val Leu Thr Gln Ser Pro Gly Thr Leu
    275                 280                 285

Ser Leu Ser Pro Gly Glu Arg Ala Thr Leu Ser Cys Arg Ala Ser Gln
290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
        355                 360                 365

Met Arg Gly Arg Pro Pro Thr Phe Gly Gln Gly Thr Lys Val Glu Ile
    370                 375                 380

Lys Ser Ser Ser Ser Gly Ser Ser Ser Gly Ser Ser Ser Ser Ser Gly
385                 390                 395                 400

Gly Pro Gln Arg Glu Glu Phe Pro Arg Asp Leu Ser Leu Ile Ser Pro
                405                 410                 415

Leu Ala Gln Ala Val Arg Ser Ser Ser Arg Thr Pro Ser Asp Lys Pro
            420                 425                 430

Val Ala His Val Val Ala Asn Pro Gln Ala Glu Gly Gln Leu Gln Trp
        435                 440                 445

Leu Asn Arg Ala Ala Asn Ala Leu Leu Ala Asn Gly Val Glu Leu Arg
    450                 455                 460

Asp Asn Gln Leu Val Val Pro Ser Glu Gly Leu Tyr Leu Ile Tyr Ser
465                 470                 475                 480

Gln Val Leu Phe Lys Gly Gln Gly Cys Pro Ser Thr His Val Leu Leu
                485                 490                 495
```

```
Thr His Thr Ile Ser Arg Ile Ala Val Ser Tyr Gln Thr Lys Val Asn
            500                 505                 510

Leu Leu Ser Ala Ile Lys Ser Pro Cys Gln Arg Glu Thr Pro Glu Gly
        515                 520                 525

Ala Glu Ala Lys Pro Trp Tyr Glu Pro Ile Tyr Leu Gly Gly Val Phe
        530                 535                 540

Gln Leu Glu Lys Gly Asp Arg Leu Ser Ala Glu Ile Asn Arg Pro Asp
545                 550                 555                 560

Tyr Leu Asp Phe Ala Glu Ser Gly Gln Val Tyr Phe Gly Ile Ile Ala
                565                 570                 575

Leu
```

<210> SEQ ID NO 39
<211> LENGTH: 177
<212> TYPE: PRT
<213> ORGANISM: Artificial Sequence
<220> FEATURE:
<223> OTHER INFORMATION: Amino acid sequence of the extracellular domain
      of human TNFalpha (R52A) mutant (huTNFalpha R52A) [extracellular
      domain]

<400> SEQUENCE: 39

```
Gly Pro Gln Arg Glu Glu Phe Pro Arg Asp Leu Ser Leu Ile Ser Pro
1               5                   10                  15

Leu Ala Gln Ala Val Arg Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Ala Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
        130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu
```

<210> SEQ ID NO 40
<211> LENGTH: 552
<212> TYPE: PRT
<213> ORGANISM: Artificial Sequence
<220> FEATURE:
<223> OTHER INFORMATION: Amino acid sequence of the huIL2-F16-huTNFalpha
      (R32A) mutant [soluble form] conjugate

<400> SEQUENCE: 40

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
```

```
                 20                  25                  30
Asn Pro Lys Leu Thr Arg Met Leu Thr Phe Lys Phe Tyr Met Pro Lys
             35                  40                  45
Lys Ala Thr Glu Leu Lys His Leu Gln Cys Leu Glu Glu Leu Lys
         50                  55                  60
Pro Leu Glu Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
             100                 105                 110
Thr Ile Val Glu Phe Leu Asn Arg Trp Ile Thr Phe Cys Gln Ser Ile
             115                 120                 125
Ile Ser Thr Leu Thr Gly Asp Gly Ser Ser Gly Ser Gly Gly Ala
             130                 135                 140
Ser Glu Val Gln Leu Leu Glu Ser Gly Gly Gly Leu Val Gln Pro Gly
145                 150                 155                 160
Gly Ser Leu Arg Leu Ser Cys Ala Ala Ser Gly Phe Thr Phe Ser Arg
                 165                 170                 175
Tyr Gly Met Ser Trp Val Arg Gln Ala Pro Gly Lys Gly Leu Glu Trp
             180                 185                 190
Val Ser Ala Ile Ser Gly Ser Gly Gly Ser Thr Tyr Tyr Ala Asp Ser
             195                 200                 205
Val Lys Gly Arg Phe Thr Ile Ser Arg Asp Asn Ser Lys Asn Thr Leu
             210                 215                 220
Tyr Leu Gln Met Asn Ser Leu Arg Ala Glu Asp Thr Ala Val Tyr Tyr
225                 230                 235                 240
Cys Ala Lys Ala His Asn Ala Phe Asp Tyr Trp Gly Gln Gly Thr Leu
                 245                 250                 255
Val Thr Val Ser Arg Gly Gly Gly Ser Gly Gly Gly Ser Gly Gly Ser
             260                 265                 270
Ser Glu Leu Thr Gln Asp Pro Ala Val Ser Val Ala Leu Gly Gln Thr
             275                 280                 285
Val Arg Ile Thr Cys Gln Gly Asp Ser Leu Arg Ser Tyr Tyr Ala Ser
             290                 295                 300
Trp Tyr Gln Gln Lys Pro Gly Gln Ala Pro Val Leu Val Ile Tyr Gly
305                 310                 315                 320
Lys Asn Asn Arg Pro Ser Gly Ile Pro Asp Arg Phe Ser Gly Ser Ser
                 325                 330                 335
Ser Gly Asn Thr Ala Ser Leu Thr Ile Thr Gly Ala Gln Ala Glu Asp
             340                 345                 350
Glu Ala Asp Tyr Tyr Cys Asn Ser Ser Val Tyr Thr Met Pro Pro Val
             355                 360                 365
Val Phe Gly Gly Gly Thr Lys Leu Thr Val Leu Gly Ser Ser Ser Ser
             370                 375                 380
Gly Ser Ser Ser Gly Ser Ser Ser Gly Val Arg Ser Ser
385                 390                 395                 400
Arg Thr Pro Ser Asp Lys Pro Val Ala His Val Val Ala Asn Pro Gln
                 405                 410                 415
Ala Glu Gly Gln Leu Gln Trp Leu Asn Arg Ala Ala Asn Ala Leu Leu
             420                 425                 430
Ala Asn Gly Val Glu Leu Arg Asp Asn Gln Leu Val Val Pro Ser Glu
             435                 440                 445
```

```
Gly Leu Tyr Leu Ile Tyr Ser Gln Val Leu Phe Lys Gly Gln Gly Cys
    450                 455                 460

Pro Ser Thr His Val Leu Leu Thr His Thr Ile Ser Arg Ile Ala Val
465                 470                 475                 480

Ser Tyr Gln Thr Lys Val Asn Leu Leu Ser Ala Ile Lys Ser Pro Cys
                485                 490                 495

Gln Arg Glu Thr Pro Glu Gly Ala Glu Ala Lys Pro Trp Tyr Glu Pro
            500                 505                 510

Ile Tyr Leu Gly Gly Val Phe Gln Leu Glu Lys Gly Asp Arg Leu Ser
        515                 520                 525

Ala Glu Ile Asn Arg Pro Asp Tyr Leu Asp Phe Ala Glu Ser Gly Gln
    530                 535                 540

Val Tyr Phe Gly Ile Ile Ala Leu
545                 550

<210> SEQ ID NO 41
<211> LENGTH: 572
<212> TYPE: PRT
<213> ORGANISM: Artificial Sequence
<220> FEATURE:
<223> OTHER INFORMATION: Amino acid sequence of the huIL2-F16-huTNFalpha
      (R52A) mutant [extracellular domain] conjugate

<400> SEQUENCE: 41

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
```

-continued

```
                245                 250                 255
Val Thr Val Ser Arg Gly Gly Ser Gly Gly Gly Ser Gly Gly Ser
            260                 265                 270

Ser Glu Leu Thr Gln Asp Pro Ala Val Ser Val Ala Leu Gly Gln Thr
        275                 280                 285

Val Arg Ile Thr Cys Gln Gly Asp Ser Leu Arg Ser Tyr Tyr Ala Ser
    290                 295                 300

Trp Tyr Gln Gln Lys Pro Gly Gln Ala Pro Val Leu Val Ile Tyr Gly
305                 310                 315                 320

Lys Asn Asn Arg Pro Ser Gly Ile Pro Asp Arg Phe Ser Gly Ser Ser
                325                 330                 335

Ser Gly Asn Thr Ala Ser Leu Thr Ile Thr Gly Ala Gln Ala Glu Asp
            340                 345                 350

Glu Ala Asp Tyr Tyr Cys Asn Ser Ser Val Tyr Thr Met Pro Pro Val
        355                 360                 365

Val Phe Gly Gly Gly Thr Lys Leu Thr Val Leu Gly Ser Ser Ser Ser
    370                 375                 380

Gly Ser Ser Ser Gly Ser Ser Ser Gly Gly Pro Gln Arg Glu
385                 390                 395                 400

Glu Phe Pro Arg Asp Leu Ser Leu Ile Ser Pro Leu Ala Gln Ala Val
                405                 410                 415

Arg Ser Ser Arg Thr Pro Ser Asp Lys Pro Val Ala His Val Val
            420                 425                 430

Ala Asn Pro Gln Ala Glu Gly Gln Leu Gln Trp Leu Asn Arg Ala Ala
        435                 440                 445

Asn Ala Leu Leu Ala Asn Gly Val Glu Leu Arg Asp Asn Gln Leu Val
    450                 455                 460

Val Pro Ser Glu Gly Leu Tyr Leu Ile Tyr Ser Gln Val Leu Phe Lys
465                 470                 475                 480

Gly Gln Gly Cys Pro Ser Thr His Val Leu Leu Thr His Thr Ile Ser
                485                 490                 495

Arg Ile Ala Val Ser Tyr Gln Thr Lys Val Asn Leu Leu Ser Ala Ile
            500                 505                 510

Lys Ser Pro Cys Gln Arg Glu Thr Pro Glu Gly Ala Glu Ala Lys Pro
        515                 520                 525

Trp Tyr Glu Pro Ile Tyr Leu Gly Gly Val Phe Gln Leu Glu Lys Gly
    530                 535                 540

Asp Arg Leu Ser Ala Glu Ile Asn Arg Pro Asp Tyr Leu Asp Phe Ala
545                 550                 555                 560

Glu Ser Gly Gln Val Tyr Phe Gly Ile Ile Ala Leu
                565                 570
```

<210> SEQ ID NO 42
<211> LENGTH: 553
<212> TYPE: PRT
<213> ORGANISM: Artificial Sequence
<220> FEATURE:
<223> OTHER INFORMATION: Amino acid sequence of the huIL2-L19-huTNFalpha
    (R32A) mutant [soluble form] conjugate

<400> SEQUENCE: 42

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

-continued

```
Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Phe Ser Met Ser Trp Val Arg Gln Ala Pro Gly Lys Gly Leu Glu Trp
            180                 185                 190

Val Ser Ser Ile Ser Gly Ser Ser Gly Thr Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Pro Phe Pro Tyr Phe Asp Tyr Trp Gly Gln Gly Thr Leu
                245                 250                 255

Val Thr Val Ser Ser Gly Asp Gly Ser Ser Gly Ser Gly Gly Ala
            260                 265                 270

Ser Glu Ile Val Leu Thr Gln Ser Pro Gly Thr Leu Ser Leu Ser Pro
    275                 280                 285

Gly Glu Arg Ala Thr Leu Ser Cys Arg Ala Ser Gln Ser Val Ser Ser
290                 295                 300

Ser Tyr Leu Ala Trp Tyr Gln Gln Lys Pro Gly Gln Ala Pro Arg Leu
305                 310                 315                 320

Leu Ile Tyr Tyr Ala Ser Ser Arg Ala Thr Gly Ile Pro Asp Arg Phe
                325                 330                 335

Ser Gly Ser Gly Ser Gly Thr Asp Phe Thr Leu Thr Ile Ser Arg Leu
            340                 345                 350

Glu Pro Glu Asp Phe Ala Val Tyr Tyr Cys Gln Gln Thr Gly Arg Ile
        355                 360                 365

Pro Pro Thr Phe Gly Gln Gly Thr Lys Val Glu Ile Lys Ser Ser Ser
    370                 375                 380

Ser Gly Ser Ser Ser Ser Gly Ser Ser Ser Gly Val Arg Ser Ser
385                 390                 395                 400

Ser Arg Thr Pro Ser Asp Lys Pro Val Ala His Val Val Ala Asn Pro
                405                 410                 415

Gln Ala Glu Gly Gln Leu Gln Trp Leu Asn Arg Ala Ala Asn Ala Leu
            420                 425                 430

Leu Ala Asn Gly Val Glu Leu Arg Asp Asn Gln Leu Val Val Pro Ser
        435                 440                 445

Glu Gly Leu Tyr Leu Ile Tyr Ser Gln Val Leu Phe Lys Gly Gln Gly
```

```
              450                 455                 460
Cys Pro Ser Thr His Val Leu Leu Thr His Thr Ile Ser Arg Ile Ala
465                 470                 475                 480

Val Ser Tyr Gln Thr Lys Val Asn Leu Leu Ser Ala Ile Lys Ser Pro
                485                 490                 495

Cys Gln Arg Glu Thr Pro Glu Gly Ala Glu Ala Lys Pro Trp Tyr Glu
                500                 505                 510

Pro Ile Tyr Leu Gly Gly Val Phe Gln Leu Glu Lys Gly Asp Arg Leu
                515                 520                 525

Ser Ala Glu Ile Asn Arg Pro Asp Tyr Leu Asp Phe Ala Glu Ser Gly
                530                 535                 540

Gln Val Tyr Phe Gly Ile Ile Ala Leu
545                 550
```

<210> SEQ ID NO 43
<211> LENGTH: 573
<212> TYPE: PRT
<213> ORGANISM: Artificial Sequence
<220> FEATURE:
<223> OTHER INFORMATION: Amino acid sequence of the huIL2-L19-huTNFalpha
      (R52A) mutant [extracellular domain]

<400> SEQUENCE: 43

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Asp Gly Ser Ser Gly Ser Gly Gly Ala
130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Ser
                165                 170                 175

Phe Ser Met Ser Trp Val Arg Gln Ala Pro Gly Lys Gly Leu Glu Trp
                180                 185                 190

Val Ser Ser Ile Ser Gly Ser Ser Gly Thr Thr Tyr Tyr Ala Asp Ser
                195                 200                 205

Val Lys Gly Arg Phe Thr Ile Ser Arg Asp Asn Ser Lys Asn Thr Leu
                210                 215                 220

Tyr Leu Gln Met Asn Ser Leu Arg Ala Glu Asp Thr Ala Val Tyr Tyr
225                 230                 235                 240

Cys Ala Lys Pro Phe Pro Tyr Phe Asp Tyr Trp Gly Gln Gly Thr Leu
                245                 250                 255
```

Val Thr Val Ser Ser Gly Asp Gly Ser Gly Ser Gly Ala
            260                 265                 270

Ser Glu Ile Val Leu Thr Gln Ser Pro Gly Thr Leu Ser Leu Ser Pro
                275                 280                 285

Gly Glu Arg Ala Thr Leu Ser Cys Arg Ala Ser Gln Ser Val Ser Ser
            290                 295                 300

Ser Tyr Leu Ala Trp Tyr Gln Gln Lys Pro Gly Gln Ala Pro Arg Leu
305                 310                 315                 320

Leu Ile Tyr Tyr Ala Ser Ser Arg Ala Thr Gly Ile Pro Asp Arg Phe
                325                 330                 335

Ser Gly Ser Gly Ser Gly Thr Asp Phe Thr Leu Thr Ile Ser Arg Leu
            340                 345                 350

Glu Pro Glu Asp Phe Ala Val Tyr Tyr Cys Gln Gln Thr Gly Arg Ile
                355                 360                 365

Pro Pro Thr Phe Gly Gln Gly Thr Lys Val Glu Ile Lys Ser Ser Ser
            370                 375                 380

Ser Gly Ser Ser Ser Gly Ser Ser Ser Gly Gly Pro Gln Arg
385                 390                 395                 400

Glu Glu Phe Pro Arg Asp Leu Ser Leu Ile Ser Pro Leu Ala Gln Ala
                405                 410                 415

Val Arg Ser Ser Ser Arg Thr Pro Ser Asp Lys Pro Val Ala His Val
            420                 425                 430

Val Ala Asn Pro Gln Ala Glu Gly Gln Leu Gln Trp Leu Asn Arg Ala
                435                 440                 445

Ala Asn Ala Leu Leu Ala Asn Gly Val Glu Leu Arg Asp Asn Gln Leu
450                 455                 460

Val Val Pro Ser Glu Gly Leu Tyr Leu Ile Tyr Ser Gln Val Leu Phe
465                 470                 475                 480

Lys Gly Gln Gly Cys Pro Ser Thr His Val Leu Leu Thr His Thr Ile
                485                 490                 495

Ser Arg Ile Ala Val Ser Tyr Gln Thr Lys Val Asn Leu Leu Ser Ala
                500                 505                 510

Ile Lys Ser Pro Cys Gln Arg Glu Thr Pro Glu Gly Ala Glu Ala Lys
            515                 520                 525

Pro Trp Tyr Glu Pro Ile Tyr Leu Gly Gly Val Phe Gln Leu Glu Lys
            530                 535                 540

Gly Asp Arg Leu Ser Ala Glu Ile Asn Arg Pro Asp Tyr Leu Asp Phe
545                 550                 555                 560

Ala Glu Ser Gly Gln Val Tyr Phe Gly Ile Ile Ala Leu
                565                 570

<210> SEQ ID NO 44
<211> LENGTH: 555
<212> TYPE: PRT
<213> ORGANISM: Artificial Sequence
<220> FEATURE:
<223> OTHER INFORMATION: no acid sequence of the huIL2-L19-huTNFalpha
      (R32A) mutant [soluble form] conjugate

<400> SEQUENCE: 44

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

-continued

```
Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                        85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Gly Gly Gly Gly Ser Gly
        130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                    165                 170                 175

Ser Ser Phe Ser Met Ser Trp Val Arg Gln Ala Pro Gly Lys Gly Leu
                180                 185                 190

Glu Trp Val Ser Ser Ile Ser Gly Ser Ser Gly Thr Thr Tyr Tyr Ala
            195                 200                 205

Asp Ser Val Lys Gly Arg Phe Thr Ile Ser Arg Asp Asn Ser Lys Asn
        210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                    245                 250                 255

Thr Leu Val Thr Val Ser Ser Gly Asp Gly Ser Ser Gly Gly Ser Gly
                260                 265                 270

Gly Ala Ser Glu Ile Val Leu Thr Gln Ser Pro Gly Thr Leu Ser Leu
            275                 280                 285

Ser Pro Gly Glu Arg Ala Thr Leu Ser Cys Arg Ala Ser Gln Ser Val
290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
                    325                 330                 335

Arg Phe Ser Gly Ser Gly Ser Gly Thr Asp Phe Thr Leu Thr Ile Ser
                340                 345                 350

Arg Leu Glu Pro Glu Asp Phe Ala Val Tyr Tyr Cys Gln Gln Thr Gly
            355                 360                 365

Arg Ile Pro Pro Thr Phe Gly Gln Gly Thr Lys Val Glu Ile Lys Ser
370                 375                 380

Ser Ser Ser Gly Ser Ser Ser Gly Ser Ser Ser Gly Val Arg
385                 390                 395                 400

Ser Ser Ser Arg Thr Pro Ser Asp Lys Pro Val Ala His Val Val Ala
                    405                 410                 415

Asn Pro Gln Ala Glu Gly Gln Leu Gln Trp Leu Asn Arg Ala Ala Asn
                420                 425                 430

Ala Leu Leu Ala Asn Gly Val Glu Leu Arg Asp Asn Gln Leu Val Val
            435                 440                 445

Pro Ser Glu Gly Leu Tyr Leu Ile Tyr Ser Gln Val Leu Phe Lys Gly
450                 455                 460
```

```
Gln Gly Cys Pro Ser Thr His Val Leu Leu Thr His Thr Ile Ser Arg
465                 470                 475                 480

Ile Ala Val Ser Tyr Gln Thr Lys Val Asn Leu Leu Ser Ala Ile Lys
                485                 490                 495

Ser Pro Cys Gln Arg Glu Thr Pro Glu Gly Ala Glu Ala Lys Pro Trp
            500                 505                 510

Tyr Glu Pro Ile Tyr Leu Gly Gly Val Phe Gln Leu Glu Lys Gly Asp
            515                 520                 525

Arg Leu Ser Ala Glu Ile Asn Arg Pro Asp Tyr Leu Asp Phe Ala Glu
        530                 535                 540

Ser Gly Gln Val Tyr Phe Gly Ile Ile Ala Leu
545                 550                 555

<210> SEQ ID NO 45
<211> LENGTH: 575
<212> TYPE: PRT
<213> ORGANISM: Artificial Sequence
<220> FEATURE:
<223> OTHER INFORMATION: Amino acid sequence of the huIL2-L19-huTNFalpha
      (R52A) mutant [extracellular domain] conjugate

<400> SEQUENCE: 45

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
            165                 170                 175

Ser Ser Phe Ser Met Ser Trp Val Arg Gln Ala Pro Lys Gly Leu
            180                 185                 190

Glu Trp Val Ser Ser Ile Ser Gly Ser Ser Gly Thr Thr Tyr Tyr Ala
            195                 200                 205

Asp Ser Val Lys Gly Arg Phe Thr Ile Ser Arg Asp Asn Ser Lys Asn
        210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Gly Ser Gly
            260                 265                 270
```

-continued

```
Gly Ala Ser Glu Ile Val Leu Thr Gln Ser Pro Gly Thr Leu Ser Leu
            275                 280                 285

Ser Pro Gly Glu Arg Ala Thr Leu Ser Cys Arg Ala Ser Gln Ser Val
290                 295                 300

Ser Ser Ser Phe Leu Ala Trp Tyr Gln Lys Pro Gly Gln Ala Pro
305                 310                 315                 320

Arg Leu Leu Ile Tyr Tyr Ala Ser Ser Arg Ala Thr Gly Ile Pro Asp
            325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
            355                 360                 365

Arg Ile Pro Pro Thr Phe Gly Gln Gly Thr Lys Val Glu Ile Lys Ser
            370                 375                 380

Ser Ser Ser Gly Ser Ser Ser Gly Ser Ser Ser Gly Gly Pro
385                 390                 395                 400

Gln Arg Glu Glu Phe Pro Arg Asp Leu Ser Leu Ile Ser Pro Leu Ala
                405                 410                 415

Gln Ala Val Arg Ser Ser Arg Thr Pro Ser Asp Lys Pro Val Ala
            420                 425                 430

His Val Val Ala Asn Pro Gln Ala Glu Gly Gln Leu Gln Trp Leu Asn
            435                 440                 445

Arg Ala Ala Asn Ala Leu Leu Ala Asn Gly Val Glu Leu Arg Asp Asn
450                 455                 460

Gln Leu Val Val Pro Ser Glu Gly Leu Tyr Leu Ile Tyr Ser Gln Val
465                 470                 475                 480

Leu Phe Lys Gly Gln Gly Cys Pro Ser Thr His Val Leu Leu Thr His
            485                 490                 495

Thr Ile Ser Arg Ile Ala Val Ser Tyr Gln Thr Lys Val Asn Leu Leu
            500                 505                 510

Ser Ala Ile Lys Ser Pro Cys Gln Arg Glu Thr Pro Glu Gly Ala Glu
            515                 520                 525

Ala Lys Pro Trp Tyr Glu Pro Ile Tyr Leu Gly Gly Val Phe Gln Leu
            530                 535                 540

Glu Lys Gly Asp Arg Leu Ser Ala Glu Ile Asn Arg Pro Asp Tyr Leu
545                 550                 555                 560

Asp Phe Ala Glu Ser Gly Gln Val Tyr Phe Gly Ile Ile Ala Leu
            565                 570                 575

<210> SEQ ID NO 46
<211> LENGTH: 239
<212> TYPE: PRT
<213> ORGANISM: Artificial Sequence
<220> FEATURE:
<223> OTHER INFORMATION: Amino acid sequence of the scFv(F16)

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Ser Gly Gly Gly Gly Ser Gly Gly
            115                 120                 125

Gly Gly Ser Ser Glu Leu Thr Gln Asp Pro Ala Val Ser Val Ala Leu
130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
            195                 200                 205

Ala Glu Asp Glu Ala Asp Tyr Tyr Cys Asn Ser Val Tyr Thr Met
    210                 215                 220

Pro Pro Val Val Phe Gly Gly Gly Thr Lys Leu Thr Val Leu Gly
225                 230                 235

<210> SEQ ID NO 47
<211> LENGTH: 556
<212> TYPE: PRT
<213> ORGANISM: Artificial Sequence
<220> FEATURE:
<223> OTHER INFORMATION: Amino acid sequence of the huIL2-F16-huTNFalpha
      (R32A) mutant [soluble form] conjugate

<400> SEQUENCE: 47

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
        130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Gly Lys Gly Leu Glu Trp

```
            180                 185                 190
Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
            210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
                245                 250                 255

Val Thr Val Ser Arg Gly Gly Gly Ser Gly Gly Gly Gly Ser Gly
            260                 265                 270

Gly Gly Ser Ser Glu Leu Thr Gln Asp Pro Ala Val Ser Val Ala
            275                 280                 285

Leu Gly Gln Thr Val Arg Ile Thr Cys Gln Gly Asp Ser Leu Arg Ser
            290                 295                 300

Tyr Tyr Ala Ser Trp Tyr Gln Gln Lys Pro Gly Gln Ala Pro Val Leu
305                 310                 315                 320

Val Ile Tyr Gly Lys Asn Asn Arg Pro Ser Gly Ile Pro Asp Arg Phe
                325                 330                 335

Ser Gly Ser Ser Ser Gly Asn Thr Ala Ser Leu Thr Ile Thr Gly Ala
                340                 345                 350

Gln Ala Glu Asp Glu Ala Asp Tyr Tyr Cys Asn Ser Ser Val Tyr Thr
            355                 360                 365

Met Pro Pro Val Val Phe Gly Gly Thr Lys Leu Thr Val Leu Gly
370                 375                 380

Ser Ser Ser Ser Gly Ser Ser Ser Gly Ser Ser Ser Ser Gly Val
385                 390                 395                 400

Arg Ser Ser Ser Arg Thr Pro Ser Asp Lys Pro Val Ala His Val Val
                405                 410                 415

Ala Asn Pro Gln Ala Glu Gly Gln Leu Gln Trp Leu Asn Arg Ala Ala
            420                 425                 430

Asn Ala Leu Leu Ala Asn Gly Val Glu Leu Arg Asp Asn Gln Leu Val
            435                 440                 445

Val Pro Ser Glu Gly Leu Tyr Leu Ile Tyr Ser Gln Val Leu Phe Lys
            450                 455                 460

Gly Gln Gly Cys Pro Ser Thr His Val Leu Leu Thr His Thr Ile Ser
465                 470                 475                 480

Arg Ile Ala Val Ser Tyr Gln Thr Lys Val Asn Leu Leu Ser Ala Ile
                485                 490                 495

Lys Ser Pro Cys Gln Arg Glu Thr Pro Glu Gly Ala Glu Ala Lys Pro
                500                 505                 510

Trp Tyr Glu Pro Ile Tyr Leu Gly Gly Val Phe Gln Leu Glu Lys Gly
            515                 520                 525

Asp Arg Leu Ser Ala Glu Ile Asn Arg Pro Asp Tyr Leu Asp Phe Ala
            530                 535                 540

Glu Ser Gly Gln Val Tyr Phe Gly Ile Ile Ala Leu
545                 550                 555

<210> SEQ ID NO 48
<211> LENGTH: 576
<212> TYPE: PRT
<213> ORGANISM: Artificial Sequence
<220> FEATURE:
<223> OTHER INFORMATION: Amino acid sequence of the huIL2-F16-huTNFalpha
      (R52A) mutant [extracellular domain] conjugate
```

```
<400> SEQUENCE: 48

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Gly Ser Gly Gly Ala
130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
                245                 250                 255

Val Thr Val Ser Arg Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
        275                 280                 285

Leu Gly Gln Thr Val Arg Ile Thr Cys Gln Gly Asp Ser Leu Arg Ser
    290                 295                 300

Tyr Tyr Ala Ser Trp Tyr Gln Gln Lys Pro Gly Gln Ala Pro Val Leu
305                 310                 315                 320

Val Ile Tyr Gly Lys Asn Asn Arg Pro Ser Gly Ile Pro Asp Arg Phe
                325                 330                 335

Ser Gly Ser Ser Ser Gly Asn Thr Ala Ser Leu Thr Ile Thr Gly Ala
            340                 345                 350

Gln Ala Glu Asp Glu Ala Asp Tyr Tyr Cys Asn Ser Ser Val Tyr Thr
            355                 360                 365

Met Pro Pro Val Val Phe Gly Gly Gly Thr Lys Leu Thr Val Leu Gly
        370                 375                 380

Ser Ser Ser Ser Gly Ser Ser Ser Gly Ser Ser Ser Ser Gly Gly
385                 390                 395                 400

Pro Gln Arg Glu Glu Phe Pro Arg Asp Leu Ser Leu Ile Ser Pro Leu
```

```
                    405                 410                 415
Ala Gln Ala Val Arg Ser Ser Arg Thr Pro Ser Asp Lys Pro Val
            420                 425                 430

Ala His Val Val Ala Asn Pro Gln Ala Glu Gly Gln Leu Gln Trp Leu
        435                 440                 445

Asn Arg Ala Ala Asn Ala Leu Leu Ala Asn Gly Val Glu Leu Arg Asp
450                 455                 460

Asn Gln Leu Val Val Pro Ser Glu Gly Leu Tyr Leu Ile Tyr Ser Gln
465                 470                 475                 480

Val Leu Phe Lys Gly Gln Gly Cys Pro Ser Thr His Val Leu Leu Thr
                485                 490                 495

His Thr Ile Ser Arg Ile Ala Val Ser Tyr Gln Thr Lys Val Asn Leu
            500                 505                 510

Leu Ser Ala Ile Lys Ser Pro Cys Gln Arg Glu Thr Pro Glu Gly Ala
            515                 520                 525

Glu Ala Lys Pro Trp Tyr Glu Pro Ile Tyr Leu Gly Gly Val Phe Gln
530                 535                 540

Leu Glu Lys Gly Asp Arg Leu Ser Ala Glu Ile Asn Arg Pro Asp Tyr
545                 550                 555                 560

Leu Asp Phe Ala Glu Ser Gly Gln Val Tyr Phe Gly Ile Ile Ala Leu
                565                 570                 575

<210> SEQ ID NO 49
<211> LENGTH: 14
<212> TYPE: PRT
<213> ORGANISM: Artificial Sequence
<220> FEATURE:
<223> OTHER INFORMATION: Amino acid sequence of the linker linking the
      antibody molecule and IL2 and/or the TNF mutant

<400> SEQUENCE: 49

Gly Gly Gly Gly Ser Gly Gly Gly Gly Ser Gly Gly Gly Gly
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Amino acid sequence of the linker linking the
      VH domain to the VL domain of the antibody

<400> SEQUENCE: 50

Gly Asp Gly Ser Ser Gly Gly Ser Gly Gly Ala Ser
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Amino acid sequence of the linker linking the
      VH domain to the VL domain of the antibody

<400> SEQUENCE: 51

Gly Gly Gly Ser Gly Gly Gly Ser Gly Gly
1               5                   10

<210> SEQ ID NO 52
<211> LENGTH: 157
<212> TYPE: PRT
<213> ORGANISM: Artificial Sequence
```

<220> FEATURE:
<223> OTHER INFORMATION: Amino acid sequence of the soluble form of the
      extracellular domain of human TNFalpha (R32W) mutant (huTNFalpha
      R32W)

<400> SEQUENCE: 52

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Trp
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 53
<211> LENGTH: 177
<212> TYPE: PRT
<213> ORGANISM: Artificial Sequence
<220> FEATURE:
<223> OTHER INFORMATION: Amino acid sequence of the extracellular domain
      of human TNFalpha (R52W) mutant (huTNFalpha R52W)

<400> SEQUENCE: 53

Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Trp Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly
        115                 120                 125

Ala Glu Ala Lys Pro Trp Tyr Glu Pro Ile Tyr Leu Gly Gly Val Phe
    130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala 165                 170                 175

Leu

<210> SEQ ID NO 54
<211> LENGTH: 157
<212> TYPE: PRT
<213> ORGANISM: Artificial Sequence
<220> FEATURE:
<223> OTHER INFORMATION: Amino acid sequence of the soluble form of the
      extracellular domain of human TNFalpha (R32F) mutant (huTNFalpha
      R32F)

<400> SEQUENCE: 54

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Phe
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155

<210> SEQ ID NO 55
<211> LENGTH: 177
<212> TYPE: PRT
<213> ORGANISM: Artificial Sequence
<220> FEATURE:
<223> OTHER INFORMATION: Amino acid sequence of the extracellular domain
      of human TNFalpha (R52F) mutant (huTNFalpha R52F)

<400> SEQUENCE: 55

Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Phe Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
            100                 105                 110

Leu Leu Ser Ala Ile Lys Ser Pro Cys Gln Arg Glu Thr Pro Glu Gly

```
                  115                 120                 125
Ala Glu Ala Lys Pro Trp Tyr Glu Pro Ile Tyr Leu Gly Gly Val Phe
            130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu
```

<210> SEQ ID NO 56
<211> LENGTH: 157
<212> TYPE: PRT
<213> ORGANISM: Artificial Sequence
<220> FEATURE:
<223> OTHER INFORMATION: Amino acid sequence of the soluble form of the
      extracellular domain of human TNFalpha (R32V) mutant (huTNFalpha
      R32V)

<400> SEQUENCE: 56

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Val
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 57
<211> LENGTH: 177
<212> TYPE: PRT
<213> ORGANISM: Artificial Sequence
<220> FEATURE:
<223> OTHER INFORMATION: Amino acid sequence of the extracellular domain
      of human TNFalpha (R52V) mutant (huTNFalpha R52V)

<400> SEQUENCE: 57

```
Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
            20                  25                  30

Val Ala His Val Val Ala Asn Pro Gln Ala Glu Gly Gln Leu Gln Trp
        35                  40                  45

Leu Asn Arg Val Ala Asn Ala Leu Leu Ala Asn Gly Val Glu Leu Arg
    50                  55                  60

Asp Asn Gln Leu Val Val Pro Ser Glu Gly Leu Tyr Leu Ile Tyr Ser
```

```
65                  70                  75                  80
Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
                100                 105                 110

Leu Leu Ser Ala Ile Lys Ser Pro Cys Gln Arg Glu Thr Pro Glu Gly
                115                 120                 125

Ala Glu Ala Lys Pro Trp Tyr Glu Pro Ile Tyr Leu Gly Gly Val Phe
                130                 135                 140

Gln Leu Glu Lys Gly Asp Arg Leu Ser Ala Glu Ile Asn Arg Pro Asp
145                 150                 155                 160

Tyr Leu Asp Phe Ala Glu Ser Gly Gln Val Tyr Phe Gly Ile Ile Ala
                165                 170                 175

Leu
```

<210> SEQ ID NO 58
<211> LENGTH: 557
<212> TYPE: PRT
<213> ORGANISM: Artificial Sequence
<220> FEATURE:
<223> OTHER INFORMATION: Amino acid sequence of the huIL2-F8-huTNFalpha
      (R32W) mutant [soluble form] conjugate

<400> SEQUENCE: 58

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Asp Gly Ser Ser Gly Gly Ser Gly Gly Ala
                130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
                180                 185                 190

Val Ser Ala Ile Ser Gly Ser Gly Gly Ser Thr Tyr Tyr Ala Asp Ser
                195                 200                 205

Val Lys Gly Arg Phe Thr Ile Ser Arg Asp Asn Ser Lys Asn Thr Leu
                210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
```

245              250              255
Thr Leu Val Thr Val Ser Ser Gly Gly Gly Ser Gly Gly Gly
        260              265              270

Ser Gly Gly Gly Gly Glu Ile Val Leu Thr Gln Ser Pro Gly Thr Leu
        275              280              285

Ser Leu Ser Pro Gly Glu Arg Ala Thr Leu Ser Cys Arg Ala Ser Gln
        290              295              300

Ser Val Ser Met Pro Phe Leu Ala Trp Tyr Gln Gln Lys Pro Gly Gln
305              310              315              320

Ala Pro Arg Leu Leu Ile Tyr Gly Ala Ser Ser Arg Ala Thr Gly Ile
                325              330              335

Pro Asp Arg Phe Ser Gly Ser Gly Ser Gly Thr Asp Phe Thr Leu Thr
                340              345              350

Ile Ser Arg Leu Glu Pro Glu Asp Phe Ala Val Tyr Tyr Cys Gln Gln
                355              360              365

Met Arg Gly Arg Pro Pro Thr Phe Gly Gln Gly Thr Lys Val Glu Ile
        370              375              380

Lys Ser Ser Ser Ser Gly Ser Ser Ser Gly Ser Ser Ser Ser Ser Gly
385              390              395              400

Val Arg Ser Ser Ser Arg Thr Pro Ser Asp Lys Pro Val Ala His Val
                405              410              415

Val Ala Asn Pro Gln Ala Glu Gly Gln Leu Gln Trp Leu Asn Arg Trp
                420              425              430

Ala Asn Ala Leu Leu Ala Asn Gly Val Glu Leu Arg Asp Asn Gln Leu
                435              440              445

Val Val Pro Ser Glu Gly Leu Tyr Leu Ile Tyr Ser Gln Val Leu Phe
        450              455              460

Lys Gly Gln Gly Cys Pro Ser Thr His Val Leu Leu Thr His Thr Ile
465              470              475              480

Ser Arg Ile Ala Val Ser Tyr Gln Thr Lys Val Asn Leu Leu Ser Ala
                485              490              495

Ile Lys Ser Pro Cys Gln Arg Glu Thr Pro Glu Gly Ala Glu Ala Lys
                500              505              510

Pro Trp Tyr Glu Pro Ile Tyr Leu Gly Gly Val Phe Gln Leu Glu Lys
                515              520              525

Gly Asp Arg Leu Ser Ala Glu Ile Asn Arg Pro Asp Tyr Leu Asp Phe
        530              535              540

Ala Glu Ser Gly Gln Val Tyr Phe Gly Ile Ile Ala Leu
545              550              555

<210> SEQ ID NO 59
<211> LENGTH: 577
<212> TYPE: PRT
<213> ORGANISM: Artificial Sequence
<220> FEATURE:
<223> OTHER INFORMATION: Amino acid sequence of the huIL2-F8-huTNFalpha
      (R52W) mutant (huTNFalpha R52W) [extracellular domain] conjugate

<400> SEQUENCE: 59

Ala Pro Thr Ser Ser Ser Thr Lys Lys Thr Gln Leu Gln Leu Glu His
1               5               10              15

Leu Leu Leu Asp Leu Gln Met Ile Leu Asn Gly Ile Asn Asn Tyr Lys
            20              25              30

Asn Pro Lys Leu Thr Arg Met Leu Thr Phe Lys Phe Tyr Met Pro Lys
        35              40              45

-continued

```
Lys Ala Thr Glu Leu Lys His Leu Gln Cys Leu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Asp Gly Ser Ser Gly Ser Gly Gly Ala
    130                 135                 140
Ser Glu Val Gln Leu Leu Glu Ser Gly Gly Gly Leu Val Gln Pro Gly
145                 150                 155                 160
Gly Ser Leu Arg Leu Ser Cys Ala Ala Ser Gly Phe Thr Phe Ser Leu
                165                 170                 175
Phe Thr Met Ser Trp Val Arg Gln Ala Pro Gly Lys Gly Leu Glu Trp
            180                 185                 190
Val Ser Ala Ile Ser Gly Ser Gly Gly Ser Thr Tyr Tyr Ala Asp Ser
        195                 200                 205
Val Lys Gly Arg Phe Thr Ile Ser Arg Asp Asn Ser Lys Asn Thr Leu
    210                 215                 220
Tyr Leu Gln Met Asn Ser Leu Arg Ala Glu Asp Thr Ala Val Tyr Tyr
225                 230                 235                 240
Cys Ala Lys Ser Thr His Leu Tyr Leu Phe Asp Tyr Trp Gly Gln Gly
                245                 250                 255
Thr Leu Val Thr Val Ser Ser Gly Gly Gly Ser Gly Gly Gly Gly
            260                 265                 270
Ser Gly Gly Gly Gly Glu Ile Val Leu Thr Gln Ser Pro Gly Thr Leu
        275                 280                 285
Ser Leu Ser Pro Gly Glu Arg Ala Thr Leu Ser Cys Arg Ala Ser Gln
    290                 295                 300
Ser Val Ser Met Pro Phe Leu Ala Trp Tyr Gln Gln Lys Pro Gly Gln
305                 310                 315                 320
Ala Pro Arg Leu Leu Ile Tyr Gly Ala Ser Ser Arg Ala Thr Gly Ile
                325                 330                 335
Pro Asp Arg Phe Ser Gly Ser Gly Ser Gly Thr Asp Phe Thr Leu Thr
            340                 345                 350
Ile Ser Arg Leu Glu Pro Glu Asp Phe Ala Val Tyr Tyr Cys Gln Gln
        355                 360                 365
Met Arg Gly Arg Pro Pro Thr Phe Gly Gln Gly Thr Lys Val Glu Ile
    370                 375                 380
Lys Ser Ser Ser Ser Gly Ser Ser Ser Gly Ser Ser Ser Ser Gly
385                 390                 395                 400
Gly Pro Gln Arg Glu Glu Phe Pro Arg Asp Leu Ser Leu Ile Ser Pro
                405                 410                 415
Leu Ala Gln Ala Val Arg Ser Ser Arg Thr Pro Ser Asp Lys Pro
            420                 425                 430
Val Ala His Val Val Ala Asn Pro Gln Ala Glu Gly Gln Leu Gln Trp
        435                 440                 445
Leu Asn Arg Trp Ala Asn Ala Leu Leu Ala Asn Gly Val Glu Leu Arg
    450                 455                 460
Asp Asn Gln Leu Val Val Pro Ser Glu Gly Leu Tyr Leu Ile Tyr Ser
```

```
           465                 470                 475                 480
       Gln Val Leu Phe Lys Gly Gln Gly Cys Pro Ser Thr His Val Leu Leu
                       485                 490                 495

Thr His Thr Ile Ser Arg Ile Ala Val Ser Tyr Gln Thr Lys Val Asn
                       500                 505                 510

Leu Leu Ser Ala Ile Lys Ser Pro Cys Gln Arg Glu Thr Pro Glu Gly
                       515                 520                 525

Ala Glu Ala Lys Pro Trp Tyr Glu Pro Ile Tyr Leu Gly Gly Val Phe
                       530                 535                 540

Gln Leu Glu Lys Gly Asp Arg Leu Ser Ala Glu Ile Asn Arg Pro Asp
       545                 550                 555                 560

Tyr Leu Asp Phe Ala Glu Ser Gly Gln Val Tyr Phe Gly Ile Ile Ala
                       565                 570                 575

Leu

<210> SEQ ID NO 60
<211> LENGTH: 557
<212> TYPE: PRT
<213> ORGANISM: Artificial Sequence
<220> FEATURE:
<223> OTHER INFORMATION: Amino acid sequence of the huIL2-F8-huTNFalpha
      (R32F) mutant [soluble form] conjugate

<400> SEQUENCE: 60

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Asp Gly Ser Ser Gly Gly Ser Gly Gly Ala
                130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
                180                 185                 190

Val Ser Ala Ile Ser Gly Ser Gly Gly Ser Thr Tyr Tyr Ala Asp Ser
                195                 200                 205

Val Lys Gly Arg Phe Thr Ile Ser Arg Asp Asn Ser Lys Asn Thr Leu
                210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
```

```
            245                 250                 255
Thr Leu Val Thr Val Ser Ser Gly Gly Gly Ser Gly Gly Gly
            260                 265                 270

Ser Gly Gly Gly Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln
    290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
        355                 360                 365

Met Arg Gly Arg Pro Pro Thr Phe Gly Gln Gly Thr Lys Val Glu Ile
    370                 375                 380

Lys Ser Ser Ser Ser Gly Ser Ser Ser Gly Ser Ser Ser Gly
385                 390                 395                 400

Val Arg Ser Ser Arg Thr Pro Ser Asp Lys Pro Val Ala His Val
                405                 410                 415

Val Ala Asn Pro Gln Ala Glu Gly Gln Leu Gln Trp Leu Asn Arg Phe
            420                 425                 430

Ala Asn Ala Leu Leu Ala Asn Gly Val Glu Leu Arg Asp Asn Gln Leu
        435                 440                 445

Val Val Pro Ser Glu Gly Leu Tyr Leu Ile Tyr Ser Gln Val Leu Phe
    450                 455                 460

Lys Gly Gln Gly Cys Pro Ser Thr His Val Leu Leu Thr His Thr Ile
465                 470                 475                 480

Ser Arg Ile Ala Val Ser Tyr Gln Thr Lys Val Asn Leu Leu Ser Ala
                485                 490                 495

Ile Lys Ser Pro Cys Gln Arg Glu Thr Pro Glu Gly Ala Glu Ala Lys
            500                 505                 510

Pro Trp Tyr Glu Pro Ile Tyr Leu Gly Gly Val Phe Gln Leu Glu Lys
        515                 520                 525

Gly Asp Arg Leu Ser Ala Glu Ile Asn Arg Pro Asp Tyr Leu Asp Phe
    530                 535                 540

Ala Glu Ser Gly Gln Val Tyr Phe Gly Ile Ile Ala Leu
545                 550                 555
```

<210> SEQ ID NO 61
<211> LENGTH: 577
<212> TYPE: PRT
<213> ORGANISM: Artificial Sequence
<220> FEATURE:
<223> OTHER INFORMATION: Amino acid sequence of the huIL2-F8-huTNFalpha
      (R52F) mutant (huTNFalpha R52F) [extracellular domain] conjugate

<400> SEQUENCE: 61

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45
```

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Glu Ile Val Leu Thr Gln Ser Pro Gly Thr Leu
    275                 280                 285

Ser Leu Ser Pro Gly Glu Arg Ala Thr Leu Ser Cys Arg Ala Ser Gln
    290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
            355                 360                 365

Met Arg Gly Arg Pro Pro Thr Phe Gly Gln Gly Thr Lys Val Glu Ile
    370                 375                 380

Lys Ser Ser Ser Ser Gly Ser Ser Ser Gly Ser Ser Ser Ser Gly
385                 390                 395                 400

Gly Pro Gln Arg Glu Glu Phe Pro Arg Asp Leu Ser Leu Ile Ser Pro
                405                 410                 415

Leu Ala Gln Ala Val Arg Ser Ser Arg Thr Pro Ser Asp Lys Pro
            420                 425                 430

Val Ala His Val Val Ala Asn Pro Gln Ala Glu Gly Gln Leu Gln Trp
            435                 440                 445

Leu Asn Arg Phe Ala Asn Ala Leu Leu Ala Asn Gly Val Glu Leu Arg
450                 455                 460

Asp Asn Gln Leu Val Val Pro Ser Glu Gly Leu Tyr Leu Ile Tyr Ser
```

```
                    465                 470                 475                 480
Gln Val Leu Phe Lys Gly Gln Gly Cys Pro Ser Thr His Val Leu Leu
                    485                 490                 495

Thr His Thr Ile Ser Arg Ile Ala Val Ser Tyr Gln Thr Lys Val Asn
                    500                 505                 510

Leu Leu Ser Ala Ile Lys Ser Pro Cys Gln Arg Glu Thr Pro Glu Gly
                    515                 520                 525

Ala Glu Ala Lys Pro Trp Tyr Glu Pro Ile Tyr Leu Gly Gly Val Phe
                    530                 535                 540

Gln Leu Glu Lys Gly Asp Arg Leu Ser Ala Glu Ile Asn Arg Pro Asp
545                 550                 555                 560

Tyr Leu Asp Phe Ala Glu Ser Gly Gln Val Tyr Phe Gly Ile Ile Ala
                    565                 570                 575

Leu

<210> SEQ ID NO 62
<211> LENGTH: 557
<212> TYPE: PRT
<213> ORGANISM: Artificial Sequence
<220> FEATURE:
<223> OTHER INFORMATION: Amino acid sequence of the huIL2-F8-huTNFalpha
      (R32V) mutant [soluble form] conjugate

<400> SEQUENCE: 62

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65              70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Gly Ser Gly Gly Ala
            130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
                180                 185                 190

Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
            210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
```

245                 250                 255
Thr Leu Val Thr Val Ser Ser Gly Gly Gly Gly Ser Gly Gly Gly
                260                 265                 270
Ser Gly Gly Gly Glu Ile Val Leu Thr Gln Ser Pro Gly Thr Leu
            275                 280                 285
Ser Leu Ser Pro Gly Glu Arg Ala Thr Leu Ser Cys Arg Ala Ser Gln
        290                 295                 300
Ser Val Ser Met Pro Phe Leu Ala Trp Tyr Gln Gln Lys Pro Gly Gln
305                 310                 315                 320
Ala Pro Arg Leu Leu Ile Tyr Gly Ala Ser Ser Arg Ala Thr Gly Ile
                325                 330                 335
Pro Asp Arg Phe Ser Gly Ser Gly Ser Gly Thr Asp Phe Thr Leu Thr
                340                 345                 350
Ile Ser Arg Leu Glu Pro Glu Asp Phe Ala Val Tyr Tyr Cys Gln Gln
                355                 360                 365
Met Arg Gly Arg Pro Pro Thr Phe Gly Gln Gly Thr Lys Val Glu Ile
        370                 375                 380
Lys Ser Ser Ser Ser Gly Ser Ser Ser Gly Ser Ser Ser Gly
385                 390                 395                 400
Val Arg Ser Ser Arg Thr Pro Ser Asp Lys Pro Val Ala His Val
                405                 410                 415
Val Ala Asn Pro Gln Ala Glu Gly Gln Leu Gln Trp Leu Asn Arg Val
                420                 425                 430
Ala Asn Ala Leu Leu Ala Asn Gly Val Glu Leu Arg Asp Asn Gln Leu
                435                 440                 445
Val Val Pro Ser Glu Gly Leu Tyr Leu Ile Tyr Ser Gln Val Leu Phe
        450                 455                 460
Lys Gly Gln Gly Cys Pro Ser Thr His Val Leu Leu Thr His Thr Ile
465                 470                 475                 480
Ser Arg Ile Ala Val Ser Tyr Gln Thr Lys Val Asn Leu Leu Ser Ala
                485                 490                 495
Ile Lys Ser Pro Cys Gln Arg Glu Thr Pro Glu Gly Ala Glu Ala Lys
                500                 505                 510
Pro Trp Tyr Glu Pro Ile Tyr Leu Gly Gly Val Phe Gln Leu Glu Lys
        515                 520                 525
Gly Asp Arg Leu Ser Ala Glu Ile Asn Arg Pro Asp Tyr Leu Asp Phe
        530                 535                 540
Ala Glu Ser Gly Gln Val Tyr Phe Gly Ile Ile Ala Leu
545                 550                 555

<210> SEQ ID NO 63
<211> LENGTH: 577
<212> TYPE: PRT
<213> ORGANISM: Artificial Sequence
<220> FEATURE:
<223> OTHER INFORMATION: Amino acid sequence of the huIL2-F8-huTNalpha
      (R52V) mutant (huTNFalpha R52V) [extracellular domain] conjugate

<400> SEQUENCE: 63

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45

```
Lys Ala Thr Glu Leu Lys His Leu Gln Cys Leu Glu Glu Leu Lys
 50              55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Gly Ser Gly Gly Ala
130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Leu
                165                 170                 175

Phe Thr Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
210                 215                 220

Tyr Leu Gln Met Asn Ser Leu Arg Ala Glu Asp Thr Ala Val Tyr Tyr
225                 230                 235                 240

Cys Ala Lys Ser Thr His Leu Tyr Leu Phe Asp Tyr Trp Gly Gln Gly
                245                 250                 255

Thr Leu Val Thr Val Ser Ser Gly Gly Gly Gly Ser Gly Gly Gly Gly
            260                 265                 270

Ser Gly Gly Gly Gly Glu Ile Val Leu Thr Gln Ser Pro Gly Thr Leu
        275                 280                 285

Ser Leu Ser Pro Gly Glu Arg Ala Thr Leu Ser Cys Arg Ala Ser Gln
290                 295                 300

Ser Val Ser Met Pro Phe Leu Ala Trp Tyr Gln Gln Lys Pro Gly Gln
305                 310                 315                 320

Ala Pro Arg Leu Leu Ile Tyr Gly Ala Ser Ser Arg Ala Thr Gly Ile
                325                 330                 335

Pro Asp Arg Phe Ser Gly Ser Gly Ser Gly Thr Asp Phe Thr Leu Thr
            340                 345                 350

Ile Ser Arg Leu Glu Pro Glu Asp Phe Ala Val Tyr Tyr Cys Gln Gln
        355                 360                 365

Met Arg Gly Arg Pro Pro Thr Phe Gly Gln Gly Thr Lys Val Glu Ile
370                 375                 380

Lys Ser Ser Ser Ser Gly Ser Ser Ser Gly Ser Ser Ser Ser Ser Gly
385                 390                 395                 400

Gly Pro Gln Arg Glu Glu Phe Pro Arg Asp Leu Ser Leu Ile Ser Pro
                405                 410                 415

Leu Ala Gln Ala Val Arg Ser Ser Ser Arg Thr Pro Ser Asp Lys Pro
            420                 425                 430

Val Ala His Val Val Ala Asn Pro Gln Ala Glu Gly Gln Leu Gln Trp
        435                 440                 445

Leu Asn Arg Val Ala Asn Ala Leu Leu Ala Asn Gly Val Glu Leu Arg
450                 455                 460

Asp Asn Gln Leu Val Val Pro Ser Glu Gly Leu Tyr Leu Ile Tyr Ser
```

```
                465                 470                 475                 480
        Gln Val Leu Phe Lys Gly Gln Gly Cys Pro Ser Thr His Val Leu Leu
                            485                 490                 495

Thr His Thr Ile Ser Arg Ile Ala Val Ser Tyr Gln Thr Lys Val Asn
                            500                 505                 510

Leu Leu Ser Ala Ile Lys Ser Pro Cys Gln Arg Glu Thr Pro Glu Gly
                            515                 520                 525

Ala Glu Ala Lys Pro Trp Tyr Glu Pro Ile Tyr Leu Gly Gly Val Phe
                            530                 535                 540

Gln Leu Glu Lys Gly Asp Arg Leu Ser Ala Glu Ile Asn Arg Pro Asp
        545                 550                 555                 560

Tyr Leu Asp Phe Ala Glu Ser Gly Gln Val Tyr Phe Gly Ile Ile Ala
                            565                 570                 575

Leu

<210> SEQ ID NO 64
<211> LENGTH: 555
<212> TYPE: PRT
<213> ORGANISM: Artificial Sequence
<220> FEATURE:
<223> OTHER INFORMATION: Amino acid sequence of the huIL2-L19-huTNFalpha
      (R32W) mutant [soluble form] conjugate

<400> SEQUENCE: 64

Ala Pro Thr Ser Ser Ser Thr Lys Lys Thr Gln Leu Gln Leu Glu His
        1               5                   10                  15

Leu Leu Leu Asp Leu Gln Met Ile Leu Asn Gly Ile Asn Asn Tyr Lys
                        20                  25                  30

Asn Pro Lys Leu Thr Arg Met Leu Thr Phe Lys Phe Tyr Met Pro Lys
                    35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
        65                  70                  75                  80

Arg Pro Arg Asp Leu Ile Ser Asn Ile Asn Val Ile Val Leu Glu Leu
                            85                  90                  95

Lys Gly Ser Glu Thr Thr Phe Met Cys Glu Tyr Ala Asp Glu Thr Ala
                        100                 105                 110

Thr Ile Val Glu Phe Leu Asn Arg Trp Ile Thr Phe Cys Gln Ser Ile
                    115                 120                 125

Ile Ser Thr Leu Thr Gly Gly Gly Gly Ser Gly Gly Gly Ser Gly
                130                 135                 140

Gly Gly Gly Glu Val Gln Leu Leu Glu Ser Gly Gly Gly Leu Val Gln
        145                 150                 155                 160

Pro Gly Gly Ser Leu Arg Leu Ser Cys Ala Ala Ser Gly Phe Thr Phe
                            165                 170                 175

Ser Ser Phe Ser Met Ser Trp Val Arg Gln Ala Pro Gly Lys Gly Leu
                        180                 185                 190

Glu Trp Val Ser Ser Ile Ser Gly Ser Ser Gly Thr Thr Tyr Tyr Ala
                    195                 200                 205

Asp Ser Val Lys Gly Arg Phe Thr Ile Ser Arg Asp Asn Ser Lys Asn
                210                 215                 220

Thr Leu Tyr Leu Gln Met Asn Ser Leu Arg Ala Glu Asp Thr Ala Val
        225                 230                 235                 240

Tyr Tyr Cys Ala Lys Pro Phe Pro Tyr Phe Asp Tyr Trp Gly Gln Gly
```

```
                   245                 250                 255
Thr Leu Val Thr Val Ser Ser Gly Asp Gly Ser Ser Gly Ser Gly
               260                 265                 270

Gly Ala Ser Glu Ile Val Leu Thr Gln Ser Pro Gly Thr Leu Ser Leu
           275                 280                 285

Ser Pro Gly Glu Arg Ala Thr Leu Ser Cys Arg Ala Ser Gln Ser Val
       290                 295                 300

Ser Ser Ser Phe Leu Ala Trp Tyr Gln Lys Pro Gly Gln Ala Pro
305                 310                 315                 320

Arg Leu Leu Ile Tyr Tyr Ala Ser Ser Arg Ala Thr Gly Ile Pro Asp
               325                 330                 335

Arg Phe Ser Gly Ser Gly Ser Gly Thr Asp Phe Thr Leu Thr Ile Ser
           340                 345                 350

Arg Leu Glu Pro Glu Asp Phe Ala Val Tyr Tyr Cys Gln Gln Thr Gly
       355                 360                 365

Arg Ile Pro Pro Thr Phe Gly Gln Gly Thr Lys Val Glu Ile Lys Ser
   370                 375                 380

Ser Ser Ser Gly Ser Ser Ser Gly Ser Ser Ser Gly Val Arg
385                 390                 395                 400

Ser Ser Ser Arg Thr Pro Ser Asp Lys Pro Val Ala His Val Val Ala
               405                 410                 415

Asn Pro Gln Ala Glu Gly Gln Leu Gln Trp Leu Asn Arg Trp Ala Asn
           420                 425                 430

Ala Leu Leu Ala Asn Gly Val Glu Leu Arg Asp Asn Gln Leu Val Val
       435                 440                 445

Pro Ser Glu Gly Leu Tyr Leu Ile Tyr Ser Gln Val Leu Phe Lys Gly
   450                 455                 460

Gln Gly Cys Pro Ser Thr His Val Leu Leu Thr His Thr Ile Ser Arg
465                 470                 475                 480

Ile Ala Val Ser Tyr Gln Thr Lys Val Asn Leu Leu Ser Ala Ile Lys
               485                 490                 495

Ser Pro Cys Gln Arg Glu Thr Pro Glu Gly Ala Glu Ala Lys Pro Trp
           500                 505                 510

Tyr Glu Pro Ile Tyr Leu Gly Gly Val Phe Gln Leu Glu Lys Gly Asp
       515                 520                 525

Arg Leu Ser Ala Glu Ile Asn Arg Pro Asp Tyr Leu Asp Phe Ala Glu
   530                 535                 540

Ser Gly Gln Val Tyr Phe Gly Ile Ile Ala Leu
545                 550                 555

<210> SEQ ID NO 65
<211> LENGTH: 575
<212> TYPE: PRT
<213> ORGANISM: Artificial Sequence
<220> FEATURE:
<223> OTHER INFORMATION: Amino acid sequence of the huIL2-L19-huTNFalpha
      (R52W) mutant [extracellular domain] conjugate

<400> SEQUENCE: 65

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
               20                  25                  30

Asn Pro Lys Leu Thr Arg Met Leu Thr Phe Lys Phe Tyr Met Pro Lys
           35                  40                  45
```

-continued

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Phe Ser Met Ser Trp Val Arg Gln Ala Pro Gly Lys Gly Leu
            180                 185                 190

Glu Trp Val Ser Ser Ile Ser Gly Ser Ser Gly Thr Thr Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Gly Ser Gly
            260                 265                 270

Gly Ala Ser Glu Ile Val Leu Thr Gln Ser Pro Gly Thr Leu Ser Leu
        275                 280                 285

Ser Pro Gly Glu Arg Ala Thr Leu Ser Cys Arg Ala Ser Gln Ser Val
    290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
                325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
        355                 360                 365

Arg Ile Pro Pro Thr Phe Gly Gln Gly Thr Lys Val Glu Ile Lys Ser
    370                 375                 380

Ser Ser Ser Gly Ser Ser Ser Gly Ser Ser Ser Gly Gly Pro
385                 390                 395                 400

Gln Arg Glu Glu Phe Pro Arg Asp Leu Ser Leu Ile Ser Pro Leu Ala
                405                 410                 415

Gln Ala Val Arg Ser Ser Ser Arg Thr Pro Ser Asp Lys Pro Val Ala
            420                 425                 430

His Val Val Ala Asn Pro Gln Ala Glu Gly Gln Leu Gln Trp Leu Asn
        435                 440                 445

Arg Trp Ala Asn Ala Leu Leu Ala Asn Gly Val Glu Leu Arg Asp Asn
    450                 455                 460

Gln Leu Val Val Pro Ser Glu Gly Leu Tyr Leu Ile Tyr Ser Gln Val
```

```
                    465                 470                 475                 480
        Leu Phe Lys Gly Gln Gly Cys Pro Ser Thr His Val Leu Leu Thr His
                        485                 490                 495

Thr Ile Ser Arg Ile Ala Val Ser Tyr Gln Thr Lys Val Asn Leu Leu
                        500                 505                 510

Ser Ala Ile Lys Ser Pro Cys Gln Arg Glu Thr Pro Glu Gly Ala Glu
                        515                 520                 525

Ala Lys Pro Trp Tyr Glu Pro Ile Tyr Leu Gly Gly Val Phe Gln Leu
                        530                 535                 540

Glu Lys Gly Asp Arg Leu Ser Ala Glu Ile Asn Arg Pro Asp Tyr Leu
        545                 550                 555                 560

Asp Phe Ala Glu Ser Gly Gln Val Tyr Phe Gly Ile Ile Ala Leu
                        565                 570                 575

<210> SEQ ID NO 66
<211> LENGTH: 555
<212> TYPE: PRT
<213> ORGANISM: Artificial Sequence
<220> FEATURE:
<223> OTHER INFORMATION: Amino acid sequence of the huIL2-L19-huTNFalpha
      (R32F) mutant [soluble form] conjugate

<400> SEQUENCE: 66

Ala Pro Thr Ser Ser Ser Thr Lys Lys Thr Gln Leu Gln Leu Glu His
        1               5                   10                  15

Leu Leu Leu Asp Leu Gln Met Ile Leu Asn Gly Ile Asn Asn Tyr Lys
                        20                  25                  30

Asn Pro Lys Leu Thr Arg Met Leu Thr Phe Lys Phe Tyr Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
        65                  70                  75                  80

Arg Pro Arg Asp Leu Ile Ser Asn Ile Asn Val Ile Val Leu Glu Leu
                        85                  90                  95

Lys Gly Ser Glu Thr Thr Phe Met Cys Glu Tyr Ala Asp Glu Thr Ala
                        100                 105                 110

Thr Ile Val Glu Phe Leu Asn Arg Trp Ile Thr Phe Cys Gln Ser Ile
                        115                 120                 125

Ile Ser Thr Leu Thr Gly Gly Gly Gly Ser Gly Gly Gly Ser Gly
        130                 135                 140

Gly Gly Gly Glu Val Gln Leu Leu Glu Ser Gly Gly Gly Leu Val Gln
        145                 150                 155                 160

Pro Gly Gly Ser Leu Arg Leu Ser Cys Ala Ala Ser Gly Phe Thr Phe
                        165                 170                 175

Ser Ser Phe Ser Met Ser Trp Val Arg Gln Ala Pro Gly Lys Gly Leu
                        180                 185                 190

Glu Trp Val Ser Ser Ile Ser Gly Ser Ser Gly Thr Thr Tyr Tyr Ala
                        195                 200                 205

Asp Ser Val Lys Gly Arg Phe Thr Ile Ser Arg Asp Asn Ser Lys Asn
                        210                 215                 220

Thr Leu Tyr Leu Gln Met Asn Ser Leu Arg Ala Glu Asp Thr Ala Val
        225                 230                 235                 240

Tyr Tyr Cys Ala Lys Pro Phe Pro Tyr Phe Asp Tyr Trp Gly Gln Gly
                        245                 250                 255
```

```
Thr Leu Val Thr Val Ser Ser Gly Asp Gly Ser Ser Gly Gly Ser Gly
                260                 265                 270

Gly Ala Ser Glu Ile Val Leu Thr Gln Ser Pro Gly Thr Leu Ser Leu
            275                 280                 285

Ser Pro Gly Glu Arg Ala Thr Leu Ser Cys Arg Ala Ser Gln Ser Val
        290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
                325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
        355                 360                 365

Arg Ile Pro Pro Thr Phe Gly Gln Gly Thr Lys Val Glu Ile Lys Ser
        370                 375                 380

Ser Ser Ser Gly Ser Ser Ser Gly Ser Ser Ser Gly Val Arg
385                 390                 395                 400

Ser Ser Ser Arg Thr Pro Ser Asp Lys Pro Val Ala His Val Val Ala
            405                 410                 415

Asn Pro Gln Ala Glu Gly Gln Leu Gln Trp Leu Asn Arg Phe Ala Asn
            420                 425                 430

Ala Leu Leu Ala Asn Gly Val Glu Leu Arg Asp Asn Gln Leu Val Val
        435                 440                 445

Pro Ser Glu Gly Leu Tyr Leu Ile Tyr Ser Gln Val Leu Phe Lys Gly
        450                 455                 460

Gln Gly Cys Pro Ser Thr His Val Leu Leu Thr His Thr Ile Ser Arg
465                 470                 475                 480

Ile Ala Val Ser Tyr Gln Thr Lys Val Asn Leu Leu Ser Ala Ile Lys
                485                 490                 495

Ser Pro Cys Gln Arg Glu Thr Pro Glu Gly Ala Glu Ala Lys Pro Trp
            500                 505                 510

Tyr Glu Pro Ile Tyr Leu Gly Gly Val Phe Gln Leu Glu Lys Gly Asp
        515                 520                 525

Arg Leu Ser Ala Glu Ile Asn Arg Pro Asp Tyr Leu Asp Phe Ala Glu
    530                 535                 540

Ser Gly Gln Val Tyr Phe Gly Ile Ile Ala Leu
545                 550                 555

<210> SEQ ID NO 67
<211> LENGTH: 575
<212> TYPE: PRT
<213> ORGANISM: Artificial Sequence
<220> FEATURE:
<223> OTHER INFORMATION: Amino acid sequence of the huIL2-L19-huTNFalpha
      (R52F) mutant [extracellular domain] conjugate

<400> SEQUENCE: 67

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60
```

-continued

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly
    130                 135                 140

Gly Gly Gly Glu Val Gln Leu Leu Glu Ser Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Phe Ser Met Ser Trp Val Arg Gln Ala Pro Gly Lys Gly Leu
            180                 185                 190

Glu Trp Val Ser Ser Ile Ser Gly Ser Ser Gly Thr Thr Tyr Tyr Ala
    195                 200                 205

Asp Ser Val Lys Gly Arg Phe Thr Ile Ser Arg Asp Asn Ser Lys Asn
210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Ser Gly
            260                 265                 270

Gly Ala Ser Glu Ile Val Leu Thr Gln Ser Pro Gly Thr Leu Ser Leu
        275                 280                 285

Ser Pro Gly Glu Arg Ala Thr Leu Ser Cys Arg Ala Ser Gln Ser Val
290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
                325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
        355                 360                 365

Arg Ile Pro Pro Thr Phe Gly Gln Gly Thr Lys Val Glu Ile Lys Ser
    370                 375                 380

Ser Ser Ser Gly Ser Ser Ser Gly Ser Ser Ser Gly Gly Pro
385                 390                 395                 400

Gln Arg Glu Glu Phe Pro Arg Asp Leu Ser Leu Ile Ser Pro Leu Ala
                405                 410                 415

Gln Ala Val Arg Ser Ser Arg Thr Pro Ser Asp Lys Pro Val Ala
            420                 425                 430

His Val Val Ala Asn Pro Gln Ala Glu Gly Gln Leu Gln Trp Leu Asn
        435                 440                 445

Arg Phe Ala Asn Ala Leu Leu Ala Asn Gly Val Glu Leu Arg Asp Asn
    450                 455                 460

Gln Leu Val Val Pro Ser Glu Gly Leu Tyr Leu Ile Tyr Ser Gln Val
465                 470                 475                 480

```
Leu Phe Lys Gly Gln Gly Cys Pro Ser Thr His Val Leu Leu Thr His
                485                 490                 495

Thr Ile Ser Arg Ile Ala Val Ser Tyr Gln Thr Lys Val Asn Leu Leu
            500                 505                 510

Ser Ala Ile Lys Ser Pro Cys Gln Arg Glu Thr Pro Glu Gly Ala Glu
            515                 520                 525

Ala Lys Pro Trp Tyr Glu Pro Ile Tyr Leu Gly Gly Val Phe Gln Leu
        530                 535                 540

Glu Lys Gly Asp Arg Leu Ser Ala Glu Ile Asn Arg Pro Asp Tyr Leu
545                 550                 555                 560

Asp Phe Ala Glu Ser Gly Gln Val Tyr Phe Gly Ile Ile Ala Leu
                565                 570                 575

<210> SEQ ID NO 68
<211> LENGTH: 555
<212> TYPE: PRT
<213> ORGANISM: Artificial Sequence
<220> FEATURE:
<223> OTHER INFORMATION: Amino acid sequence of the huIL2-L19-huTNFalpha
      (R32V) mutant [soluble form] conjugate

<400> SEQUENCE: 68

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Phe Ser Met Ser Trp Val Arg Gln Ala Pro Gly Lys Gly Leu
            180                 185                 190

Glu Trp Val Ser Ser Ile Ser Gly Ser Ser Gly Thr Thr Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Gly Ser Gly
            260                 265                 270
```

Gly Ala Ser Glu Ile Val Leu Thr Gln Ser Pro Gly Thr Leu Ser Leu
            275                 280                 285

Ser Pro Gly Glu Arg Ala Thr Leu Ser Cys Arg Ala Ser Gln Ser Val
290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
            325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
            355                 360                 365

Arg Ile Pro Pro Thr Phe Gly Gln Gly Thr Lys Val Glu Ile Lys Ser
            370                 375                 380

Ser Ser Ser Gly Ser Ser Ser Gly Ser Ser Ser Gly Val Arg
385                 390                 395                 400

Ser Ser Ser Arg Thr Pro Ser Asp Lys Pro Val Ala His Val Val Ala
            405                 410                 415

Asn Pro Gln Ala Glu Gly Gln Leu Gln Trp Leu Asn Arg Val Ala Asn
            420                 425                 430

Ala Leu Leu Ala Asn Gly Val Glu Leu Arg Asp Asn Gln Leu Val Val
            435                 440                 445

Pro Ser Glu Gly Leu Tyr Leu Ile Tyr Ser Gln Val Leu Phe Lys Gly
450                 455                 460

Gln Gly Cys Pro Ser Thr His Val Leu Leu Thr His Thr Ile Ser Arg
465                 470                 475                 480

Ile Ala Val Ser Tyr Gln Thr Lys Val Asn Leu Leu Ser Ala Ile Lys
            485                 490                 495

Ser Pro Cys Gln Arg Glu Thr Pro Glu Gly Ala Glu Ala Lys Pro Trp
            500                 505                 510

Tyr Glu Pro Ile Tyr Leu Gly Gly Val Phe Gln Leu Glu Lys Gly Asp
            515                 520                 525

Arg Leu Ser Ala Glu Ile Asn Arg Pro Asp Tyr Leu Asp Phe Ala Glu
            530                 535                 540

Ser Gly Gln Val Tyr Phe Gly Ile Ile Ala Leu
545                 550                 555

<210> SEQ ID NO 69
<211> LENGTH: 575
<212> TYPE: PRT
<213> ORGANISM: Artificial Sequence
<220> FEATURE:
<223> OTHER INFORMATION: Amino acid sequence of the huIL2-L19-huTNFalpha
      (R52V) mutant [extracellular domain] conjugate

<400> SEQUENCE: 69

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu

-continued

```
              65                  70                  75                  80
         Arg Pro Arg Asp Leu Ile Ser Asn Ile Asn Val Ile Val Leu Glu Leu
                         85                  90                  95

Lys Gly Ser Glu Thr Thr Phe Met Cys Glu Tyr Ala Asp Glu Thr Ala
                         100                 105                 110

Thr Ile Val Glu Phe Leu Asn Arg Trp Ile Thr Phe Cys Gln Ser Ile
                         115                 120                 125

Ile Ser Thr Leu Thr Gly Gly Gly Ser Gly Gly Gly Ser Gly
             130                 135                 140

Gly Gly Gly Glu Val Gln Leu Leu Glu Ser Gly Gly Leu Val Gln
         145                 150                 155                 160

Pro Gly Gly Ser Leu Arg Leu Ser Cys Ala Ala Ser Gly Phe Thr Phe
                         165                 170                 175

Ser Ser Phe Ser Met Ser Trp Val Arg Gln Ala Pro Lys Gly Leu
                     180                 185                 190

Glu Trp Val Ser Ser Ile Ser Gly Ser Ser Gly Thr Thr Tyr Tyr Ala
                         195                 200                 205

Asp Ser Val Lys Gly Arg Phe Thr Ile Ser Arg Asp Asn Ser Lys Asn
             210                 215                 220

Thr Leu Tyr Leu Gln Met Asn Ser Leu Arg Ala Glu Asp Thr Ala Val
         225                 230                 235                 240

Tyr Tyr Cys Ala Lys Pro Phe Pro Tyr Phe Asp Tyr Trp Gly Gln Gly
                         245                 250                 255

Thr Leu Val Thr Val Ser Ser Gly Asp Gly Ser Ser Gly Gly Ser Gly
                         260                 265                 270

Gly Ala Ser Glu Ile Val Leu Thr Gln Ser Pro Gly Thr Leu Ser Leu
                     275                 280                 285

Ser Pro Gly Glu Arg Ala Thr Leu Ser Cys Arg Ala Ser Gln Ser Val
                     290                 295                 300

Ser Ser Ser Phe Leu Ala Trp Tyr Gln Gln Lys Pro Gly Gln Ala Pro
         305                 310                 315                 320

Arg Leu Leu Ile Tyr Tyr Ala Ser Ser Arg Ala Thr Gly Ile Pro Asp
                         325                 330                 335

Arg Phe Ser Gly Ser Gly Ser Gly Thr Asp Phe Thr Leu Thr Ile Ser
                         340                 345                 350

Arg Leu Glu Pro Glu Asp Phe Ala Val Tyr Tyr Cys Gln Gln Thr Gly
                         355                 360                 365

Arg Ile Pro Pro Thr Phe Gly Gln Gly Thr Lys Val Glu Ile Lys Ser
             370                 375                 380

Ser Ser Ser Gly Ser Ser Ser Gly Ser Ser Ser Gly Gly Pro
         385                 390                 395                 400

Gln Arg Glu Glu Phe Pro Arg Asp Leu Ser Leu Ile Ser Pro Leu Ala
                         405                 410                 415

Gln Ala Val Arg Ser Ser Ser Arg Thr Pro Ser Asp Lys Pro Val Ala
                         420                 425                 430

His Val Val Ala Asn Pro Gln Ala Glu Gly Gln Leu Gln Trp Leu Asn
                     435                 440                 445

Arg Val Ala Asn Ala Leu Leu Ala Asn Gly Val Glu Leu Arg Asp Asn
         450                 455                 460

Gln Leu Val Val Pro Ser Glu Gly Leu Tyr Leu Ile Tyr Ser Gln Val
         465                 470                 475                 480

Leu Phe Lys Gly Gln Gly Cys Pro Ser Thr His Val Leu Leu Thr His
                         485                 490                 495
```

```
Thr Ile Ser Arg Ile Ala Val Ser Tyr Gln Thr Lys Val Asn Leu Leu
            500                 505                 510

Ser Ala Ile Lys Ser Pro Cys Gln Arg Glu Thr Pro Glu Gly Ala Glu
            515                 520                 525

Ala Lys Pro Trp Tyr Glu Pro Ile Tyr Leu Gly Gly Val Phe Gln Leu
            530                 535                 540

Glu Lys Gly Asp Arg Leu Ser Ala Glu Ile Asn Arg Pro Asp Tyr Leu
545                 550                 555                 560

Asp Phe Ala Glu Ser Gly Gln Val Tyr Phe Gly Ile Ile Ala Leu
            565                 570                 575

<210> SEQ ID NO 70
<211> LENGTH: 555
<212> TYPE: PRT
<213> ORGANISM: Artificial Sequence
<220> FEATURE:
<223> OTHER INFORMATION: Amino acid sequence of the huIL2-L19-huTNFalpha
      [soluble form] conjugate

<400> SEQUENCE: 70

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Gly Ser Gly
            130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Phe Ser Met Ser Trp Val Arg Gln Ala Pro Gly Lys Gly Leu
            180                 185                 190

Glu Trp Val Ser Ser Ile Ser Gly Ser Ser Gly Thr Thr Tyr Tyr Ala
            195                 200                 205

Asp Ser Val Lys Gly Arg Phe Thr Ile Ser Arg Asp Asn Ser Lys Asn
            210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Gly Ser Gly
            260                 265                 270

Gly Ala Ser Glu Ile Val Leu Thr Gln Ser Pro Gly Thr Leu Ser Leu
```

-continued

```
                275                 280                 285
Ser Pro Gly Glu Arg Ala Thr Leu Ser Cys Arg Ala Ser Gln Ser Val
290                 295                 300
Ser Ser Ser Phe Leu Ala Trp Tyr Gln Gln Lys Pro Gly Gln Ala Pro
305                 310                 315                 320
Arg Leu Leu Ile Tyr Tyr Ala Ser Ser Arg Ala Thr Gly Ile Pro Asp
                325                 330                 335
Arg Phe Ser Gly Ser Gly Ser Gly Thr Asp Phe Thr Leu Thr Ile Ser
                340                 345                 350
Arg Leu Glu Pro Glu Asp Phe Ala Val Tyr Tyr Cys Gln Gln Thr Gly
                355                 360                 365
Arg Ile Pro Pro Thr Phe Gly Gln Gly Thr Lys Val Glu Ile Lys Ser
                370                 375                 380
Ser Ser Ser Gly Ser Ser Ser Gly Ser Ser Ser Gly Val Arg
385                 390                 395                 400
Ser Ser Ser Arg Thr Pro Ser Asp Lys Pro Val Ala His Val Val Ala
                405                 410                 415
Asn Pro Gln Ala Glu Gly Gln Leu Gln Trp Leu Asn Arg Arg Ala Asn
                420                 425                 430
Ala Leu Leu Ala Asn Gly Val Glu Leu Arg Asp Asn Gln Leu Val Val
                435                 440                 445
Pro Ser Glu Gly Leu Tyr Leu Ile Tyr Ser Gln Val Leu Phe Lys Gly
                450                 455                 460
Gln Gly Cys Pro Ser Thr His Val Leu Leu Thr His Thr Ile Ser Arg
465                 470                 475                 480
Ile Ala Val Ser Tyr Gln Thr Lys Val Asn Leu Leu Ser Ala Ile Lys
                485                 490                 495
Ser Pro Cys Gln Arg Glu Thr Pro Glu Gly Ala Glu Ala Lys Pro Trp
                500                 505                 510
Tyr Glu Pro Ile Tyr Leu Gly Gly Val Phe Gln Leu Glu Lys Gly Asp
                515                 520                 525
Arg Leu Ser Ala Glu Ile Asn Arg Pro Asp Tyr Leu Asp Phe Ala Glu
530                 535                 540
Ser Gly Gln Val Tyr Phe Gly Ile Ile Ala Leu
545                 550                 555
```

<210> SEQ ID NO 71
<211> LENGTH: 575
<212> TYPE: PRT
<213> ORGANISM: Artificial Sequence
<220> FEATURE:
<223> OTHER INFORMATION: Amino acid sequence of the huIL2-L19-huTNFalpha
      [extracellular domain] conjugate

<400> SEQUENCE: 71

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
                50                  55                  60
Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Phe Ser Met Ser Trp Val Arg Gln Ala Pro Gly Lys Gly Leu
            180                 185                 190

Glu Trp Val Ser Ser Ile Ser Gly Ser Ser Gly Thr Thr Tyr Tyr Ala
        195                 200                 205

Asp Ser Val Lys Gly Arg Phe Thr Ile Ser Arg Asp Asn Ser Lys Asn
    210                 215                 220

Thr Leu Tyr Leu Gln Met Asn Ser Leu Arg Ala Glu Asp Thr Ala Val
225                 230                 235                 240

Tyr Tyr Cys Ala Lys Pro Phe Pro Tyr Phe Asp Tyr Trp Gly Gln Gly
                245                 250                 255

Thr Leu Val Thr Val Ser Ser Gly Asp Gly Ser Ser Gly Ser Ser Gly
            260                 265                 270

Gly Ala Ser Glu Ile Val Leu Thr Gln Ser Pro Gly Thr Leu Ser Leu
    275                 280                 285

Ser Pro Gly Glu Arg Ala Thr Leu Ser Cys Arg Ala Ser Gln Ser Val
290                 295                 300

Ser Ser Ser Phe Leu Ala Trp Tyr Gln Gln Lys Pro Gly Gln Ala Pro
305                 310                 315                 320

Arg Leu Leu Ile Tyr Tyr Ala Ser Ser Arg Ala Thr Gly Ile Pro Asp
                325                 330                 335

Arg Phe Ser Gly Ser Gly Ser Gly Thr Asp Phe Thr Leu Thr Ile Ser
            340                 345                 350

Arg Leu Glu Pro Glu Asp Phe Ala Val Tyr Tyr Cys Gln Gln Thr Gly
        355                 360                 365

Arg Ile Pro Pro Thr Phe Gly Gln Gly Thr Lys Val Glu Ile Lys Ser
    370                 375                 380

Ser Ser Ser Gly Ser Ser Ser Gly Ser Ser Ser Gly Gly Pro
385                 390                 395                 400

Gln Arg Glu Glu Phe Pro Arg Asp Leu Ser Leu Ile Ser Pro Leu Ala
                405                 410                 415

Gln Ala Val Arg Ser Ser Ser Arg Thr Pro Ser Asp Lys Pro Val Ala
            420                 425                 430

His Val Val Ala Asn Pro Gln Ala Glu Gly Gln Leu Gln Trp Leu Asn
        435                 440                 445

Arg Arg Ala Asn Ala Leu Leu Ala Asn Gly Val Glu Leu Arg Asp Asn
    450                 455                 460

Gln Leu Val Val Pro Ser Glu Gly Leu Tyr Leu Ile Tyr Ser Gln Val
465                 470                 475                 480

Leu Phe Lys Gly Gln Gly Cys Pro Ser Thr His Val Leu Leu Thr His
                485                 490                 495

Thr Ile Ser Arg Ile Ala Val Ser Tyr Gln Thr Lys Val Asn Leu Leu
```

```
                500             505             510
Ser Ala Ile Lys Ser Pro Cys Gln Arg Glu Thr Pro Glu Gly Ala Glu
            515                 520             525

Ala Lys Pro Trp Tyr Glu Pro Ile Tyr Leu Gly Gly Val Phe Gln Leu
            530                 535             540

Glu Lys Gly Asp Arg Leu Ser Ala Glu Ile Asn Arg Pro Asp Tyr Leu
545                 550                 555                 560

Asp Phe Ala Glu Ser Gly Gln Val Tyr Phe Gly Ile Ile Ala Leu
                565                 570             575

<210> SEQ ID NO 72
<211> LENGTH: 556
<212> TYPE: PRT
<213> ORGANISM: Artificial Sequence
<220> FEATURE:
<223> OTHER INFORMATION: Amino acid sequence of the huIL2-F16-huTNFalpha
      (R32W) mutant [soluble form] conjugate

<400> SEQUENCE: 72

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Gly Ser Gly Gly Ala
        130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
        210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
                245                 250                 255

Val Thr Val Ser Arg Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
            275                 280                 285
```

-continued

```
Leu Gly Gln Thr Val Arg Ile Thr Cys Gln Gly Asp Ser Leu Arg Ser
290                 295                 300
Tyr Tyr Ala Ser Trp Tyr Gln Gln Lys Pro Gly Gln Ala Pro Val Leu
305                 310                 315                 320
Val Ile Tyr Gly Lys Asn Asn Arg Pro Ser Gly Ile Pro Asp Arg Phe
            325                 330                 335
Ser Gly Ser Ser Ser Gly Asn Thr Ala Ser Leu Thr Ile Thr Gly Ala
        340                 345                 350
Gln Ala Glu Asp Glu Ala Asp Tyr Tyr Cys Asn Ser Ser Val Tyr Thr
    355                 360                 365
Met Pro Pro Val Val Phe Gly Gly Thr Lys Leu Thr Val Leu Gly
370                 375                 380
Ser Ser Ser Ser Gly Ser Ser Ser Gly Ser Ser Ser Gly Val
385                 390                 395                 400
Arg Ser Ser Arg Thr Pro Ser Asp Lys Pro Val Ala His Val Val
            405                 410                 415
Ala Asn Pro Gln Ala Glu Gly Gln Leu Gln Trp Leu Asn Arg Trp Ala
        420                 425                 430
Asn Ala Leu Leu Ala Asn Gly Val Glu Leu Arg Asp Asn Gln Leu Val
    435                 440                 445
Val Pro Ser Glu Gly Leu Tyr Leu Ile Tyr Ser Gln Val Leu Phe Lys
450                 455                 460
Gly Gln Gly Cys Pro Ser Thr His Val Leu Leu Thr His Thr Ile Ser
465                 470                 475                 480
Arg Ile Ala Val Ser Tyr Gln Thr Lys Val Asn Leu Leu Ser Ala Ile
            485                 490                 495
Lys Ser Pro Cys Gln Arg Glu Thr Pro Glu Gly Ala Glu Ala Lys Pro
        500                 505                 510
Trp Tyr Glu Pro Ile Tyr Leu Gly Gly Val Phe Gln Leu Glu Lys Gly
    515                 520                 525
Asp Arg Leu Ser Ala Glu Ile Asn Arg Pro Asp Tyr Leu Asp Phe Ala
530                 535                 540
Glu Ser Gly Gln Val Tyr Phe Gly Ile Ile Ala Leu
545                 550                 555

<210> SEQ ID NO 73
<211> LENGTH: 576
<212> TYPE: PRT
<213> ORGANISM: Artificial Sequence
<220> FEATURE:
<223> OTHER INFORMATION: Amino acid sequence of the huIL2-F16-huTNFalpha
      (R52W) mutant [extracellular domain] conjugate

<400> SEQUENCE: 73

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
            85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Asp Gly Ser Ser Gly Gly Ser Gly Gly Ala
            130                 135                 140

Ser Glu Val Gln Leu Leu Glu Ser Gly Gly Leu Val Gln Pro Gly
145                 150                 155                 160

Gly Ser Leu Arg Leu Ser Cys Ala Ala Ser Gly Phe Thr Phe Ser Arg
            165                 170                 175

Tyr Gly Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
            195                 200                 205

Val Lys Gly Arg Phe Thr Ile Ser Arg Asp Asn Ser Lys Asn Thr Leu
            210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
            245                 250                 255

Val Thr Val Ser Arg Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
            275                 280                 285

Leu Gly Gln Thr Val Arg Ile Thr Cys Gln Gly Asp Ser Leu Arg Ser
            290                 295                 300

Tyr Tyr Ala Ser Trp Tyr Gln Gln Lys Pro Gly Gln Ala Pro Val Leu
305                 310                 315                 320

Val Ile Tyr Gly Lys Asn Asn Arg Pro Ser Gly Ile Pro Asp Arg Phe
            325                 330                 335

Ser Gly Ser Ser Ser Gly Asn Thr Ala Ser Leu Thr Ile Thr Gly Ala
            340                 345                 350

Gln Ala Glu Asp Glu Ala Asp Tyr Tyr Cys Asn Ser Ser Val Tyr Thr
            355                 360                 365

Met Pro Pro Val Val Phe Gly Gly Gly Thr Lys Leu Thr Val Leu Gly
            370                 375                 380

Ser Ser Ser Ser Gly Ser Ser Ser Gly Ser Ser Ser Gly Gly
385                 390                 395                 400

Pro Gln Arg Glu Glu Phe Pro Arg Asp Leu Ser Leu Ile Ser Pro Leu
            405                 410                 415

Ala Gln Ala Val Arg Ser Ser Ser Arg Thr Pro Ser Asp Lys Pro Val
            420                 425                 430

Ala His Val Val Ala Asn Pro Gln Ala Glu Gly Gln Leu Gln Trp Leu
            435                 440                 445

Asn Arg Trp Ala Asn Ala Leu Leu Ala Asn Gly Val Glu Leu Arg Asp
            450                 455                 460

Asn Gln Leu Val Val Pro Ser Glu Gly Leu Tyr Leu Ile Tyr Ser Gln
465                 470                 475                 480

Val Leu Phe Lys Gly Gln Gly Cys Pro Ser Thr His Val Leu Leu Thr
            485                 490                 495

His Thr Ile Ser Arg Ile Ala Val Ser Tyr Gln Thr Lys Val Asn Leu
            500                 505                 510
```

Leu Ser Ala Ile Lys Ser Pro Cys Gln Arg Glu Thr Pro Glu Gly Ala
            515                 520                 525

Glu Ala Lys Pro Trp Tyr Glu Pro Ile Tyr Leu Gly Gly Val Phe Gln
        530                 535                 540

Leu Glu Lys Gly Asp Arg Leu Ser Ala Glu Ile Asn Arg Pro Asp Tyr
545                 550                 555                 560

Leu Asp Phe Ala Glu Ser Gly Gln Val Tyr Phe Gly Ile Ile Ala Leu
                565                 570                 575

<210> SEQ ID NO 74
<211> LENGTH: 556
<212> TYPE: PRT
<213> ORGANISM: Artificial Sequence
<220> FEATURE:
<223> OTHER INFORMATION: Amino acid sequence of the huIL2-F16-huTNFalpha
      (R32F) mutant [soluble form] conjugate

<400> SEQUENCE: 74

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
                245                 250                 255

Val Thr Val Ser Arg Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
        275                 280                 285

Leu Gly Gln Thr Val Arg Ile Thr Cys Gln Gly Asp Ser Leu Arg Ser
    290                 295                 300

```
Tyr Tyr Ala Ser Trp Tyr Gln Gln Lys Pro Gly Gln Ala Pro Val Leu
305                 310                 315                 320

Val Ile Tyr Gly Lys Asn Asn Arg Pro Ser Gly Ile Pro Asp Arg Phe
            325                 330                 335

Ser Gly Ser Ser Ser Gly Asn Thr Ala Ser Leu Thr Ile Thr Gly Ala
        340                 345                 350

Gln Ala Glu Asp Glu Ala Asp Tyr Tyr Cys Asn Ser Ser Val Tyr Thr
            355                 360                 365

Met Pro Pro Val Val Phe Gly Gly Thr Lys Leu Thr Val Leu Gly
        370                 375                 380

Ser Ser Ser Ser Gly Ser Ser Ser Gly Ser Ser Ser Gly Val
385                 390                 395                 400

Arg Ser Ser Arg Thr Pro Ser Asp Lys Pro Val Ala His Val Val
                405                 410                 415

Ala Asn Pro Gln Ala Glu Gly Gln Leu Gln Trp Leu Asn Arg Phe Ala
            420                 425                 430

Asn Ala Leu Leu Ala Asn Gly Val Glu Leu Arg Asp Asn Gln Leu Val
                435                 440                 445

Val Pro Ser Glu Gly Leu Tyr Leu Ile Tyr Ser Gln Val Leu Phe Lys
        450                 455                 460

Gly Gln Gly Cys Pro Ser Thr His Val Leu Leu Thr His Thr Ile Ser
465                 470                 475                 480

Arg Ile Ala Val Ser Tyr Gln Thr Lys Val Asn Leu Leu Ser Ala Ile
            485                 490                 495

Lys Ser Pro Cys Gln Arg Glu Thr Pro Glu Gly Ala Glu Ala Lys Pro
                500                 505                 510

Trp Tyr Glu Pro Ile Tyr Leu Gly Gly Val Phe Gln Leu Glu Lys Gly
            515                 520                 525

Asp Arg Leu Ser Ala Glu Ile Asn Arg Pro Asp Tyr Leu Asp Phe Ala
        530                 535                 540

Glu Ser Gly Gln Val Tyr Phe Gly Ile Ile Ala Leu
545                 550                 555

<210> SEQ ID NO 75
<211> LENGTH: 576
<212> TYPE: PRT
<213> ORGANISM: Artificial Sequence
<220> FEATURE:
<223> OTHER INFORMATION: Amino acid sequence of the huIL2-F16-huTNFalpha
      (R52F) mutant [extracellular domain] conjugate

<400> SEQUENCE: 75

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

-continued

```
            100                 105                 110
Thr Ile Val Glu Phe Leu Asn Arg Trp Ile Thr Phe Cys Gln Ser Ile
            115                 120                 125
Ile Ser Thr Leu Thr Gly Asp Gly Ser Gly Gly Ser Gly Gly Ala
130                 135                 140
Ser Glu Val Gln Leu Leu Glu Ser Gly Gly Gly Leu Val Gln Pro Gly
145                 150                 155                 160
Gly Ser Leu Arg Leu Ser Cys Ala Ala Ser Gly Phe Thr Phe Ser Arg
                165                 170                 175
Tyr Gly Met Ser Trp Val Arg Gln Ala Pro Gly Lys Gly Leu Glu Trp
            180                 185                 190
Val Ser Ala Ile Ser Gly Ser Gly Gly Ser Thr Tyr Tyr Ala Asp Ser
            195                 200                 205
Val Lys Gly Arg Phe Thr Ile Ser Arg Asp Asn Ser Lys Asn Thr Leu
        210                 215                 220
Tyr Leu Gln Met Asn Ser Leu Arg Ala Glu Asp Thr Ala Val Tyr Tyr
225                 230                 235                 240
Cys Ala Lys Ala His Asn Ala Phe Asp Tyr Trp Gly Gln Gly Thr Leu
                245                 250                 255
Val Thr Val Ser Arg Gly Gly Gly Gly Ser Gly Gly Gly Gly Ser Gly
            260                 265                 270
Gly Gly Gly Ser Glu Leu Thr Gln Asp Pro Ala Val Ser Val Ala
            275                 280                 285
Leu Gly Gln Thr Val Arg Ile Thr Cys Gln Gly Asp Ser Leu Arg Ser
        290                 295                 300
Tyr Tyr Ala Ser Trp Tyr Gln Gln Lys Pro Gly Gln Ala Pro Val Leu
305                 310                 315                 320
Val Ile Tyr Gly Lys Asn Asn Arg Pro Ser Gly Ile Pro Asp Arg Phe
                325                 330                 335
Ser Gly Ser Ser Ser Gly Asn Thr Ala Ser Leu Thr Ile Thr Gly Ala
                340                 345                 350
Gln Ala Glu Asp Glu Ala Asp Tyr Tyr Cys Asn Ser Ser Val Tyr Thr
            355                 360                 365
Met Pro Pro Val Val Phe Gly Gly Gly Thr Lys Leu Thr Val Leu Gly
            370                 375                 380
Ser Ser Ser Ser Gly Ser Ser Ser Ser Gly Ser Ser Ser Ser Gly Gly
385                 390                 395                 400
Pro Gln Arg Glu Glu Phe Pro Arg Asp Leu Ser Leu Ile Ser Pro Leu
                405                 410                 415
Ala Gln Ala Val Arg Ser Ser Ser Arg Thr Pro Ser Asp Lys Pro Val
            420                 425                 430
Ala His Val Val Ala Asn Pro Gln Ala Glu Gly Gln Leu Gln Trp Leu
            435                 440                 445
Asn Arg Phe Ala Asn Ala Leu Leu Ala Asn Gly Val Glu Leu Arg Asp
        450                 455                 460
Asn Gln Leu Val Val Pro Ser Glu Gly Leu Tyr Leu Ile Tyr Ser Gln
465                 470                 475                 480
Val Leu Phe Lys Gly Gln Gly Cys Pro Ser Thr His Val Leu Leu Thr
                485                 490                 495
His Thr Ile Ser Arg Ile Ala Val Ser Tyr Gln Thr Lys Val Asn Leu
            500                 505                 510
Leu Ser Ala Ile Lys Ser Pro Cys Gln Arg Glu Thr Pro Glu Gly Ala
        515                 520                 525
```

Glu Ala Lys Pro Trp Tyr Glu Pro Ile Tyr Leu Gly Gly Val Phe Gln
            530                 535                 540

Leu Glu Lys Gly Asp Arg Leu Ser Ala Glu Ile Asn Arg Pro Asp Tyr
545                 550                 555                 560

Leu Asp Phe Ala Glu Ser Gly Gln Val Tyr Phe Gly Ile Ile Ala Leu
                565                 570                 575

<210> SEQ ID NO 76
<211> LENGTH: 556
<212> TYPE: PRT
<213> ORGANISM: Artificial Sequence
<220> FEATURE:
<223> OTHER INFORMATION: Amino acid sequence of the huIL2-F16-huTNFalpha
      (R32V) mutant [soluble form] conjugate

<400> SEQUENCE: 76

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Asp Gly Ser Ser Gly Gly Ser Gly Gly Ala
    130                 135                 140

Ser Glu Val Gln Leu Leu Glu Ser Gly Gly Gly Leu Val Gln Pro Gly
145                 150                 155                 160

Gly Ser Leu Arg Leu Ser Cys Ala Ala Ser Gly Phe Thr Phe Ser Arg
                165                 170                 175

Tyr Gly Met Ser Trp Val Arg Gln Ala Pro Gly Lys Gly Leu Glu Trp
            180                 185                 190

Val Ser Ala Ile Ser Gly Ser Gly Gly Ser Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Tyr
225                 230                 235                 240

Cys Ala Lys Ala His Asn Ala Phe Asp Tyr Trp Gly Gln Gly Thr Leu
                245                 250                 255

Val Thr Val Ser Arg Gly Gly Gly Gly Ser Gly Gly Gly Gly Ser Gly
            260                 265                 270

Gly Gly Gly Ser Ser Glu Leu Thr Gln Asp Pro Ala Val Ser Val Ala
        275                 280                 285

Leu Gly Gln Thr Val Arg Ile Thr Cys Gln Gly Asp Ser Leu Arg Ser
    290                 295                 300

Tyr Tyr Ala Ser Trp Tyr Gln Gln Lys Pro Gly Gln Ala Pro Val Leu

```
                    305                 310                 315                 320
Val Ile Tyr Gly Lys Asn Asn Arg Pro Ser Gly Ile Pro Asp Arg Phe
                325                 330                 335

Ser Gly Ser Ser Ser Gly Asn Thr Ala Ser Leu Thr Ile Thr Gly Ala
                340                 345                 350

Gln Ala Glu Asp Glu Ala Asp Tyr Tyr Cys Asn Ser Ser Val Tyr Thr
                355                 360                 365

Met Pro Pro Val Val Phe Gly Gly Gly Thr Lys Leu Thr Val Leu Gly
                370                 375                 380

Ser Ser Ser Ser Gly Ser Ser Ser Gly Ser Ser Ser Ser Gly Ser Val
385                 390                 395                 400

Arg Ser Ser Ser Arg Thr Pro Ser Asp Lys Pro Val Ala His Val Val
                405                 410                 415

Ala Asn Pro Gln Ala Glu Gly Gln Leu Gln Trp Leu Asn Arg Val Ala
                420                 425                 430

Asn Ala Leu Leu Ala Asn Gly Val Glu Leu Arg Asp Asn Gln Leu Val
                435                 440                 445

Val Pro Ser Glu Gly Leu Tyr Leu Ile Tyr Ser Gln Val Leu Phe Lys
                450                 455                 460

Gly Gln Gly Cys Pro Ser Thr His Val Leu Leu Thr His Thr Ile Ser
465                 470                 475                 480

Arg Ile Ala Val Ser Tyr Gln Thr Lys Val Asn Leu Leu Ser Ala Ile
                485                 490                 495

Lys Ser Pro Cys Gln Arg Glu Thr Pro Glu Gly Ala Glu Ala Lys Pro
                500                 505                 510

Trp Tyr Glu Pro Ile Tyr Leu Gly Gly Val Phe Gln Leu Glu Lys Gly
                515                 520                 525

Asp Arg Leu Ser Ala Glu Ile Asn Arg Pro Asp Tyr Leu Asp Phe Ala
                530                 535                 540

Glu Ser Gly Gln Val Tyr Phe Gly Ile Ile Ala Leu
545                 550                 555

<210> SEQ ID NO 77
<211> LENGTH: 576
<212> TYPE: PRT
<213> ORGANISM: Artificial Sequence
<220> FEATURE:
<223> OTHER INFORMATION: Amino acid sequence of the huIL2-F16-huTNFalpha
      (R52V) mutant [extracellular domain] conjugate

<400> SEQUENCE: 77

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
                50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Cys Gln Ser Ile
            115                 120                 125
Ile Ser Thr Leu Thr Gly Asp Gly Ser Ser Gly Gly Ser Gly Gly Ala
130                 135                 140
Ser Glu Val Gln Leu Leu Glu Ser Gly Gly Gly Leu Val Gln Pro Gly
145                 150                 155                 160
Gly Ser Leu Arg Leu Ser Cys Ala Ala Ser Gly Phe Thr Phe Ser Arg
                165                 170                 175
Tyr Gly Met Ser Trp Val Arg Gln Ala Pro Gly Lys Gly Leu Glu Trp
            180                 185                 190
Val Ser Ala Ile Ser Gly Ser Gly Gly Ser Thr Tyr Tyr Ala Asp Ser
        195                 200                 205
Val Lys Gly Arg Phe Thr Ile Ser Arg Asp Asn Ser Lys Asn Thr Leu
210                 215                 220
Tyr Leu Gln Met Asn Ser Leu Arg Ala Glu Asp Thr Ala Val Tyr Tyr
225                 230                 235                 240
Cys Ala Lys Ala His Asn Ala Phe Asp Tyr Trp Gly Gln Gly Thr Leu
                245                 250                 255
Val Thr Val Ser Arg Gly Gly Gly Gly Ser Gly Gly Gly Gly Ser Gly
            260                 265                 270
Gly Gly Gly Ser Ser Glu Leu Thr Gln Asp Pro Ala Val Ser Val Ala
        275                 280                 285
Leu Gly Gln Thr Val Arg Ile Thr Cys Gln Gly Asp Ser Leu Arg Ser
290                 295                 300
Tyr Tyr Ala Ser Trp Tyr Gln Gln Lys Pro Gly Gln Ala Pro Val Leu
305                 310                 315                 320
Val Ile Tyr Gly Lys Asn Asn Arg Pro Ser Gly Ile Pro Asp Arg Phe
                325                 330                 335
Ser Gly Ser Ser Ser Gly Asn Thr Ala Ser Leu Thr Ile Thr Gly Ala
            340                 345                 350
Gln Ala Glu Asp Glu Ala Asp Tyr Tyr Cys Asn Ser Ser Val Tyr Thr
        355                 360                 365
Met Pro Pro Val Val Phe Gly Gly Gly Thr Lys Leu Thr Val Leu Gly
370                 375                 380
Ser Ser Ser Ser Gly Ser Ser Ser Gly Ser Ser Ser Gly Gly
385                 390                 395                 400
Pro Gln Arg Glu Glu Phe Pro Arg Asp Leu Ser Leu Ile Ser Pro Leu
                405                 410                 415
Ala Gln Ala Val Arg Ser Ser Arg Thr Pro Ser Asp Lys Pro Val
            420                 425                 430
Ala His Val Val Ala Asn Pro Gln Ala Glu Gly Gln Leu Gln Trp Leu
        435                 440                 445
Asn Arg Val Ala Asn Ala Leu Leu Ala Asn Gly Val Glu Leu Arg Asp
450                 455                 460
Asn Gln Leu Val Val Pro Ser Glu Gly Leu Tyr Leu Ile Tyr Ser Gln
465                 470                 475                 480
Val Leu Phe Lys Gly Gln Gly Cys Pro Ser Thr His Val Leu Leu Thr
                485                 490                 495
His Thr Ile Ser Arg Ile Ala Val Ser Tyr Gln Thr Lys Val Asn Leu
            500                 505                 510
Leu Ser Ala Ile Lys Ser Pro Cys Gln Arg Glu Thr Pro Glu Gly Ala
        515                 520                 525
Glu Ala Lys Pro Trp Tyr Glu Pro Ile Tyr Leu Gly Gly Val Phe Gln
```

```
                    530                 535                 540
Leu Glu Lys Gly Asp Arg Leu Ser Ala Glu Ile Asn Arg Pro Asp Tyr
545                 550                 555                 560

Leu Asp Phe Ala Glu Ser Gly Gln Val Tyr Phe Gly Ile Ile Ala Leu
                565                 570                 575
```